(12) United States Patent
Engelhardt et al.

(10) Patent No.: US 11,684,679 B2
(45) Date of Patent: Jun. 27, 2023

(54) AAV-MEDIATED EXPRESSION USING A SYNTHETIC PROMOTER AND ENHANCER

(71) Applicant: University of Iowa Research Foundation, Iowa City, IA (US)

(72) Inventors: John F. Engelhardt, Iowa City, IA (US); Ziying Yan, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 578 days.

(21) Appl. No.: 16/082,767

(22) PCT Filed: Mar. 7, 2017

(86) PCT No.: PCT/US2017/021124
§ 371 (c)(1),
(2) Date: Sep. 6, 2018

(87) PCT Pub. No.: WO2017/155973
PCT Pub. Date: Sep. 14, 2017

(65) Prior Publication Data
US 2019/0083657 A1    Mar. 21, 2019

Related U.S. Application Data

(60) Provisional application No. 62/304,656, filed on Mar. 7, 2016.

(51) Int. Cl.
*C12N 15/00* (2006.01)
*A61K 48/00* (2006.01)
*C12N 15/86* (2006.01)
*A61K 47/55* (2017.01)

(52) U.S. Cl.
CPC .......... *A61K 48/0066* (2013.01); *A61K 47/55* (2017.08); *C12N 15/86* (2013.01); *C12N 2750/14041* (2013.01); *C12N 2750/14043* (2013.01); *C12N 2750/14143* (2013.01)

(58) Field of Classification Search
CPC .... A61K 48/0066; A61K 47/55; C12N 15/86; C12N 2750/14041; C12N 2750/14043; C12N 2750/14143
See application file for complete search history.

(56) References Cited

U.S. PATENT DOCUMENTS

| | | | |
|---|---|---|---|
| 4,501,729 A | 2/1985 | Boucher et al. | |
| 5,292,498 A | 3/1994 | Boucher, Jr. | |
| 5,478,745 A | 12/1995 | Samulski et al. | |
| 5,512,269 A | 4/1996 | Molina y Vedia et al. | |
| 5,604,090 A | 2/1997 | Alexander et al. | |
| 5,628,984 A | 5/1997 | Boucher, Jr. | |
| 5,635,160 A | 6/1997 | Stutts, III et al. | |
| 5,651,957 A | 7/1997 | Molina y Vedia et al. | |
| 5,656,256 A | 8/1997 | Boucher et al. | |
| 5,658,772 A | 8/1997 | Odell et al. | |
| 5,683,675 A | 11/1997 | Molina y Vedia et al. | |
| 5,691,176 A | 11/1997 | Lebkowski et al. | |
| 5,716,931 A | 2/1998 | Molina y Vedia et al. | |
| 5,725,842 A | 3/1998 | Boucher, Jr. et al. | |
| 5,801,030 A | 9/1998 | McVey et al. | |
| 5,831,068 A | 11/1998 | Nair et al. | |
| 5,834,182 A | 11/1998 | Alexander et al. | |
| 5,843,742 A | 12/1998 | Natsoulis et al. | |
| 5,849,706 A | 12/1998 | Molina y Vedia et al. | |
| 5,853,716 A | 12/1998 | Tattersall et al. | |
| 5,855,918 A | 1/1999 | Mrsny et al. | |
| 5,869,305 A | 2/1999 | Samulski et al. | |
| 5,876,700 A | 3/1999 | Boucher, Jr. et al. | |
| 5,902,567 A | 5/1999 | Boucher, Jr. | |
| 5,916,803 A | 6/1999 | Sedlacek et al. | |
| 5,935,555 A | 8/1999 | Stutts, III et al. | |
| 5,990,137 A | 11/1999 | Ternansky et al. | |
| 6,022,527 A | 2/2000 | Boucher, Jr. et al. | |
| 6,033,688 A | 3/2000 | Mrsny et al. | |
| 6,037,177 A | 3/2000 | Snyder | |
| 6,083,702 A | 7/2000 | Mitchell et al. | |
| 6,083,713 A | 7/2000 | Manly et al. | |
| 6,110,744 A | 8/2000 | Fang et al. | |
| 6,133,247 A | 10/2000 | Boucher, Jr. | |
| 6,143,279 A | 11/2000 | Boucher, Jr. et al. | |
| 6,153,436 A | 11/2000 | Hermonat et al. | |
| 6,156,303 A | 12/2000 | Russell et al. | |
| 6,200,560 B1 | 3/2001 | Couto et al. | |
| 6,214,536 B1 | 4/2001 | Boucher, Jr. | |
| 6,221,349 B1 | 4/2001 | Couto et al. | |
| 6,235,266 B1 | 5/2001 | Stutts, III et al. | |
| 6,264,975 B1 | 7/2001 | Boucher, Jr. | |
| 6,270,996 B1 | 8/2001 | Wilson et al. | |
| 6,287,569 B1 | 9/2001 | Kipps et al. | |
| 6,290,951 B1 | 9/2001 | Mikulski et al. | |
| 6,323,187 B1 | 11/2001 | Yerxa et al. | |
| 6,329,181 B1 | 12/2001 | Xiao et al. | |
| 6,358,524 B1 | 3/2002 | Sedlacek et al. | |
| 6,416,759 B1 | 7/2002 | Firestone et al. | |
| 6,420,347 B1 | 7/2002 | Jacobus et al. | |
| 6,436,392 B1 | 8/2002 | Engelhardt et al. | |
| 6,451,288 B1 | 9/2002 | Boucher, Jr. et al. | |
| 6,468,771 B1 | 10/2002 | Einerhand et al. | |

(Continued)

FOREIGN PATENT DOCUMENTS

AU       4091299      12/1999
AU       0759093       4/2003
(Continued)

OTHER PUBLICATIONS

Yan et al. ("Optimization of Recombinant Adeno-Associated Virus-Mediated Expression for Large Transgenes, Using a Synthetic Promoter and Tandem Array Enhancers" in Human Gene Therapy 2015 vol. 26: pp. 334-346; published online Mar. 11, 2015). (Year: 2015).*

(Continued)

*Primary Examiner* — Catherine S Hibbert
(74) *Attorney, Agent, or Firm* — Schwegman Lundberg & Woessner, P.A.

(57) ABSTRACT

An isolated recombinant parvovirus vector comprising a synthetic enhancer comprising plurality of enhancer sequences operably linked to a promoter, and methods of using the vector, are provided.

15 Claims, 35 Drawing Sheets

Specification includes a Sequence Listing.

(56) References Cited

U.S. PATENT DOCUMENTS

| | | |
|---|---|---|
| 6,475,509 B1 | 11/2002 | Boucher, Jr. |
| 6,475,537 B1 | 11/2002 | King et al. |
| 6,485,950 B1 | 11/2002 | Kumar et al. |
| 6,491,907 B1 | 12/2002 | Rabinowitz et al. |
| 6,492,429 B1 | 12/2002 | Graus et al. |
| 6,521,225 B1 | 2/2003 | Srivastava et al. |
| 6,544,786 B1 | 4/2003 | Xiao et al. |
| 6,586,416 B2 | 7/2003 | Bubien |
| 6,596,535 B1 | 7/2003 | Carter |
| 6,602,667 B1 | 8/2003 | Walker et al. |
| 6,607,741 B2 | 8/2003 | Boucher, Jr. |
| 6,613,345 B2 | 9/2003 | Boucher, Jr. |
| 6,630,344 B1 | 10/2003 | Fang et al. |
| 6,642,051 B1 | 11/2003 | Lynch et al. |
| 6,670,365 B1 | 12/2003 | Gallemi et al. |
| 6,855,549 B1 | 2/2005 | McCray, Jr. et al. |
| 6,897,045 B2 | 5/2005 | Engelhardt et al. |
| 7,060,497 B2 | 6/2006 | Nakai et al. |
| 7,067,659 B2 | 6/2006 | Stamler et al. |
| 7,122,335 B1 | 10/2006 | Engelhardt et al. |
| 7,125,717 B2 | 10/2006 | Carter |
| 7,129,374 B2 | 10/2006 | Weissbach et al. |
| 7,241,447 B1 | 7/2007 | Engelhardt et al. |
| 7,749,491 B2 | 7/2010 | Engelhardt et al. |
| 7,803,622 B2 | 9/2010 | Engelhardt et al. |
| 8,110,350 B2 | 2/2012 | Allander et al. |
| 8,241,622 B2 | 8/2012 | Engelhardt et al. |
| 8,846,030 B2 | 9/2014 | Engelhardt et al. |
| 9,828,587 B2 | 11/2017 | Yan et al. |
| 10,793,835 B2 | 10/2020 | Yan et al. |
| 11,142,775 B2 | 10/2021 | Yan et al. |
| 2001/0034349 A1 | 10/2001 | Boucher, Jr. |
| 2001/0041682 A1 | 11/2001 | Stutts, III et al. |
| 2001/0051611 A1 | 12/2001 | Srivastava et al. |
| 2002/0045264 A1 | 4/2002 | During et al. |
| 2002/0076754 A1 | 6/2002 | Sun et al. |
| 2002/0095135 A1 | 7/2002 | Meeker et al. |
| 2002/0099023 A1 | 7/2002 | Boucher, Jr. |
| 2002/0115619 A1 | 8/2002 | Rubenstein et al. |
| 2002/0128203 A1 | 9/2002 | Schild |
| 2002/0131956 A1 | 9/2002 | Walsh et al. |
| 2002/0132770 A1 | 9/2002 | Caplan et al. |
| 2002/0137017 A1 | 9/2002 | Aronheim |
| 2002/0156057 A1 | 10/2002 | Bubien |
| 2002/0158255 A1 | 10/2002 | Boucher, Jr. |
| 2002/0165239 A1 | 11/2002 | Boucher, Jr. |
| 2002/0197237 A1 | 12/2002 | Engelhardt et al. |
| 2003/0003583 A1 | 1/2003 | Hirsch et al. |
| 2003/0053990 A1 | 3/2003 | Rabinowitz et al. |
| 2003/0087818 A1 | 5/2003 | Jiang et al. |
| 2003/0103939 A1 | 6/2003 | Engelhardt et al. |
| 2003/0108920 A1 | 6/2003 | Zhang et al. |
| 2003/0148506 A1 | 8/2003 | Kotin |
| 2003/0166284 A1 | 9/2003 | Srivastava et al. |
| 2004/0029106 A1 | 2/2004 | Samulski et al. |
| 2004/0235947 A1 | 11/2004 | Paquin et al. |
| 2004/0248301 A1 | 12/2004 | Engelhardt et al. |
| 2005/0037497 A1 | 2/2005 | Engelhardt et al. |
| 2005/0095225 A1 | 5/2005 | Engelhardt et al. |
| 2005/0158281 A1 | 7/2005 | Chamberlain et al. |
| 2005/0181423 A1 | 8/2005 | Barak et al. |
| 2005/0239807 A1 | 10/2005 | Stamler et al. |
| 2005/0255087 A1 | 11/2005 | Engelhardt et al. |
| 2006/0093585 A1 | 5/2006 | Engelhardt et al. |
| 2007/0110724 A1 | 5/2007 | Samulski et al. |
| 2007/0265350 A1 | 11/2007 | Engelhardt et al. |
| 2008/0166758 A1 | 7/2008 | Engelhardt et al. |
| 2008/0206198 A1 | 8/2008 | Engelhardt et al. |
| 2008/0206792 A1 | 8/2008 | Engelhardt et al. |
| 2008/0213221 A1 | 9/2008 | Engelhardt et al. |
| 2008/0226600 A1 | 9/2008 | Engelhardt et al. |
| 2008/0249050 A1 | 10/2008 | Engelhardt et al. |
| 2008/0261201 A1 | 10/2008 | Engelhardt et al. |
| 2008/0292654 A1 | 11/2008 | Allander et al. |
| 2009/0017062 A1 | 1/2009 | Engelhardt et al. |
| 2009/0239243 A1 | 9/2009 | Engelhardt et al. |
| 2009/0241206 A1 | 9/2009 | Sun et al. |
| 2009/0265796 A1 | 10/2009 | Engelhardt et al. |
| 2009/0297557 A1 | 12/2009 | Delwart et al. |
| 2011/0014723 A1 | 1/2011 | Erdman et al. |
| 2011/0054247 A1 | 3/2011 | Sun et al. |
| 2013/0012574 A1 | 1/2013 | Monahan et al. |
| 2016/0068821 A1 | 3/2016 | Yan et al. |
| 2018/0282684 A1 | 10/2018 | Kaspar |
| 2018/0282702 A1 | 10/2018 | Yan et al. |
| 2019/0203229 A1 | 7/2019 | Engelhardt et al. |
| 2019/0338312 A1 | 11/2019 | Yan et al. |
| 2021/0079421 A1 | 3/2021 | Yan et al. |
| 2021/0255170 A1 | 8/2021 | Engelhardt et al. |
| 2022/0154213 A1 | 5/2022 | Yan et al. |
| 2022/0195461 A1 | 6/2022 | Engelhardt et al. |
| 2022/0241436 A1 | 8/2022 | Engelhardt et al. |

FOREIGN PATENT DOCUMENTS

| | | |
|---|---|---|
| AU | 0784420 | 3/2006 |
| AU | 2017229347 A1 | 11/2018 |
| AU | 2014251099 B2 | 1/2019 |
| CA | 2302627 | 9/2001 |
| CA | 2328447 | 4/2007 |
| CN | 105431170 A | 3/2016 |
| CN | 105431170 B | 10/2019 |
| CN | 114340683 A | 4/2022 |
| CN | 114641318 A | 6/2022 |
| EA | 201892006 A1 | 4/2019 |
| EA | 202192819 A1 | 2/2022 |
| EA | 202192818 A1 | 3/2022 |
| EP | 0041682 A1 | 12/1981 |
| EP | 0132770 A1 | 2/1985 |
| EP | 0158255 A2 | 10/1985 |
| EP | 1153612 A1 | 11/2001 |
| EP | 1486567 A1 | 12/2004 |
| EP | 3426787 A1 | 1/2019 |
| EP | 2983707 B1 | 6/2019 |
| HK | 1217916 B | 9/2020 |
| IN | 10078DELNP2015 A | 4/2016 |
| JP | 2002538770 A | 11/2002 |
| JP | 2003501068 | 1/2003 |
| JP | 2003201255 | 7/2003 |
| JP | 2006521825 A | 9/2006 |
| JP | 4969002 | 4/2012 |
| JP | 2013518899 A | 5/2013 |
| JP | 2016518121 A | 6/2016 |
| JP | 6516725 B2 | 4/2019 |
| JP | 2022529457 A | 6/2022 |
| JP | 2022529470 A | 6/2022 |
| WO | WO-9413788 A1 | 6/1994 |
| WO | WO-9507351 A1 | 3/1995 |
| WO | WO-9513365 A1 | 5/1995 |
| WO | WO-9515384 A1 | 6/1995 |
| WO | WO-9522323 A1 | 8/1995 |
| WO | WO-9610402 A1 | 4/1996 |
| WO | WO-9722250 A1 | 6/1997 |
| WO | WO-9809657 A2 | 3/1998 |
| WO | WO-9824479 A1 | 6/1998 |
| WO | WO-9853839 A2 | 12/1998 |
| WO | WO-9918227 A1 | 4/1999 |
| WO | WO-9920773 A2 | 4/1999 |
| WO | WO-9932647 A1 | 7/1999 |
| WO | WO-9960146 A1 | 11/1999 |
| WO | WO-9961601 A2 | 12/1999 |
| WO | WO-0047220 A1 | 2/2000 |
| WO | WO-0028004 A1 | 5/2000 |
| WO | WO-0038709 A1 | 7/2000 |
| WO | WO-0065038 A2 | 11/2000 |
| WO | WO-0075365 A2 | 12/2000 |
| WO | WO-0075365 A3 | 12/2000 |
| WO | WO-0125465 A1 | 4/2001 |
| WO | WO-01025465 A1 | 4/2001 |
| WO | WO-0168888 A2 | 9/2001 |
| WO | WO-0183692 A2 | 11/2001 |
| WO | WO-0192551 A2 | 12/2001 |
| WO | WO-0212525 A2 | 2/2002 |
| WO | WO-0214526 A2 | 2/2002 |

(56) References Cited

FOREIGN PATENT DOCUMENTS

| WO | WO-0224172 A1 | 3/2002 |
|---|---|---|
| WO | WO-0224177 A2 | 3/2002 |
| WO | WO-02087306 A2 | 11/2002 |
| WO | WO-03006616 A2 | 1/2003 |
| WO | WO-03006990 A1 | 1/2003 |
| WO | WO-03042361 A2 | 5/2003 |
| WO | WO-03057847 A2 | 7/2003 |
| WO | WO-03087399 A1 | 10/2003 |
| WO | WO-03095667 A2 | 11/2003 |
| WO | WO-03104392 A2 | 12/2003 |
| WO | WO-2004010045 A1 | 1/2004 |
| WO | WO-04064844 A1 | 8/2004 |
| WO | WO-2004064844 A1 | 8/2004 |
| WO | WO-04089423 A2 | 10/2004 |
| WO | WO-04089423 A3 | 10/2004 |
| WO | WO-04090145 A3 | 10/2004 |
| WO | WO-2004090145 A2 | 10/2004 |
| WO | WO-2004112727 A2 | 12/2004 |
| WO | WO-2005056762 A2 | 6/2005 |
| WO | WO-05111220 A2 | 11/2005 |
| WO | WO-2005105806 A1 | 11/2005 |
| WO | WO-2005111220 A3 | 11/2005 |
| WO | WO-2005116224 A2 | 12/2005 |
| WO | WO-2005119251 A2 | 12/2005 |
| WO | WO-2006009975 A2 | 1/2006 |
| WO | WO-2006116503 A2 | 11/2006 |
| WO | WO-2007079141 A2 | 7/2007 |
| WO | WO-2007079141 C2 | 7/2007 |
| WO | WO-2007127464 A2 | 11/2007 |
| WO | WO-2007127464 A3 | 11/2007 |
| WO | WO-2008034637 A1 | 3/2008 |
| WO | WO-2008133904 A1 | 11/2008 |
| WO | WO-2009028387 A1 | 3/2009 |
| WO | WO-2011097456 A2 | 8/2011 |
| WO | WO-2014168953 A1 | 10/2014 |
| WO | WO-2015164758 A1 | 10/2015 |
| WO | WO-201 7139381 A1 | 8/2017 |
| WO | WO-2017155973 A1 | 9/2017 |
| WO | WO-2017205739 A1 | 11/2017 |
| WO | WO-201 8132747 A1 | 7/2018 |
| WO | WO-201 9178267 A2 | 9/2019 |
| WO | WO-201 9178267 A3 | 9/2019 |
| WO | WO-2020214668 A1 | 10/2020 |
| WO | WO-2020214672 A1 | 10/2020 |
| WO | WO-2022006253 A2 | 1/2022 |
| WO | WO-2022006253 A3 | 1/2022 |

OTHER PUBLICATIONS

"International Application Serial No. PCT/US2017/021124, International Search Report dated May 22, 2017", 6 pgs.
"International Application Serial No. PCT/US2017/021124, Written Opinion dated May 22, 2017", 5 pgs.
Schlabach, Michael R, et al., "Synthetic design of strong promoters", Proceedings of the National Academy Of Sciences, vol. 107, No. 6, (Feb. 9, 2010), 2538-2543.
Ziying, Yan, et al., "Optimization of Recombinant Adeno-Associated Virus-Mediated Expression for Large Transgenes, Using a Synthetic Promoter and Tandem Array Enhancers", Human Gene Therapy, vol. 26, No. 6, (Jun. 1, 2015), 334-346.
"Canadian Application Serial No. 3,016,985, Examiner's Rule 30(2) Requisition mailed Jun. 28, 2019", 3 pgs.
"European Application Serial No. 17712339.5, Communication Pursuant to Article 94(3) EPC dated Aug. 20, 2019", 5 pgs.
"European Application Serial No. 17712339.5, Response Filed May 2, 2019 to Communication pursuant to Rules 161(2) and 162 EPC dated Oct. 23, 2018", 14 pgs.
"International Application Serial No. PCT/US2017/021124, International Preliminary Report on Patentability dated Sep. 20, 2018", 7 pgs.
Aitken, M L, et al., "A Phase I Study of Aerosolized Administration of tgAAVCF to Cystic Fibrosis Subjects with Mild Lung Disease", Hum Gene Ther 12, (2001), 1907-1916.

Flotte, T R, "(Abstract) Recombinant adeno-associated virus vectors for cystic fibrosis gene therapy", Curr Opin Mol Ther 3(5), pp. 497-502, (2001), 1 pg.
Flotte, T. R., "Expression of the Cystic Fibrosis Transmembrane Conductance Regulator From a Novel Adeno-Associated Virus Promoter", The Journal of Biological Chemistry, 268(5), (1993), 3781-3790.
Zhang, L. N., "Dual Therapeutic Utility of Proteasome Modulating Agents for Pharmaco-Gene Therapy of the Cystic Fibrosis Airway", Molecular Therapy, 10(6), (2004), 990-1002.
"Australian Application Serial No. 2017229347, First Examination Report dated Dec. 20, 2019", 3 pgs.
"Canadian Application Serial No. 3,016,985, Response filed Dec. 24, 2019 to Examiner's Rule 30(2) Requisition mailed Jun. 28, 2019", 40 pgs.
"European Application Serial No. 17712339.5, Response filed Dec. 23, 2019 to Communication Pursuant to Article 94(3) EPC dated Aug. 20, 2019", 9 pgs.
"Australian Application Serial No. 2017229347, Response filed Oct. 2, 2020 to First Examination Report dated Dec. 20, 2019", 19 pgs.
"Australian Application Serial No. 2017229347, Response filed Dec. 10, 2020 to Subsequent Examiners Report dated Oct. 8, 2020", 16 pgs.
"Australian Application Serial No. 2017229347, Subsequent Examiners Report dated Oct. 8, 2020", 6 pgs.
"Australian Application Serial No. 2017229347, Third Examiners Report dated Dec. 16, 2020", 4 pgs.
"Canadian Application Serial No. 3,016,985, Office Action dated Sep. 23, 2020", 7 pgs.
"European Application Serial No. 17712339.5, Communication Pursuant to Article 94(3) EPC dated Oct. 20, 2020", 4 pgs.
"Canadian Application Serial No. 3,016,985, Office Action dated Oct. 8, 2021", 6 pgs.
"Eurasian Application Serial No. 201892006, Response filed Nov. 24, 2021 to Office Action dated Jul. 1, 2021", w/ English claims, 10 pgs.
"Canadian Application Serial No. 3,016,985, Response filed Jan. 22, 2021 to Office Action dated Sep. 23, 2020", 14 pgs.
"European Application Serial No. 17712339.5, Response filed Feb. 24, 2021 to Communication Pursuant to Article 94(3) EPC dated Oct. 20, 2020", 10 pgs.
"Eurasian Application Serial No. 201892006, Office Action dated Jul. 1, 2021", w English Translation, 5 pgs.
"U.S. Appl. No. 09/276,625, 312 Amendment filed Jan. 10, 2002", 2 pgs.
"U.S. Appl. No. 09/276,625, Non Final Office Action dated Feb. 13, 2001", 9 pgs.
"U.S. Appl. No. 09/276,625, Notice of Allowance dated Oct. 10, 2001", 8 pgs.
"U.S. Appl. No. 09/276,625, Preliminary Amendment filed Jul. 20, 2000", 2 pgs.
"U.S. Appl. No. 09/276,625, PTO Response to 312 Amendment dated May 15, 2002", 2 pgs.
"U.S. Appl. No. 09/276,625, Response filed Aug. 13, 2001 to Non Final Office Action dated Feb. 13, 2001", 10 pgs.
"U.S. Appl. No. 09/276,625, Response filed Nov. 20, 2000 to Restriction Requirement dated Sep. 14, 2000", 5 pgs.
"U.S. Appl. No. 09/276,625, Restriction Requirement dated Sep. 14, 2000", 5 pgs.
"U.S. Appl. No. 09/684,554, Examiner Interview Summary dated May 17, 2005", 3 pgs.
"U.S. Appl. No. 09/684,554, Examiner Interview Summary dated Jun. 27, 2003", 2 pgs.
"U.S. Appl. No. 09/684,554, Examiner Interview Summary dated Sep. 7, 2004", 3 pgs.
"U.S. Appl. No. 09/684,554, Final Office Action dated Apr. 19, 2004", 10 pgs.
"U.S. Appl. No. 09/684,554, Final Office Action dated Apr. 19, 2004", 14 pgs.
"U.S. Appl. No. 09/684,554, Final Office Action dated Nov. 15, 2005", 11 pgs.

(56) References Cited

OTHER PUBLICATIONS

"U.S. Appl. No. 09/684,554, Final Office Action dated Nov. 15, 2005", 10 pgs.
"U.S. Appl. No. 09/684,554, Non-Final Office Action dated Feb. 25, 2005", 9 pgs.
"U.S. Appl. No. 09/684,554, Non-Final Office Action dated Mar. 11, 2003", 14 pgs.
"U.S. Appl. No. 09/684,554, Non-Final Office Action dated Mar. 11, 2003", 10 pgs.
"U.S. Appl. No. 09/684,554, Non-Final Office Action dated Jul. 20, 2006", 9 pgs.
"U.S. Appl. No. 09/684,554, Non-Final Office Action dated Jul. 20, 2006", 10 pgs.
"U.S. Appl. No. 09/684,554, Notice of Allowance dated Mar. 2, 2007", 7 pgs.
"U.S. Appl. No. 09/684,554, Response filed Apr. 10, 2006 to Final Office Action dated Nov. 15, 2005", 14 pgs.
"U.S. Appl. No. 09/684,554, Response filed Jun. 4, 2002 to Restriction Requirement dated Dec. 4, 2001", 6 pgs.
"U.S. Appl. No. 09/684,554, Response filed Aug. 11, 2003 to Non Final Office Action dated Mar. 11, 2003", 13 pgs.
"U.S. Appl. No. 09/684,554, Response filed Aug. 17, 2005 to Non Final Office Action dated Feb. 25, 2005", 15 pgs.
"U.S. Appl. No. 09/684,554, Response filed Oct. 19, 2004 to Final Office Action dated Apr. 19, 2004", 14 pgs.
"U.S. Appl. No. 09/684,554, Response filed Nov. 20, 2006 to Non Final Office Action dated Jul. 20, 2006", 15 pgs.
"U.S. Appl. No. 09/684,554, Response filed Nov. 26, 2002 to Restriction Requirement dated Aug. 26, 2002", 13 pgs.
"U.S. Appl. No. 09/684,554, Restriction Requirement dated Aug. 26, 2002", 10 pgs.
"U.S. Appl. No. 09/684,554, Restriction Requirement dated Dec. 4, 2001", 6 pgs.
"U.S. Appl. No. 09/689,136, Advisory Action dated Nov. 3, 2004", 3 pgs.
"U.S. Appl. No. 09/689,136, Examiner Interview Summary dated Apr. 18, 2005", 3 pgs.
"U.S. Appl. No. 09/689,136, Examiner Interview Summary dated May 16, 2005", 3 pgs.
"U.S. Appl. No. 09/689,136, Examiner Interview Summary dated Sep. 28, 2004", 3 pgs.
"U.S. Appl. No. 09/689,136, Final Office Action dated Feb. 24, 2003", 11 pgs.
"U.S. Appl. No. 09/689,136, Final Office Action dated Jun. 18, 2004", 8 pgs.
"U.S. Appl. No. 09/689,136, Non Final Office Action dated Jan. 7, 2005", 10 pgs.
"U.S. Appl. No. 09/689,136, Non Final Office Action dated Jun. 26, 2002", 13 pgs.
"U.S. Appl. No. 09/689,136, Non Final Office Action dated Aug. 12, 2003", 8 pgs.
"U.S. Appl. No. 09/689,136, Notice of Allowance dated Sep. 12, 2005", 10 pgs.
"U.S. Appl. No. 09/689,136, Preliminary Amendment filed Oct. 12, 2000", 2 pgs.
"U.S. Appl. No. 09/689,136, Response filed Jan. 12, 2004 to Non Final Office Action dated Aug. 12, 2003", 12 pgs.
"U.S. Appl. No. 09/689,136, Response filed Apr. 11, 2002 to Restriction Requirement dated Oct. 11, 2001", 12 pgs.
"U.S. Appl. No. 09/689,136, Response filed May 18, 2005 to Non Final Office Action dated Jan. 7, 2005", 14 pgs.
"U.S. Appl. No. 09/689,136, Response filed May 30, 2003 to Final Office Action dated Feb. 24, 2003", 13 pgs.
"U.S. Appl. No. 09/689,136, Response filed Oct. 18, 2004 to Final Office Action dated Jun. 18, 2004", 13 pgs.
"U.S. Appl. No. 09/689,136, Response filed Nov. 26, 2002 to Non Final Office Action dated Jun. 26, 2002", 14 pgs.
"U.S. Appl. No. 09/689,136, Restriction Requirement dated Oct. 11, 2001", 9 pgs.
"U.S. Appl. No. 09/689,136, Supplemental Amendment filed Aug. 3, 2005", 13 pgs.
"U.S. Appl. No. 09/689,136, Supplemental Amendment filed Nov. 18, 2004", 11 pgs.
"U.S. Appl. No. 10/054,665, Non-Final Office Action dated Jun. 16, 2004", 7 pgs.
"U.S. Appl. No. 10/054,665, Notice of Allowance dated Nov. 8, 2004", 10 pgs.
"U.S. Appl. No. 10/054,665, Preliminary Amendment filed Jun. 25, 2002", 10 pgs.
"U.S. Appl. No. 10/054,665, Response filed Mar. 24, 2004 to Restriction Requirement dated Feb. 24, 2004", 1 pg.
"U.S. Appl. No. 10/054,665, Response filed Sep. 16, 2004 to Non-Final Office Action dated Jun. 16, 2004", 13 pgs.
"U.S. Appl. No. 10/054,665, Restriction Requirement dated Feb. 24, 2004", 5 pgs.
"U.S. Appl. No. 10/194,421, Preliminary Amendment filed Jan. 14, 2003", 2 pgs.
"U.S. Appl. No. 10/194,421, Restriction Requirement dated Mar. 21, 2005", 5 pgs.
"U.S. Appl. No. 10/815,262, Advisory Action dated Aug. 14, 2008", 3 pgs.
"U.S. Appl. No. 10/815,262, Examiner Interview Summary dated Feb. 6, 2007", 4 pgs.
"U.S. Appl. No. 10/815,262, Examiner Interview Summary dated Mar. 30, 2009", 4 pgs.
"U.S. Appl. No. 10/815,262, Examiner Interview Summary dated Nov. 18, 2009", 4 pgs.
"U.S. Appl. No. 10/815,262, Final Office Action dated Apr. 23, 2008", 24 pgs.
"U.S. Appl. No. 10/815,262, Final Office Action dated Aug. 6, 2009", 24 pgs.
"U.S. Appl. No. 10/815,262, Non Final Office Action dated May 15, 2007", 25 pgs.
"U.S. Appl. No. 10/815,262, Non-Final Office Action dated Oct. 30, 2007", 24 pgs.
"U.S. Appl. No. 10/815,262, Non-Final Office Action dated Dec. 4, 2008", 28 pgs.
"U.S. Appl. No. 10/815,262, Notice of Allowance dated Feb. 23, 2010", 9 pgs.
"U.S. Appl. No. 10/815,262, Response filed Jan. 31, 2008 to Non-Final Office Action dated Oct. 30, 2007", 26 pgs.
"U.S. Appl. No. 10/815,262, Response filed Mar. 19, 2007 to Restriction Requirement dated Sep. 18, 2006", 15 pgs.
"U.S. Appl. No. 10/815,262, Response filed May 4, 2009 to Non Final Office Action dated Dec. 4, 2008", 22 pgs.
"U.S. Appl. No. 10/815,262, Response filed Jul. 23, 2008 to Final Office Action dated Apr. 23, 2008", 22 pgs.
"U.S. Appl. No. 10/815,262, Response filed Aug. 14, 2007 to Non Final Office Action dated May 15, 2007", 24 pgs.
"U.S. Appl. No. 10/815,262, Response filed Dec. 7, 2009 to Final Office Action dated Aug. 6, 2009", 11 pgs.
"U.S. Appl. No. 10/815,262, Restriction Requirement dated Sep. 18, 2006", 15 pgs.
"U.S. Appl. No. 10/815,262, Supplemental Amendment filed Aug. 22, 2007", 1 pg.
"U.S. Appl. No. 10/815,557, Examiner Interview Summary dated Feb. 6, 2007", 4 pgs.
"U.S. Appl. No. 10/815,557, Final Office Action dated Nov. 14, 2007", 29 pgs.
"U.S. Appl. No. 10/815,557, Non Final Office Action dated May 21, 2007", 24 pgs.
"U.S. Appl. No. 10/815,557, Non-Final Office Action dated Feb. 3, 2009", 23 pgs.
"U.S. Appl. No. 10/815,557, Non-Final Office Action dated Aug. 13, 2008", 25 pgs.
"U.S. Appl. No. 10/815,557, Preliminary Amendment filed Dec. 28, 2004", 4 pgs.
"U.S. Appl. No. 10/815,557, Response filed Mar. 27, 2007 to Restriction Requirement dated Oct. 5, 2006", 13 pgs.
"U.S. Appl. No. 10/815,557, Response filed May 14, 2008 to Final Office Action dated Nov. 14, 2007", 18 pgs.

(56) References Cited

OTHER PUBLICATIONS

"U.S. Appl. No. 10/815,557, Response filed Aug. 21, 2007 to Non Final Office Action dated May 21, 2007", 22 pgs.
"U.S. Appl. No. 10/815,557, Response filed Nov. 13, 2008 to Non-Final Office Action dated Aug. 13, 2008", 19 pgs.
"U.S. Appl. No. 10/815,557, Restriction Requirement dated Oct. 5, 2006", 19 pgs.
"U.S. Appl. No. 10/837,029, Examiner Interview Summary dated Jan. 9, 2012", 3 pgs.
"U.S. Appl. No. 10/837,029, Examiner Interview Summary dated Nov. 15, 2007", 3 pgs.
"U.S. Appl. No. 10/837,029, Final Office Action dated Jan. 8, 2009", 9 pgs.
"U.S. Appl. No. 10/837,029, Final Office Action dated Mar. 9, 2012", 10 pgs.
"U.S. Appl. No. 10/837,029, Final Office Action dated Sep. 13, 2010", 13 pgs.
"U.S. Appl. No. 10/837,029, Non Final Office Action dated Apr. 11, 2007", 9 pgs.
"U.S. Appl. No. 10/837,029, Non Final Office Action dated Oct. 7, 2011", 17 pgs.
"U.S. Appl. No. 10/837,029, Non-Final Office Action dated Mar. 24, 2010", 11 pgs.
"U.S. Appl. No. 10/837,029, Non-Final Office Action dated Jun. 2, 2008", 8 pgs.
"U.S. Appl. No. 10/837,029, Non-Final Office Action dated Jun. 23, 2009", 11 pgs.
"U.S. Appl. No. 10/837,029, Non-Final Office Action dated Jul. 15, 2008", 7 pgs.
"U.S. Appl. No. 10/837,029, Notice of Allowance dated Apr. 11, 2012", 10 pgs.
"U.S. Appl. No. 10/837,029, Notice of Allowance dated Nov. 15, 2007", 8 pgs.
"U.S. Appl. No. 10/837,029, Preliminary Amendment dated Feb. 15, 2008", 12 pgs.
"U.S. Appl. No. 10/837,029, Response filed Jan. 6, 2012 to Non Final Office Action dated Oct. 7, 2011", 18 pgs.
"U.S. Appl. No. 10/837,029, Response filed Feb. 15, 2007 to Restriction Requirement dated Nov. 15, 2006", 17 pgs.
"U.S. Appl. No. 10/837,029, Response filed Mar. 22, 2012 to Final Office Action dated Mar. 9, 2012", 15 pgs.
"U.S. Appl. No. 10/837,029, Response filed Apr. 6, 2009 to Final Office Action dated Jan. 8, 2009", 13 pgs.
"U.S. Appl. No. 10/837,029, Response filed Jun. 21, 2010 to Non-Final Office Action dated Mar. 24, 2010", 14 pgs.
"U.S. Appl. No. 10/837,029, Response filed Aug. 17, 2007 to Non-Final Office Action dated Apr. 11, 2007", 20 pgs.
"U.S. Appl. No. 10/837,029, Response filed Oct. 15, 2008 to Non-Final Office Action dated Jul. 15, 2008", 13 pgs.
"U.S. Appl. No. 10/837,029, Response filed Nov. 19, 09 to Non Final Office Action mailed Jun. 23, 09", 14 pgs.
"U.S. Appl. No. 10/837,029, Response filed Dec. 8, 2010 to Final Office Action dated Sep. 13, 2010", 18 pgs.
"U.S. Appl. No. 10/837,029, Restriction Requirement dated Nov. 15, 2006", 6 pgs.
"U.S. Appl. No. 10/837,029, Supplemental Amendment filed Oct. 16, 2007 to Non-Final Office Action dated Apr. 11, 2007", 14 pgs.
"U.S. Appl. No. 11/058,751, Advisory Action dated Dec. 8, 2008", 3 pgs.
"U.S. Appl. No. 11/058,751, Final Office Action dated Jan. 4, 2010", 6 pgs.
"U.S. Appl. No. 11/058,751, Final Office Action dated Mar. 3, 2009", 7 pgs.
"U.S. Appl. No. 11/058,751, Final Office Action dated Apr. 19, 2007", 7 pgs.
"U.S. Appl. No. 11/058,751, Non Final Office Action dated Aug. 25, 2006", 12 pgs.
"U.S. Appl. No. 11/058,751, Non-Final Office Action dated Jan. 28, 2008", 5 pgs.
"U.S. Appl. No. 11/058,751, Non-Final Office Action dated Jun. 12, 2009", 6 pgs.
"U.S. Appl. No. 11/058,751, Non-Final Office Action dated Jul. 22, 2008", 6 pgs.
"U.S. Appl. No. 11/058,751, Notice of Allowance dated May 3, 2010", 4 pgs.
"U.S. Appl. No. 11/058,751, Response filed Jan. 25, 2007 to Non Final Office Action dated Aug. 25, 2006", 10 pgs.
"U.S. Appl. No. 11/058,751, Response filed Apr. 5, 2010 to Final Office Action dated Jan. 4, 2010", 6 pgs.
"U.S. Appl. No. 11/058,751, Response filed Apr. 22, 2008 to Non-Final Office Action dated Jan. 28, 2008", 7 pgs.
"U.S. Appl. No. 11/058,751, Response filed Jun. 3, 2009 to Final Office Action dated Mar. 3, 2009", 7 pgs.
"U.S. Appl. No. 11/058,751, Response filed Jun. 14, 2006 to Restriction Requirement dated Dec. 14, 2005", 9 pgs.
"U.S. Appl. No. 11/058,751, Response filed Aug. 17, 2007 to Final Office Action dated Apr. 19, 2007", 9 pgs.
"U.S. Appl. No. 11/058,751, Response filed Sep. 14, 2009 to Non Final Office Action dated Jun. 12, 2009", 8 pgs.
"U.S. Appl. No. 11/058,751, Response filed Oct. 22, 2008 to Non Final Office Action dated Jul. 22, 2008", 6 pgs.
"U.S. Appl. No. 11/058,751, Restriction Requirement dated Dec. 14, 2005", 6 pgs.
"U.S. Appl. No. 11/058,751, Supplemental Amendment filed Oct. 19, 2007", 8 pgs.
"U.S. Appl. No. 11/301,601, Advisory Action dated Mar. 24, 2008", 6 pgs.
"U.S. Appl. No. 11/301,601, Examiner Interview Summary dated Jan. 31, 2013", 3 pgs.
"U.S. Appl. No. 11/301,601, Examiner Interview Summary dated Apr. 25, 2007", 4 pgs.
"U.S. Appl. No. 11/301,601, Examiner Interview Summary dated May 28, 2010", 3 pgs.
"U.S. Appl. No. 11/301,601, Final Office Action dated Mar. 30, 2010", 16 pgs.
"U.S. Appl. No. 11/301,601, Final Office Action dated Apr. 3, 2009", 16 pgs.
"U.S. Appl. No. 11/301,601, Final Office Action dated Dec. 6, 2011", 12 pgs.
"U.S. Appl. No. 11/301,601, Final Office Action dated Dec. 13, 2007", 15 pgs.
"U.S. Appl. No. 11/301,601, Non Final Office Action dated Mar. 28, 2013", 12 pgs.
"U.S. Appl. No. 11/301,601, Non Final Office Action dated Jun. 27, 2011", 10 pgs.
"U.S. Appl. No. 11/301,601, Non-Final Office Action dated Nov. 22, 2013", 13 pgs.
"U.S. Appl. No. 11/301,601, Non-Final Office Action ated Jul. 12, 2007", 29 pgs.
"U.S. Appl. No. 11/301,601, Non-Final Office Action dated Sep. 28, 2009", 13 pgs.
"U.S. Appl. No. 11/301,601, Non-Final Office Action dated Oct. 2, 2008", 15 pgs.
"U.S. Appl. No. 11/301,601, Notice of Allowance dated May 22, 2014", 7 pgs.
"U.S. Appl. No. 11/301,601, Preliminary Amendment filed Dec. 13, 2005", 9 pgs.
"U.S. Appl. No. 11/301,601, Response filed Jan. 4, 2010 to Non Final Office Action dated Sep. 28, 2009", 12 pgs.
"U.S. Appl. No. 11/301,601, Response filed Feb. 21, 2014 to Non Final Office Action dated Nov. 22, 2013", 11 pgs.
"U.S. Appl. No. 11/301,601, Response filed Mar. 13, 2008 to Final Office Action dated Dec. 13, 2007", 10 pgs.
"U.S. Appl. No. 11/301,601, Response filed Mar. 22, 2012 to Final Office Action dated Dec. 6, 2011", 11 pgs.
"U.S. Appl. No. 11/301,601, Response filed May 2, 2007 to Restriction Requirement dated Jan. 3, 2007", 11 pgs.
"U.S. Appl. No. 11/301,601, Response filed Jun. 27, 2013 to Non Final Office Action dated Mar. 28, 2013", 11 pgs.
"U.S. Appl. No. 11/301,601, Response filed Jun. 30, 2010 to Final Office Action dated Mar. 30, 2010", 11 pgs.

(56) References Cited

OTHER PUBLICATIONS

"U.S. Appl. No. 11/301,601, Response filed Jul. 1, 2009 to Final Office Action dated Apr. 3, 2009", 12 pgs.
"U.S. Appl. No. 11/301,601, Response filed Sep. 27, 2011 to Non-Final Office Action dated Jun. 27, 2011", 10 pgs.
"U.S. Appl. No. 11/301,601, Response filed Oct. 11, 2007 to Non-Final Office Action dated Jul. 12, 2007", 14 pgs.
"U.S. Appl. No. 11/301,601, Response filed Dec. 31, 2008 to Non Final Office Action dated Oct. 2, 2008", 12 pgs.
"U.S. Appl. No. 11/301,601, Restriction Requirement dated Jan. 3, 2007", 5 pgs.
"U.S. Appl. No. 11/301,601, Second Preliminary Amendment filed Jan. 25, 2006", 3 pgs.
"U.S. Appl. No. 11/617,491, Response filed Oct. 3, 2013 to Non Final Office Action dated Jul. 3, 2013", 10 pgs.
"U.S. Appl. No. 11/617,491, Decision on Appeal Brief mailed Apr. 3, 2014", 2 pgs.
"U.S. Appl. No. 11/617,491, Examiner Interview Summary dated Jul. 30, 2010", 3 pgs.
"U.S. Appl. No. 11/617,491, Final Office Action dated Mar. 2, 2009", 11 pgs.
"U.S. Appl. No. 11/617,491, Final Office Action dated Nov. 8, 2013", 11 pgs.
"U.S. Appl. No. 11/617,491, Final Office Action dated Nov. 26, 2010", 12 pgs.
"U.S. Appl. No. 11/617,491, Non Final Office Action dated Jul. 3, 2013", 9 pgs.
"U.S. Appl. No. 11/617,491, Non-Final Office Action dated May 27, 2010", 19 pgs.
"U.S. Appl. No. 11/617,491, Non-Final Office Action dated Jun. 26, 2008", 11 pgs.
"U.S. Appl. No. 11/617,491, Non-Final Office Action dated Oct. 2, 2009", 7 pgs.
"U.S. Appl. No. 11/617,491, Pre Appeal Brief Request for Review filed Jan. 9, 2014", 5 pgs.
"U.S. Appl. No. 11/617,491, Preliminary Amendment filed Apr. 11, 2007", 5 pgs.
"U.S. Appl. No. 11/617,491, Response filed Jan. 21, 2011 to Final Office Action dated Nov. 26, 2010", 15 pgs.
"U.S. Appl. No. 11/617,491, Response filed Jan. 28, 2010 to Non-Final Office Action dated Oct. 2, 2009", 9 pgs.
"U.S. Appl. No. 11/617,491, Response filed Feb. 8, 2008 to Restriction Requirement dated Dec. 28, 2007", 10 pgs.
"U.S. Appl. No. 11/617,491, Response filed Jun. 30, 2009 to Final Office Action dated Mar. 2, 2009", 14 pgs.
"U.S. Appl. No. 11/617,491, Response filed Aug. 26, 2010 to Non Final Office Action dated May 27, 2010", 14 pgs.
"U.S. Appl. No. 11/617,491, Response filed Nov. 26, 2008 to Non Final Office Action dated Jun. 26, 2008", 12 pgs.
"U.S. Appl. No. 11/617,491, Restriction Requirement dated Dec. 28, 2007", 8 pgs.
"U.S. Appl. No. 11/796,605, Preliminary Amendment filed Sep. 11, 2007", 6 pgs.
"U.S. Appl. No. 11/796,605, Restriction Requirement dated Jul. 7, 2009", 7 pgs.
"U.S. Appl. No. 11/821,116, Restriction Requirement dated Jun. 26, 2009", 8 pgs.
"U.S. Appl. No. 11/890,761, Final Office Action dated Dec. 22, 2009", 40 pgs.
"U.S. Appl. No. 11/890,761, Non Final Office Action dated Jul. 12, 2011", 15 pgs.
"U.S. Appl. No. 11/890,761, Non-Final Office Action dated Jul. 16, 2009", 16 pgs.
"U.S. Appl. No. 11/890,761, Preliminary Amendment filed May 19, 2008", 8 pgs.
"U.S. Appl. No. 11/890,761, Response filed Mar. 16, 2010 to Final Office Action dated Dec. 22, 2009", 11 pgs.
"U.S. Appl. No. 11/890,761, Response filed Apr. 14, 2009 to Restriction Requirement dated Oct. 14, 2008", 7 pgs.
"U.S. Appl. No. 11/890,761, Response filed Oct. 29, 2009 to Non Final Office Action dated Jul. 16, 2009", 19 pgs.
"U.S. Appl. No. 11/890,761, Restriction Requirement dated Oct. 14, 2008", 5 pgs.
"U.S. Appl. No. 11/890,762, Restriction Requirement dated Jun. 23, 2009", 8 pgs.
"U.S. Appl. No. 11/890,767, Restriction Requirement dated Sep. 30, 2009", 8 pgs.
"U.S. Appl. No. 11/890,775, Response filed Dec. 2, 2009 to Restriction Requirement dated Oct. 2, 2009", 6 pgs.
"U.S. Appl. No. 11/890,775, Restriction Requirement dated Feb. 23, 2010", 6 pgs.
"U.S. Appl. No. 11/890,775, Restriction Requirement dated Oct. 2, 2009", 6 pgs.
"U.S. Appl. No. 11/890,776, Preliminary Amendment filed May 9, 2008", 6 pgs.
"U.S. Appl. No. 11/890,776, Restriction Requirement dated Dec. 17, 2008", 8 pgs.
"U.S. Appl. No. 11/890,777, Preliminary Amendment filed Aug. 7, 2007", 9 pgs.
"U.S. Appl. No. 11/890,777, Restriction Requirement dated Mar. 18, 2010", 5 pgs.
"U.S. Appl. No. 11/890,778, Preliminary Amendment filed Jan. 28, 2009", 4 pgs.
"U.S. Appl. No. 11/890,779, Preliminary Amendment filed May 9, 2008", 5 pgs.
"U.S. Appl. No. 11/890,779, Restriction Requirement dated Feb. 18, 2010", 5 pgs.
"U.S. Appl. No. 11/890,787, Preliminary Amendment filed May 12, 2008", 6 pgs.
"U.S. Appl. No. 11/890,787, Restriction Requirement dated Apr. 17, 2009", 5 pgs.
"U.S. Appl. No. 12/397,583, Non-Final Office Action dated Sep. 23, 2010", 16 pgs.
"U.S. Appl. No. 12/397,583, Response filed Aug. 9, 2010 to Restriction Requirement dated Jul. 20, 2010", 7 pgs.
"U.S. Appl. No. 12/397,583, Restriction Requirement dated Jul. 20, 2010", 12 pgs.
"U.S. Appl. No. 12/835,102, Preliminary Amendment filed Sep. 29, 2010", 10 pgs.
"U.S. Appl. No. 12/835,102, Restriction Requirement dated Jun. 7, 2011", 8 pgs.
"U.S. Appl. No. 14/782,876, Non Final Office Action dated Feb. 16, 2017", 10 pgs.
"U.S. Appl. No. 14/782,876, Notice of Allowance dated Jul. 25, 2017", 8 pgs.
"U.S. Appl. No. 14/782,876, Preliminary Amendment filed Oct. 7, 2015", 9 pgs.
"U.S. Appl. No. 14/782,876, Response filed Jan. 11, 2017 to Restriction Requirement dated Oct. 14, 2016", 8 pgs.
"U.S. Appl. No. 14/782,876, Response filed Jun. 16, 2017 to Non Final Office Action dated Feb. 16, 2017", 8 pgs.
"U.S. Appl. No. 14/782,876, Restriction Requirement dated Oct. 14, 2016", 10 pgs.
"U.S. Appl. No. 15/822,956, Final Office Action dated Sep. 23, 2019", 9 pgs.
"U.S. Appl. No. 15/822,956, Non Final Office Action dated May 8, 2019", 16 pgs.
"U.S. Appl. No. 15/822,956, Notice of Allowance dated Jun. 1, 2020", 5 pgs.
"U.S. Appl. No. 15/822,956, Notice of Allowance dated Dec. 18, 2019", 8 pgs.
"U.S. Appl. No. 15/822,956, Preliminary Amendment filed Nov. 27, 2017", 3 pgs.
"U.S. Appl. No. 15/822,956, Response filed Apr. 8, 19 to Restriction Requirement dated Feb. 7, 2019", 6 pgs.
"U.S. Appl. No. 15/822,956, Response Filed Nov. 22, 2019 to Final Office Action dated Sep. 23, 2019", 8 pgs.
"U.S. Appl. No. 15/822,956, Response filed Aug. 8, 2019 to Non-Final Office Action dated May 8, 2019", 9 pgs.
"U.S. Appl. No. 15/822,956, Restriction Requirement dated Feb. 7, 2019", 9 pgs.

(56) References Cited

OTHER PUBLICATIONS

"U.S. Appl. No. 15/822,956, Supplemental Preliminary Amendment filed Apr. 23, 2018", 9 pgs.
"U.S. Appl. No. 16/076,219, Final Office Action dated Oct. 7, 2021", 9 pgs.
"U.S. Appl. No. 16/076,219, Non Final Office Action dated May 7, 2021", 19 pgs.
"U.S. Appl. No. 16/076,219, Notice of Allowability dated Sep. 19, 2022", 6 pgs.
"U.S. Appl. No. 16/076,219, Notice of Allowance dated Jan. 25, 2022", 10 pgs.
"U.S. Appl. No. 16/076,219, Notice of Allowance dated Aug. 2, 2022", 6 pgs.
"U.S. Appl. No. 16/076,219, Response filed Apr. 6, 2021 to Restriction Requirement dated Feb. 5, 2021", 7 pgs.
"U.S. Appl. No. 16/076,219, Response filed Sep. 7, 2021 to Non Final Office Action dated May 7, 2021", 8 pgs.
"U.S. Appl. No. 16/076,219, Response filed Dec. 7, 2021 to Final Office Action dated Oct. 7, 2021", 6 pgs.
"U.S. Appl. No. 16/076,219, Restriction Requirement dated Feb. 5, 2021", 8 pgs.
"U.S. Appl. No. 16/304,064, Final Office Action dated Aug. 26, 2022", 21 pgs.
"U.S. Appl. No. 16/304,064, Non Final Office Action dated Jan. 6, 2022", 23 pgs.
"U.S. Appl. No. 16/304,064, Response filed May 6, 2022 to Non Final Office Action dated Jan. 6, 2022", 8 pgs.
"U.S. Appl. No. 16/304,064, Response filed Oct. 6, 2021 to Restriction Requirement dated Aug. 6, 2021", 9 pgs.
"U.S. Appl. No. 16/304,064, Response filed Nov. 18, 2022 to Final Office Action dated Aug. 26, 2022", 7 pgs.
"U.S. Appl. No. 16/304,064, Restriction Requirement dated Aug. 6, 2021", 7 pgs.
"U.S. Appl. No. 16/477,762, Non Final Office Action dated Jan. 27, 2021", 13 pgs.
"U.S. Appl. No. 16/477,762, Notice of Allowability dated Jun. 28, 2021", 3 pgs.
"U.S. Appl. No. 16/477,762, Notice of Allowance dated Jun. 10, 2021", 8 pgs.
"U.S. Appl. No. 16/477,762, Preliminary Amendment filed Jul. 12, 2019", 8 pgs.
"U.S. Appl. No. 16/477,762, Response filed Apr. 27, 2021 to Non Final Office Action dated Jan. 27, 2021", 8 pgs.
"U.S. Appl. No. 16/477,762, Response filed Oct. 7, 2020 to Restriction Requirement dated Aug. 25, 2020", 8 pgs.
"U.S. Appl. No. 16/477,762, Restriction Requirement dated Aug. 25, 2020", 12 pgs.
"U.S. Appl. No. 16/980,268, Preliminary Amendment filed Sep. 11, 2020", 7 pgs.
"U.S. Appl. No. 17/470,560, Preliminary Amendment filed Feb. 2, 2022", 6 pgs.
"U.S. Appl. No. 17/603,831, Preliminary Amendment filed Oct. 14, 2021", 7 pgs.
"U.S. Appl. No. 17/603,840, Preliminary Amendment filed Oct. 14, 2021", 7 pgs.
"Australia Application No. 2006332728, Examiner's Report dated Jun. 6, 2011", 2 pgs.
"Australia Application Serial No. 2005243221 Examiner Report dated Dec. 10, 2009", 3 pgs.
"Australian Application No. 58694/00, Response filed Oct. 28, 2004 to Examiner's Report dated Nov. 26, 2003", 20 pgs.
"Australian Application Serial No. 2004/227358, Office Action dated Sep. 23, 2008", 4 pgs.
"Australian Application Serial No. 2004227358, Examiner Report No. 2 dated Aug. 27, 2009", 2 pgs.
"Australian Application Serial No. 2004227358, Response filed Jul. 10, 2009 to Examiner's First Report dated Sep. 23, 2008", 10 pgs.
"Australian Application Serial No. 2004227358, Response filed Oct. 22, 2009 to Examiner's Second Report dated Aug. 27, 2009", 16 pgs.
"Australian Application Serial No. 2004227915, Examiner Report dated Dec. 5, 2008", 2 pgs.
"Australian Application Serial No. 2006202785, Examiner's First Report dated Sep. 21, 2007", 3 pgs.
"Australian Application Serial No. 2006202785, Response filed Sep. 19, 2008 to Examiner's First Report dated Sep. 21, 2007", 29 pgs.
"Australian Application Serial No. 2006332728, Response filed Nov. 14, 2011 to Examiner Report dated Jun. 6, 2011", 12 pgs.
"Australian Application Serial No. 2006332728, Subsequent Examiner Report dated Nov. 24, 2011", 2 pgs.
"Australian Application Serial No. 2014251099, First Examination Report dated May 30, 2018", 4 pgs.
"Australian Application Serial No. 2014251099, Response filed Dec. 19, 2018 to Examiner's Report dated May 30, 2018", 39 pgs.
"Australian Application Serial No. 2020289851, First Examination Report dated Aug. 8, 2022", 4 pgs.
"Australian Application Serial No. 40192/99, Response filed Dec. 10, 2002 to Examiner's First Report dated May 24, 2002", 15 pgs.
"Australian Application Serial No. 58694/00, Examiner Report No. 2 dated Nov. 18, 2004", 3 pgs.
"Australian Application Serial No. 58694/00, Examiner's Report dated Jul. 18, 2005", 2 pgs.
"Australian Application Serial No. 58694/00, Response filed Jul. 7, 2005 to Examiner's Report dated Nov. 18, 2004", 15 pgs.
"Australian Application Serial No. 80032/00, First Examiner's Report dated May 19, 2004", 2 pgs.
"Australian Application Serial No. 80032/00, Response filed Feb. 2, 2006 to Second Examiner's Report dated Jan. 3, 2006", 56 pgs.
"Australian Application Serial No. 80032/00, Response filed Dec. 8, 2005 to First Examiner's Report dated May 19, 2004", 36 pgs.
"Australian Application Serial No. 80032/00, Second Examiner's Report dated Jan. 3, 2006", 3 pgs.
"Brazilian Application Serial No. 1120210207082, Office Action dated Dec. 22, 2021", with machine translation, 2 pgs.
"Brazilian Application Serial No. 1120210207082, Response filed Feb. 25, 2022 to Office Action dated Dec. 22, 2021", with machine translation, 4 pgs.
"Calbichem(r) Eicosapentaenoic Acid, EPA; 20:5 w-3; 5,8, 11, 14, 17-Eicosapentaenoic Acid", Catalog No. 324875, (Dec. 7, 1998), 2 pgs.
"Calbiochem(r) MG-132, Carbobenzoxy-L-leucyl-L-leucinal", Catalog No. 474790, (Oct. 15, 1999), 2 pgs.
"Calbiochem(r) Simvastatin, MK-733", Catalog No. 567020, (Oct. 25, 2001), 2 pgs.
"Calbiochem(r) Aminoglycoside antibiotic. Inhibits myeloperoxidase-dependent oxidant cell injury", Tobramycin, Free Base, Catalog No. 614005, (Aug. 26, 1999), 1 pg.
"Calbiochem(r) Camptothecin, Camptotheca acuminata (S)-(+)-Camptothecin; 4-Ethyl-4-hydroxy-1H-pyrano[3', 4': 6,7] indolizino [1,2-b] quinoline-3, 14 (4H, 12H) dione", Catalog No. 208925, (Oct. 2, 2000), 2 pgs.
"Calbiochem(r) Doxorubicin, Hydrochloride Adriamycin; 14-Hydroxydaunomycin, HCl", Catalog No. 324380, (Oct. 21, 1998), 2 pgs.
"Canadian Application Serial No. 2,328,447, Official Action dated Feb. 7, 2005", 2 pgs.
"Canadian Application Serial No. 2,328,447, Response filed Aug. 8, 2005 to Official Action dated Feb. 7, 2005", 15 pgs.
"Canadian Application Serial No. 2,376,400, Office Action dated Apr. 7, 2008", 4 pgs.
"Canadian Application Serial No. 2,376,400, Official Action dated Jan. 5, 2010", 3 pgs.
"Canadian Application Serial No. 2,376,400, Official Action dated Apr. 7, 2008", 4 pgs.
"Canadian Application Serial No. 2,376,400, Response filed Oct. 7, 2008 to Official Action dated Apr. 7, 2008", 49 pgs.
"Canadian Application Serial No. 2,376,400, Response filed Oct. 7, 2008 to Office Action dated Apr. 7, 2008", 49 pgs.
"Canadian Application Serial No. 2,386,546, Office Action dated Jun. 30, 2009", 4 pgs.
"Canadian Application Serial No. 2,520,028, Office Action dated Jan. 19, 2011", 3 pgs.

(56) References Cited

OTHER PUBLICATIONS

"Canadian Application Serial No. 2,634,670 , Response filed Sep. 30, 2013 to Office Action dated May 17, 2013", 53 pgs.
"Canadian Application Serial No. 2,634,670, Office Action dated Feb. 3, 2014", 3 pgs.
"Canadian Application Serial No. 2,634,670, Office Action dated Feb. 17, 2015", 6 pgs.
"Canadian Application Serial No. 2,634,670, Office Action dated May 17, 2013", 4 pgs.
"Canadian Application Serial No. 2,634,670, Voluntary Amendment and Submission of Sequence Listing filed Dec. 24, 2008", 19 pgs.
"Canadian Application Serial No. 2,634,670, Voluntary Amendment filed Dec. 20, 2011", 7 pgs.
"Canadian Application Serial No. 2,909,085, Office Action dated Feb. 16, 2021", 4 pgs.
"Canadian Application Serial No. 2,909,085, Office Action dated Feb. 17, 2022", 3 pgs.
"Canadian Application Serial No. 2,909,085, Office Action dated Apr. 2, 2020", 5 pgs.
"Canadian Application Serial No. 2,909,085, Response filed Jun. 11, 2021 to Office Action dated Feb. 16", 77 pgs.
"Canadian Application Serial No. 2,909,085, Response filed Jul. 30, 2020 to Office Action dated Apr. 2, 2020", 29 pgs.
"Canadian Application Serial No. 2,909,085, Response Filed Aug. 26, 2022 to Office Action dated Feb. 17, 2022", 12 pages.
"Canadian Application Serial No. 2,909,085, Voluntary Amendment Filed Sep. 6, 2019", 4 pgs.
"Canadian Application Serial No. 2386546, Response filed Oct. 14, 2008 to Office Action dated Apr. 14, 2008", 20 pgs.
"Canadian Application Serial No. 2386546,, Office Action dated Apr. 14, 2008", 3 pgs.
"Canadian Application Serial No. 3,016,985, Response Filed Apr. 7, 22 to Office Action dated Oct. 8, 2021", 11 pgs.
"Canadian Application Serial No. 3,016,985, Voluntary Amendment filed Apr. 12, 2022", 12 pgs.
"Canadian Application Serial No. 3,174,963, Voluntary Amendment Filed Sep. 29, 2022", 10 pgs.
"Cancer Research", Contribution to Society, http://www.bikaken.or.jp/mcrf_e/contributiion, (Dec. 4, 2000), 2 pages.
"Carbiochem(r) Lovastatin, Mevinolin; MK-803", Catalolg No. 438185, (Jun. 29, 2001), 2 pgs.
"Chilean Application Serial No. 202102701, Acceptance to Continue Prosecution mailed Oct. 19, 22", w/o English Translation, 1 pg.
"Chinese Application Serial No. 201480032420.6, Office Action dated May 3, 2017", w/English Translation of Claims, 20 pgs.
"Chinese Application Serial No. 201480032420.6, Office Action dated Jul. 13, 2018", w/English translation, 8 pgs.
"Chinese Application Serial No. 201480032420.6, Office Action dated Dec. 14, 2017", (English Translation), 8 pgs.
"Chinese Application Serial No. 201480032420.6, Response filed Feb. 27, 2018 to Office Action dated Dec. 14, 2017", w/Amended Claims, 73 pgs.
"Chinese Application Serial No. 201480032420.6, Response filed Sep. 18, 2017 to Office Action dated May 3, 2017", w/English Claims, 25 pgs.
"Chinese Application Serial No. 201480032420.6, Response filed Nov. 26, 2018 to Office Action dated Jul. 13, 2018", w/ English Claims, 73 pgs.
"Chinese Application Serial No. 202080043579.3, Voluntary Amendment Filed Jul. 28, 2022", W/English Claims, 23 pgs.
"Chinese Application Serial No. 202080043595.2, Notification to Make Rectification dated Dec. 29, 2021", with machine translation, 5 pgs.
"Chinese Application Serial No. 202080043595.2, Response filed Mar. 11, 2022", with machine translation, 4 pgs.
"Chinese Application Serial No. 202080043595.2, Voluntary Amendment filed Oct. 8, 2022", with English claims, 13 pgs.
"DNA Vector-Based siRNA", http://www.genscript.com/rnai_intro.html, (observed Mar. 9, 2004), 3 pgs.

"Drugs for Selection of Genetic Markers Reagents for positive and negative selection of Genes involved in Nucleotide Metabolism", Calbiochem, (Mar. 2002), 6 pages.
"Enzyme database entry for EC No. 3.4.22", ,, [online}. Retrieved from the Internet: <http://ca.expasy.org/enzyme/3.4.22>, (Jun. 19, 2007), 2 pgs.
"Epoxomicin—a potent and selective proteasome inhibitor", Affiniti Research Products Limited, 2 pages.
"Eurasian Application Serial No. 201892006, Office Action dated Apr. 29, 2022", w/ English translation, 7 pgs.
"Eurasian Application Serial No. 201892006, Response Filed Aug. 29, 2022 to Office Action dated Apr. 29, 2022", W/ English Claims, 9 pgs.
"European Application Serial No. 05778984.4, Office Action dated Jul. 20, 2007", 2 pgs.
"European Application Serial No. 005778984.4, Response filed Mar. 4, 2008 to Communication dated Jul. 20, 2007", 28 pgs.
"European Application Serial No. 00944624.6, Main Request, First Auxiliary Request and Second Auxiliary Request filed Sep. 29, 2008", 67 pgs.
"European Application Serial No. 00944624.6, Office Action dated Aug. 5, 2003", 3 pgs.
"European Application Serial No. 00944624.6, Office Action dated Mar. 4, 2005", 5 pgs.
"European Application Serial No. 00944624.6, Response and Further Auxiliary Requests filed Oct. 27, 2008 to Primary Examiner's Telephonic Comments", 122 pgs.
"European Application Serial No. 00944624.6, Response filed Feb. 16, 2004 to Office Action dated Aug. 5, 2003", 25 pgs.
"European Application Serial No. 00944624.6, Response filed Aug. 26, 2005 to Office Action dated Mar. 4, 2005", 31 pgs.
"European Application Serial No. 00970689.6, Communication dated Nov. 19, 2003", 4 pgs.
"European Application Serial No. 00970689.6, Communication dated Dec. 19, 2005", 7 pgs.
"European Application Serial No. 00970689.6, Office Action dated Sep. 13, 2007", 5 pgs.
"European Application Serial No. 00970689.6, Office Action dated Dec. 29, 2008", 5 pgs.
"European Application Serial No. 00970689.6, Response filed Apr. 24, 2008 to Communication dated Sep. 13, 2007", 39 pgs.
"European Application Serial No. 00970689.6, Response filed Aug. 9, 2004 to Communication dated Nov. 19, 2003", 10 pgs.
"European Application Serial No. 00970689.6, Response dated Jul. 27, 2006 to Examination Report dated Dec. 19, 2005", 51 pgs.
"European Application Serial No. 02749934.2, Communication dated Mar. 12, 2004", 2 pgs.
"European Application Serial No. 02749934.2, Communication dated Nov. 12, 2004", 3 pgs.
"European Application Serial No. 02749934.2, Response filed Jan. 7, 2005 to Communication dated Nov. 12, 2004", 1 pg.
"European Application Serial No. 02749934.2, Response filed Apr. 21, 2004 to Communication dated Mar. 12, 2004", 9 pgs.
"European Application Serial No. 04749597.3, Communication dated May 13, 2008", 5 pgs.
"European Application Serial No. 04749597.3, Office Action dated Nov. 20, 2006", 3 pgs.
"European Application Serial No. 04749597.3, Office Action dated Mar. 28, 2006", 9 pgs.
"European Application Serial No. 04749597.3, Office Action Received dated May 13, 2008", 5 pgs.
"European Application Serial No. 04749597.3, Response filed Sep. 6, 2007 to Office Action dated Nov. 20, 2006", 6 pgs.
"European Application Serial No. 04749597.3, Response filed Oct. 6, 2006 to Office Action dated Mar. 28, 2006", 28 pgs.
"European Application Serial No. 04749619.5 Office Action dated Nov. 9, 2009", 3 pgs.
"European Application Serial No. 04749619.5, Communication dated Apr. 14, 2008", 5 pgs.
"European Application Serial No. 04749619.5, Communication dated Sep. 13, 2007", 1 pg.
"European Application Serial No. 04749619.5, Communication Noting Loss of Rights dated Nov. 28, 2008", 1 pg.

(56) References Cited

OTHER PUBLICATIONS

"European Application Serial No. 04749619.5, Office Action dated Mar. 11, 2009", 4 pgs.
"European Application Serial No. 04749619.5, Office Action dated Mar. 28, 2006", 8 pgs.
"European Application Serial No. 04749619.5, Office Action dated Nov. 20, 2006", 4 pgs.
"European Application Serial No. 04749619.5, Response filed Feb. 6, 2009 to Communication dated Nov. 28, 2008", 14 pgs.
"European Application Serial No. 04749619.5, Response filed Sep. 7, 2007 to Office Action dated Nov. 20, 2006", 28 pgs.
"European Application Serial No. 04749619.5, Response filed Sep. 21, 2009 to Office Action dated Mar. 11, 2009", 19 pgs.
"European Application Serial No. 04749619.5, Response filed Oct. 4, 2007 to Communication dated Sep. 13, 2007", 3 pgs.
"European Application Serial No. 04749619.5, Response filed Oct. 17, 2006 to Office Action dated Mar. 28, 2006", 17 pgs.
"European Application Serial No. 04749619.5, Summons to Attend Oral Proceedings mailed Jun. 16, 2010", 5 pgs.
"European Application Serial No. 05778984.4, Invitation pursuant to Article 94(3) dated Aug. 28, 2008", 5 pgs.
"European Application Serial No. 05778984.4, Response filed Feb. 26, 2009 to Communication dated Aug. 28, 2008", 21 pgs.
"European Application Serial No. 06849005.1, Office Action dated Apr. 21, 2010", 10 Pgs.
"European Application Serial No. 06849005.1, Office Action dated May 15, 2009", 4 pgs.
"European Application Serial No. 06849005.1, Response filed Jan. 17, 2012 to Summons mailed Nov. 14, 2011", 13 pgs.
"European Application Serial No. 06849005.1, Response filed Aug. 1, 2011 to Office Action dated Mar. 22, 2011", 16 pgs.
"European Application Serial No. 06849005.1, Response filed Nov. 1, 2010 to Office Action dated Apr. 21, 2010", 17 pgs.
"European Application Serial No. 06849005.1, Response filed Nov. 24, 2009 tp Office Action dated May 15, 2009", 16 pgs.
"European Application Serial No. 06849005.1, Summons mailed Nov. 14, 2011", 16 pgs.
"European Application Serial No. 07075464.3, Office Action dated May 7, 2008", 6 pgs.
"European Application Serial No. 07075464.3, Office Action dated Sep. 29, 2009", 8 pgs.
"European Application Serial No. 07075464.3, Partial European Search Report dated Oct. 2, 2007", 13 pgs.
"European Application Serial No. 07075464.3, Response filed Feb. 26, 2009 to Communication dated May 7, 2008", 12 pgs.
"European Application Serial No. 14783418.8, Communication Pursuant to Article 94(3) EPC dated Mar. 27, 2018", 4 pgs.
"European Application Serial No. 14783418.8, Extended European Search Report dated Feb. 27, 2017", 15 pgs.
"European Application Serial No. 14783418.8, Response filed May 26, 2016", 13 pgs.
"European Application Serial No. 14783418.8, Response filed May 30, 2018 to Communication Pursuant to Article 94(3) EPC dated Mar. 27, 2018", 271 pgs.
"European Application Serial No. 14783418.8, Response filed Sep. 22, 2017", 11 pgs.
"European Application Serial No. 17712339.5, Communication Pursuant to Article 94(3) EPC dated May 12, 2022", 4 pgs.
"European Application Serial No. 17712339.5, Response Filed Sep. 15, 2022 to Communication Pursuant to Article 94(3) EPC dated May 12, 2", 10 pgs.
"European Application Serial No. 20727413.5, Response Filed Jun. 20, 2022 to Communication Pursuant to Rules 161(1) and 162 EPC dated Dec. 9, 2021", 10 pgs.
"European Application Serial No. 20728248.4, Response Filed Jun. 20, 2022 to Communication Pursuant to Rules 161(1) and 162 EPC dated Jan. 26, 2022", 9 pgs.
"European Application Serial No. 99924404.9, Communication Pursuant to Article 96(2) EPC dated Feb. 27, 2006", 3 pgs.
"European Application Serial No. 99924404.9, Communication Pursuant to Article 96(2) dated Jun. 18, 2003", 3 pgs.
"European Application Serial No. 99924404.9, EP Communication Pursuant to Article 96(2) EPC dated Oct. 7, 2004", 3 pgs.
"European Application Serial No. 99924404.9, Response filed Apr. 8, 2004 to Communication dated Feb. 3, 2004", 13 pgs.
"European Application Serial No. 99924404.9, Response filed Apr. 15, 2005 to Communication dated Oct. 7, 2004", 23 pgs.
"European Application Serial No. 99924404.9, Response filed Jun. 22, 2006 to Communication dated Feb. 27, 2006", 1 pg.
"European Application Serial No. EP 07075464, Partial European Search Report dated Sep. 19, 2007", 12 pgs.
"European Application Serial No. 06849005.1, Office Action dated Mar. 22, 2011", 11 Pgs.
"Indian Application Serial No. 10078/DELNP/2015, First Examination Report dated Mar. 12, 2020", w/ English Translation, 8 pgs.
"International Application Serial No. PCT/US 00/15700, International Search Report dated Dec. 21, 2000", 9 pgs.
"International Application Serial No. PCT/US 00/15700, Written Opinion dated Aug. 1, 2001", 7 pgs.
"International Application Serial No. PCT/US00/15700, International Preliminary Examination Report dated Sep. 20, 2001", 7 pgs.
"International Application Serial No. PCT/US00/27863, International Search Report dated Mar. 19, 2001", 8 pgs.
"International Application Serial No. PCT/US00/27863, Written Opinion dated Sep. 24, 2001", 7 pgs.
"International Application Serial No. PCT/US02/21926, International Search Report dated Sep. 11, 2003", 8 pgs.
"International Application Serial No. PCT/US02/21926, Written Opinion dated Jul. 14, 2004", 5 pgs.
"International Application Serial No. PCT/US2004/009950, International Preliminary Report on Patentability dated Mar. 31, 2003", 15 pgs.
"International Application Serial No. PCT/US2004/009950, International Preliminary Report on Patentability dated Oct. 13, 2005", 15 pgs.
"International Application Serial No. PCT/US2004/009950, International Search Report dated Mar. 8, 2005", 8 pgs.
"International Application Serial No. PCT/US2004/009950, Written Opinion dated Mar. 8, 2005", 15 pgs.
"International Application Serial No. PCT/US2004/010045, International Preliminary Report on Patentability dated Oct. 13, 2005", 14 pgs.
"International Application Serial No. PCT/US2004/010045, International Search Report dated Jan. 10, 2005", 6 pgs.
"International Application Serial No. PCT/US2004/010045, Written Opinion dated Jan. 10, 2005", 15 pgs.
"International Application Serial No. PCT/US2005/015315, International Search Report dated Feb. 2, 2007", 7 pgs.
"International Application Serial No. PCT/US2005/015315, International Search Report dated Feb. 7, 2007", 7 pgs.
"International Application Serial No. PCT/US2005/015315, Invitation to Pay Additional Fees and Partial Search Reportt", 6 pgs.
"International Application Serial No. PCT/US2005/015315, Written Opinion dated Feb. 7, 2007", 10 pgs.
"International Application Serial No. PCT/US2006/049424, International Preliminary Report on Patentability dated Jul. 10, 2008", 17 pgs.
"International Application Serial No. PCT/US2006/049424, International Search Report dated Nov. 26, 2007", 11 pgs.
"International Application Serial No. PCT/US2006/049424, Written Opinion dated Nov. 26, 2007", 17 pgs.
"International Application Serial No. PCT/US2007/010434, International Search Report dated Oct. 10, 2007", 11 pgs.
"International Application Serial No. PCT/US2007/010434, International Search Report dated Dec. 5, 2007", 11 pgs.
"International Application Serial No. PCT/US2007/010434, Written Opinion dated Dec. 5, 2007", 19 pgs.
"International Application Serial No. PCT/US2014/033343, International Preliminary Report on Patentability dated Oct. 13, 2015", 12 pgs.
"International Application Serial No. PCT/US2014/033343, International Search Report dated Sep. 2, 2014", 4 pgs.

(56) References Cited

OTHER PUBLICATIONS

"International Application Serial No. PCT/US2014/033343, Written Opinion dated Sep. 2, 2014", 10 pgs.
"International Application Serial No. PCT/US2017/017021, International Preliminary Report on Patentability dated Aug. 23, 2018", 12 pgs.
"International Application Serial No. PCT/US2017/017021, International Search Report dated May 23, 2017", 8 pgs.
"International Application Serial No. PCT/US2017/017021, Written Opinion dated May 23, 2017", 10 pgs.
"International Application Serial No. PCT/US2017/034678, International Preliminary Report on Patentability dated Dec. 6, 2018", 9 pgs.
"International Application Serial No. PCT/US2017/034678, International Search Report dated Oct. 16, 2017", 7 pgs.
"International Application Serial No. PCT/US2017/034678, Written Opinion dated Oct. 16, 2017", 6 pgs.
"International Application Serial No. PCT/US2018/013634, International Preliminary Report on Patentability dated Jul. 25, 2019", 12 pgs.
"International Application Serial No. PCT/US2018/013634, International Search Report dated Jun. 18, 2018", 9 pgs.
"International Application Serial No. PCT/US2018/013634, Invitation to Pay Add'l Fees and Partial Search Report dated Apr. 17, 2018", 14 pgs.
"International Application Serial No. PCT/US2018/013634, Written Opinion dated Jun. 18, 2018", 12 pgs.
"International Application Serial No. PCT/US2019/022106, International Preliminary Report on Patentability dated Sep. 24, 2020", 10 pgs.
"International Application Serial No. PCT/US2019/022106, International Search Report dated Sep. 12, 2019", 8 pgs.
"International Application Serial No. PCT/US2019/022106, Invitation to Pay Additional Fees dated Jul. 17, 2019", 10 pgs.
"International Application Serial No. PCT/US2019/022106, Written Opinion dated Sep. 12, 2019", 8 pgs.
"International Application Serial No. PCT/US2020/028264, International Preliminary Report on Patentability dated Oct. 28, 2021", 10 pgs.
"International Application Serial No. PCT/US2020/028264, International Search Report dated Aug. 5, 2020", 7 pgs.
"International Application Serial No. PCT/US2020/028264, Written Opinion dated Aug. 5, 2020", 8 pgs.
"International Application Serial No. PCT/US2020/028269, International Preliminary Report on Patentability dated Oct. 28, 2021", 9 pgs.
"International Application Serial No. PCT/US2020/028269, International Search Report dated Aug. 7, 2020", 7 pgs.
"International Application Serial No. PCT/US2020/028269, Written Opinion dated Aug. 7, 2020", 7 pgs.
"International Application Serial No. PCT/US2021/039860, International Search Report dated Jan. 24, 2022", 12 pgs.
"International Application Serial No. PCT/US2021/039860, Invitation to Pay Additional Fees dated Nov. 29, 2021", 20 pgs.
"International Application Serial No. PCT/US2021/039860, Written Opinion dated Jan. 24, 2022", 15 pgs.
"International Application Serial No. PCT/US99/11197, International Search Report dated Sep. 22, 1999", 9 pgs.
"International Application Serial No. PCT/US99/11197, Written Opinion dated Mar. 13, 2000", 11 pgs.
"Israel Application Serial No. 241954, Office Action dated Oct. 9, 2018", W/English Translation, 10 pgs.
"Israel Application Serial No. 241954, Office Action dated Dec. 5, 2019", w/ English Translation, 6 pgs.
"Israel Application Serial No. 241954, Response filed Feb. 7, 2019 to Office Action dated Oct. 9, 2018", wZ English Translation, 14 pgs.
"Israel Application Serial No. 261642, Notification of Defects in Patent Application dated Dec. 26, 2021", w/ English Translation, 8 pgs.

"Israeli Application Serial No. 261642, Response Filed Apr. 25, 2022 to Notification of Defects in Patent Application dated Dec. 26, 2021", W/ English Claims, 7 pgs.
"Japanese Application Serial No. 2000-549752, Notice of Rejection dated Feb. 10, 2009", (w/ English Translation), 10 pgs.
"Japanese Application Serial No. 2001-501645, Office Action dated Jun. 8, 2010", With English Claims, 4 pgs.
"Japanese Application Serial No. 2001-501645, Office Action Response Filed Dec. 7, 2010", w/ English claims, 8 pgs.
"Japanese Application Serial No. 2001-528616, Office Action dated Jun. 8, 2010", with English translation, 7 pgs.
"Japanese Application Serial No. 2006-509588, Office Action dated Mar. 2, 2010", With English Translation, 14 pgs.
"Japanese Application Serial No. 2008-548723, Office Action dated Apr. 3, 2012", (wZ English Translation), 9 pgs.
"Japanese Application Serial No. 2016-507610, Notification of Reasons for Refusal dated Jan. 24, 2019", wZ English translation, 6 pgs.
"Japanese Application Serial No. 2016-507610, Office Action dated Feb. 21, 2018", with English translation of claims, 16 pgs.
"Japanese Application Serial No. 2016-507610, Response filed Mar. 6, 2019 to Notification of Reasons for Refusal dated Jan. 24, 2019", with machine Translation, 10 pgs.
"Japanese Application Serial No. 2016-507610, Response filed Aug. 21, 2018 to Office Action dated Feb. 21, 2018", with English translation of claims, 27 pgs.
"Japanese Application Serial No. 2021-561893, Notification of Reasons for Refusal dated Nov. 1, 2022", w/ English Translation, 10 pgs.
"Japanese Application Serial No. 501645/01—Final Rejection filed Sep. 6, 2011", w/English translation, 6 pgs.
"Japanese Application Serial No. 501645/01, Preliminary Amendment filed May 31, 2007", w/English claims, 12 pgs.
"Japanese Application Serial No. 501645/01, Response filed Jan. 10, 2012 to Final Office Action dated Sep. 29, 2011", w/ English claims, 11 pgs.
"Japanese Application Serial No. 509588/06, Final Office Action dated Nov. 16, 2010", 1 pg.
"Japanese Application Serial No. JP2006-509588, Amended Claims filed Mar. 22, 2007", (w/ English Translation of Claims), 28 pgs.
"LDP-341", Millennium Pharmaceuticals, http://www.biospace.com/ct/detail.cfm?ClinicalID=266404, (Jul. 18, 2001), 1 page.
"Mexican Application Serial No. MX/a/2018/010842, Office Action dated May 13, 2022", with machine translation, 9 pgs.
"Mexican Application Serial No. MX/a/2018/010842, Response Filed Sep. 19, 2022 to Office Action dated May 13, 2022", W/ English Claims, 18 pgs.
"Mexican Application Serial No. MX/a/2021/012681, Office Action dated Nov. 16, 2021", with machine translation, 9 pgs.
"Mexican Application Serial No. MX/a/2021/012681, Response filed Mar. 9, 2022", with machine translation, 129 pgs.
"Mexican Application Serial No. MX/a/2021/012681, Voluntary Amendment filed Apr. 19, 2022", with English translation of claims, 10 pgs.
"Mexican Application Serial No. MX/a/2021/012682, Voluntary Amendment filed Apr. 19, 2022", with English translation of claims, 10 pgs.
"New Zealand Application Serial No. 713509, First Examiner Report dated Nov. 14, 2019", 7 pgs.
"PCT Application Serial No. PCT/US2005/015315, International Preliminary Report on Patentability, and Written Opinion, dated Feb. 28, 2007", 11 pages.
"Polymer Vectors Endosomal release and cytoplasmic delivery", Endosomal Release, http://web.bham.ac.uk/can4psd4/nonviral/endosome.html, (Jun. 3, 2001), 1 pg.
"Product Data Sheet", Moravek Biochemicals, Inc., M-1535, Ritonavir, (Jul. 12, 2001), 1 page.
"Product Information", Sigma, Cyclosporin A, Sigma Product No. C3662, (Oct. 28, 1996), 3 pages.
"Product Information", Sigma, Bleomycin Sulfate, Sigma Prod. No. B5507, (Nov. 25, 1996), 2 pages.
"Proteasome Inhibitors", Peptides International, Inc., (Apr. 16, 2001), 1-2.

(56) References Cited

OTHER PUBLICATIONS

"Singapore Application Serial No. 11202111334S, Voluntary Amendment filed Apr. 27, 2022", 10 pgs.
"Singaporean Application Serial No. 11202111353Q, Response Filed May 11, 2022 to Request for Examination Notice dated Apr. 4, 2022", W/ English Claims, 18 pgs.
"South African Application Serial No. 2015/07946, Voluntary Amendment filed Jul. 24, 2020", 21 pgs.
"Tannic Acid, A.C.S. reagent", Sigma, www.sigma-aidrich.com/sacatolog.nsf/productlookup/Aldrich403040?OpenDocument, (Jan. 20, 2001), 1 page.
"Vietnamese Application Serial No. 1-2021-07262, Office Action dated Sep. 13, 2022", w/English translation, 2 pgs.
"Vietnamese Application Serial No. 1-2021-07263, Office Action dated Sep. 13, 2022", w/English translation, 2 pgs.
Abe, Y, et al., "Cytotoxic mechanisms by M239V presenilin 2, a little-analyzed Alzheimer's disease-causative mutant", J. Neurosci Res. 77(4), Abstract Only, (Aug. 2004), 583-95.
Abramov, A. Y, et al., "Beta-amyloid peptides induce mitochondrial dysfunction and oxidative stress in astrocytes and death of neurons through activation of NADPH oxidase.", J Neurosci., 24(2), (Jan. 14, 2004), 565-75.
Abramov, A. Y., et al., "The role of an astrocytic NADPH oxidase in the neurotoxicity of amyloid beta peptides", Philosophical Transactions of The Royal Society B, 360, (2005), 2309-2314.
Adams, J., et al., "Proteasome inhibition: a new strategy in cancer treatment.", Invest New Drugs, 18(2), (May 2000), 109-21.
Adams, Julian, et al., "Chapter 28. Novel Inhibitors of the Proteasome and Their Theraputic Use in Inflammation", Annual Reports in Medicinal Chemistry, Academic Press, Inc., (1996), 279-288.
Adams, Julian, "Proteasome inhibition: a novel approach to cancer therapy", Trends in Molecular Medicine, 8(4), (2002), S49-S54.
Afione, S. A., et al., "In Vivo Model of Adeno-Associated Virus Vector Persistence and Rescue", Journal of Virology, 70(5), (May 1996), 3235-3241.
Alavijeh, Mohammad S, et al., "Drug Metabolism and Pharmacokinetics, the Blood-Brain Barrier, and Central Nervous Systems Drug Discovery", The Journal of the American Societ for Experimental NeuroTherapeutics vol. 2, (Oct. 2005), 554-571.
Alberts, B., et al., "Chapter 13, pp. 618-626", In: Molecular Biology of the Cell, 3rd edition, (1994), 11 pgs.
Alexander, I E., et al., "Effects of Gamma Irradiation on the Transduction of Dividing and Nondividing Cells in Brain and Muscle of Rats by Adeno-Associated Virus Vectors", Human Gene Therapy, 7(7), (May 1, 1996), 841-850.
Alexander, Ian E., et al., "DNA-Damaging Agents Greatly Increase the Transduction of Nondividing Cells by Adeno-Associated Virus Vectors", Journal of Virology, 68(12), (Dec. 1994), 8282-8287.
Ali, R. R., et al., "Gene transfer into the mouse retina mediated by an adeno-associated viral vector", Human Molecular Genetics, 5 (5), (1996), 591-594.
Allander, Tobias, et al., "Cloning of a human parvovirus by molecular screening of respiratory tract samples", PNAS, 102(36), (2005), 12891-12896.
Almond, J. B., et al., "The proteasome: a novel target for cancer chemotherapy", Leukemia, 16, (2002), 443-443.
Andre, Patrice, et al., "An inhibitor of HIV-1 protease modulates proteasome activity, antigen presentation, and T cell responses.", Proc Natl Acad Sci U S A., 95(22), (Oct. 27, 1998), 13120-13124.
Arcamone, F M, "From the Pigments of the Actinomycetes to Third Generation Antitumor Anthracyclines", Biochimie (Paris), 80(3), (Mar. 1998), 201-206.
Arnold, John, et al., "Human Bocavirus Prevalence and Clinical Spectrum at a Childrens Hospital", Clin Infect Dis. 43, (2006), 283-288.
Audige, A., et al., "Epithelial sodium channel (ENaC) subunit mRNA and protein expression in rats with puromycin aminonucleoside-induced nephrotic syndrome.", Clincial Sci., 104(4), (2003), 389-395.

Auerbach, S. D., et al., "Human Amiloride-Sensitive Epithelial Na+ Channel y Subunit Promoter: Functional Analysis and Identification of a Polypurine-Polypyrimidine Tract with the Potential for Triplex DNA Formation", Biochem. J., 347, (2000), 105-114.
Baines, D. L., et al., "Effect of LPS-lnduced NF-kB Activity on the Transcriptional Response of a 5' Flanking Region of the alphaENaC Gene", Experimental Biology 2003—Translating the Genome, Abstract No. 5860 (http://www.biosis-select.org/faseb/data/FASEB005860.html, (2003), 1 pg.
Banerjee, D., et al., "The Treatment of Respiratory Pseudomonas Infection in Cystic Fibrosis: What Drug and Which Way?", Drugs, 60(5), (Abstract Only), (Nov. 2000), 1 pg.
Bank, U., "Review: Peptidases and Peptidase Inhibitors in the Pathogenesis of Diseases", Cellular Peptidases in Immune Functions and Diseases 2, (Edited by Jurgen Langner, et al., Kluwer Academic / Plenum Publishers), (2000), 349-378.
Bartlett, J S., et al., "Targeted adeno-associated virus vector transduction of nonpermissive cells mediated by a bispecific F(ab'gamma)2 antibody.", Nature Biotechnology, 17, (1999), 181-186.
Bartlett, Jeffrey S., et al., "Infectious entry pathway of adeno-associated virus and adeno-associated virus vectors", Journal of Virology, 74(6), (Mar. 2000), 2777-2785.
Bartoli, M., et al., "Mannosidase I inhibition rescues the human alpha-sarcoglycan R77C recurrent mutation.", Hum Mol Genet., 17(9), (May 1, 2008), 1214-21.
Baruchel, S., et al., "The role of oxidative stress in disease progression in individuals infected by the human immunodeficiency virus.", J LeukocBiol., 52(1), (Jul. 1992), 111-4.
Basak, S, et al., "Infectious Entry Pathways for Canine Parvovirus", Virology, 186(2), (Feb. 1992), 368-376.
Bennett, J., et al., "Real-Time, Noninvasive In Vivo Assessment of Adeno-Associated Virus-Mediated Retinal Transduction", Investigative Ophthalmology & Visual Science, 38(13), (Dec. 1997), 2857-2863.
Berns, K. I., et al., "Biology of Adeno-associated Virus", In: Current Topics in Microbiology and Immunology, 218, Springer-Verlag, Berlin: R.W. Compans, et al., (Eds.), (1996), 1-23.
Berns, K. I., "Parvovirus Replication", Microbiological Reviews, 54 (3), (Sep. 1990), pp. 316-329.
Beutler, K. T., et al., "Long-Term Regulation of ENaC Expression in Kidney by Angiotensin II", Hypertension, 41, (2003), 1143-1150.
Bies, J., et al., "Oncogenic activation of c-Myb by Carboxyl-Terminal truncation leads to Decreased Proteolysis by the Ubiquitin-26S proteasome pathway", Oncogene, 14(2), Abstract, (Jan. 16, 1997), 1 page.
Billington, D., et al., "Dissection of hepatic receptor-mediated endocytic pathways using self-generated gradients of iodixanol (Optiprep).", Anal. Biochem., 258(8), (1998), 251-258.
Blits, B., et al., "Adeno-associated viral vector-mediated neurotrophin gene transfer in the injured adult rat spinal cord improves hind-limb function", Neuroscience,118(1), (2003), 271-81.
Bohenzky, R. A., et al., "Interactions Between the Termini of Adeno-Associated Virus DNA", Journal of Molecular Biology, 206, (1989), 91-100.
Bohenzky, R. A., et al., "Replication of Adeno-Associated Virus Genomes With Chimeric Termini", ICN / UCLA Symposium—Viral DNA Replication, (1987), 20 pgs.
Bohenzky, R. A., et al., "Sequence and Symmetry Requirements Wihtin the Internal Palindromic Sequences of the Adeno-Associated Virus Terminal Repeat", Virology, 166, (1988), 316-327.
Bohl, D., et al., "Control of erythropoietin delivery by doxycycline in mice after intramuscular injection of adeno-associated vector.", Blood, 92(5), (1998), 1512-1517.
Bok, D., "Gene Therapy of Retinal Dystrophies: Achievements, Challenges and Prospects", Novartis Foundation Symposium 255—Retinal Dystrophies: Functional Genomics to Gene Therapy, John Wiley & Sons, Ltd., (2004), 4-16; 177-178.
Bokkala, Shaila, et al., "Angiotensin II-induced Down-regulation of Inositol Trisphosphate Receptors in WB Rat Liver Epithelial Cells", Journal of Biological Chemistry, 272(19), (May 9, 1997), 12454-12461.

(56) References Cited

OTHER PUBLICATIONS

Bonacorsi, Stephane, et al., "Comparative in vitro activities of meropenem, imipenem, temocillin, piperacillin, and ceftazidime in combination with tobramycin, rifampin, or ciprofloxacin against Burkholderia cepacia isolates from patients with cystic fibrosis.", Antimicrobial Agents and Chemotherapy, 43(2), (Feb. 1999), 213-217.
Booth, R. E., et al., "Targeted Degradation of ENaC in Response to PKC Activation of the ERK1/2 Cascade", Am. J. Physiol. Renal Physiol., 284, (2003), F938-F947.
Brand, Stephen, et al., "Role of the proteasome in rat indomethacin-induced gastropathy", Gastroenterology, 116(4), (1999), 865-873.
Bravo, Laura, "Polyphenols: chemistry, dietary sources, metabolism, and nutritional significance", Nutrition Reviews, 56(11), (Nov. 1998), 317-333.
Brister, J. R., et al., "Rep-Mediated Nicking of the Adeno-Associated Virus Origin Requires Two Biochemical Activities, DNA Helicase Activity and Transesterification", Journal of Virology, 73(11), (1999), 9325-9336.
Brooijmans, N., et al., "Molecular Recognition and Docking Algorithms", Annu. Rev. Biophys. Biomol. Struct., vol. 32, (2003), 335-373.
Brotz, H., "The Lantibiotic Mersacidin Inhibits Peptidoglycan Biosynthesis and the Level of Transglycosylation", Eur. J. Biochem., 246(1), (1997), 193-199.
Brown, Kevin E., "The expanding range of parvoviruses which infect humans", Reviews in Medical Virology, GB, (2010), vol. 20, No. 4, (2010), 231-244.
Bruno, T., et al., "Levels of Expression of hRPB11, a core subassembly subunit of human RNA polymerase II, affect doxorubicin sensitivity and cellular differentiation", FEBS Letters 427, (1998), 241-246.
Bubien, J. K., et al., "Expression and regulation of normal and polymorphic epithelial sodium channel by human lymphocytes", J. Biol. Chem., 276(11), (2001), 8557-8566.
Buffinton, G. D, et al., "Oxidative stress in lungs of mice infected with influenza A virus", Free Radic Res Commun., 16(2), (1992), 99-110.
Bugg, C., et al., "SRI6975 Increases Adenovirus Mediated Gene Transfer Through the Apical Surface of Polarized MDCK Cell Monolayers", Cystic Fibrosis Foundation: 2000 North American CF Conference, (Nov. 2000), 1 pg.
Cai, J., et al., "Inhibition of influenza infection by glutathione.", Free Radic Biol Med., 34(7), (Apr. 1, 2003), 928-36.
Cameron, "Recent Advance in Transgenic Technology", Molec. Biol. vol. 7, (1997), 253-265.
Cantin, Andre M, et al., "Aerosolized Prolastin Suppresses Bacterial Proliferation in a Model of Chronic Pseudomonas aeruginosa Lung Infection", American Journal of Respiratory and Critical Care Medicine, vol. 160, (1999), 1130-1135.
Capecchi, M. R, "Altering the Genome by Homologous Recombination", Science, (244), (1989), 1288-1292.
Carter, B. J., et al., "Chapter 11—AAV DNA Replication, Integration, and Genetics", In: Handbook of Parvoviruses, vol. 1., Tijssen, P., Editor, CRC Press, Inc. (Boca Raton, FL), (1992), 169-226.
Carter, Brian J, "Adeno-Associated Virus Vectiors in Clinical Trials", Human Gene Therapy, 16(5), (2005), 541-550.
Carter, P. J., et al., "Adeno-Associated Viral Vectors as Gene Delivery Vehicles (Review)", International Journal of Molecular Medicine, 6(1), (2000), 17-27.
Cassivi, et al., "Transgene Expression After Adenovirus-Mediated Retransfection of Rat Lungs Is Increased and Prolonged by Transplant Immunosuppression", The Journal of Thoracic and Cardiovascular Surgery, Mosby-Year Book, Inc., St. Louis, MO, US, vol. 117, No. 1, (Jan. 1, 1999), 1-7.
Chao, H., et al., "Several Log Increase in Therapeutic Transgene Delivery by Distinct Adeno-Associated Viral Serotype Vectors", Molecular Therapy, 2(6), (2000), 619-623.

Cheung, Andrew K., et al., "Identification and molecular cloning of a novel porcine parvovirus", Archives of Virology; Official Journal of the Virology Division of the International Union of Microbiological Societies, Springer-Verlag, VI, vol. 155, No. 5, (2010), 801-806.
Chiorini, J. A., et al., "Cloning and Characterization of Adeno-Associated Virus Type 5", Journal of Virology, 73(2), (1999), 1309-1319.
Chiorini, J. A., et al., "Determination of Adeno-Associated Virus Rep68 and Rep78 Binding Sites by Random Sequence Oligonucleotide Selection", Journal of Virology, 69(11), (1995), 7334-7338.
Chiorini, J. A., et al., "Sequence Requirements for Stable Binding and Function of Rep68 on the Adeno-Associated Virus Type 2 Inverted Terminal Repeats", Journal of Virology, 68(11), (1994), 7448-7457.
Chu, Q, et al., "Binding and uptake of Cationic Lipid: pDNA Complexes by Polarized Airway Epithelial Cells", Human Gene Therapy, 10, (1999), pp. 25-36.
Chung, King-Thom, et al., "Tannis and Human Health: A Review", Critical Reviews in Food Science and Nutrition, 38(6), (1998), 421-464.
Cifuentes, M. E., et al., "Targeting reactive oxygen species in hypertension", Current Opinion in Nephrology and Hypertension, 15, (2006), 179-186.
Clark, J., et al., "A Future for Transgenic Livestock", Nature Reviews Genetics, 4, (2003), 825-833.
Clark, K. R., et al., "Recombinant Adeno-Associated Viral Vectors Mediate Long-Term Transgene Expression in Muscle", Human Gene Therapy, 8, (Apr. 10, 1997), pp. 659-669.
Conrad, C. K., et al., "Safety of single-dose administration of an adeno-associated virus (AAV)-CFTR vector in the primate lung", Gene Therapy, 3(8), (Aug. 1996), 658-668.
Cooney, Ashley, et al., "Cystic Fibrosis Gene Therapy: Looking Back, Looking Forward", GENES, vol. 9, No. 11, (Nov. 7, 2018), 23 pgs.
Coonrod, A, et al., "On the mechanism of DNA transfection: efficient gene transfer without viruses", Gene Therapy, 4(12), (1997), 1313-1321.
Croyle, Maria, et al., "Development of novel formulations that enhance adenoviral-mediated gene expression in the lung in vitro and in vivo.", Molecular Therapy, 4(1), (Jul. 2001), 22-28.
Denby, L., et al., "Adeno-associated virus (AAV)-7 and -8 poorly transduce vascular endothelial cells and are sensitive to proteasomal degradation.", Gene Ther., 12(20), (Oct. 2005), 1534-8.
Deng, Xuefeng, et al., "In vitro modeling of human bocavirus 1 infection of polarized primary human airway epithelia", J Virol. vol. 87, No. 7, 4097-4102, (Jan. 23, 2013), 7 pgs.
Desai, Shyamal, et al., "Ubiquitin-dependent Destruction of Topoisomerase I Is Stimulated by the Antitumor Drug Camptothecin", Journal of Biological Chemistry, 272(39), (Sep. 26, 1997), 24159-24164.
Dietrich, Cornelia, et al., "p53-dependent cell cycle arrest induced by N-acetyl-L-leucinyl-L-leucinyl-L-norleucinal in platelet-derived growth factor-stimulated human fibroblasts.", Proc Natl Acad Sci USA., 93(20), (1996), 10815-10819.
Ding, W., et al., "Second-Strand Genome Conversion of Adeno-Associated Virus Type 2 (AAV-2) and AAV-5 is Not Rate Limiting Following Apical Infection of Polarized Human Airway Epithelia", Journal of Virology, 77(13), (2003), 7361-7366.
Ding, Wei, et al., "Proteasome Inhibitor LLnL (MG101) Augments AAV5 Transduction in Polarized Human Airway Epithelia", American Society of Gene Therapy, Abstracts of Scientific Presentations—Abstract No. 571, (Jun. 5, 2002), 1 page.
Dishart, Kate, et al., "Recombinant Adeno-Associated Virus-2 as a Candidate Gene Delivery Vector for Vein Grafts", American Society of Gene Therapy, Abstracts of Scientific Presentations—Abstract No. 1107, (Jun. 5, 2002), 1 page.
Djaldetti, M., et al., "SEM observations on the effect of anthracycline drugs on cultured newborn rat cardiomyocytes (Abstract Only)", Basic Res Cardiol., vol. 6, (1988), 627-7.
Doll, R. F, et al., "Comparison of promoter strengths on gene delivery into mammalian brain cells using AAV vectors", Gene Therapy, 3(5), (1996), 437-447.

(56) References Cited

OTHER PUBLICATIONS

Dollard, S. C, et al., "Enhanced responsiveness to nuclear factor kappa B contributes to the unique phenotype of simian immunodeficiency virus variant SIVsmmPBj14.", J Virol., 68(12), (Dec. 1994), 7800-9.
Donaldson, S. H., et al., "Regulation of the Epithelial Sodium Channel by Serine Proteases in Human Airways", The Journal of Biological Chemistry, 277(10), (2002), 8338-8345.
Dou, Q. P, et al., "Proteasome inhibitors as potential novel anticancer agents", Drug Resist Updat., 2(4), (Aug. 1999), 215-223.
Douar, A., et al., "Intracellular trafficking of adeno-associated virus vectors: routing to the late endosomal compartment and proteasome degradation.", J Virol., 75(4), (Feb. 2001), 1824-33.
Droge, W., et al., "HIV-induced cysteine deficiency and T-cell dysfunction—a rationale for treatment with N-acetylcysteine", Immunol Today., 13(6), (Jun. 1992), 211-4.
Duan, D, et al., "Response to "Polarity Influences the Efficiency of Recombinant Adenoassociated Virus Infection in Differentiated Airway Epithelia"", Human Gene Therapy, 10, (1999), 1553-1557.
Duan, D., "A New Dual-Vector Approach to Enhance Recombinant Adeno-Associated Virus-Mediated Gene Expression Through Intermolecularcis Activation", Nature Medicine, 6(5), (2000), 595-598.
Duan, D., et al., "Chapter 15: Trans-Splicing Vectors Expand the Packaging Limits of Adeno-Associated Virus for Gene Therapy Applications", Methods in Molecular Medicine, vol. 76: Viral Vectors for Gene Therapy: Methods and Protocols, (2003), 287-307.
Duan, D., et al., "Chapter 3—Adeno-Associated Virus", In: Lung Biology in Health and Disease, vol. 169—Gene Therapy in Lung Disease, Albelda, S. M., Editor, Marcel Dekker, Inc., (2002), 51-92.
Duan, D., et al., "Chapter 3—Dual Vector Expansion of the Recombinant AAV Packaging Capacity", In: Methods in Molecular Biology, vol. 219: Cardiac Cell and Gene Transfer, Metzger, J. M., Editor, Human Press, Inc., Totowa, NJ, (2003), 29-51.
Duan, D., "Consequences of DNA-Dependent Protein Kinase Catalytic Subunit Deficiency on Recombinant Adeno-Associated Virus Genome Circularization and Heterodimerization in Muscle Tissue", Journal of Virology, 77(8), (2003), 4751-4759.
Duan, D., et al., "Endosomal processing limits gene transfer to polarized airway epithelia by adeno-associated virus", J Clin Invest., 105(11), (Jun. 2000), 1573-87.
Duan, D., et al., "Enhancement of Muscle Gene Delivery With Pseudotyped Adeno-Associated Virus Type 5 Correlates With Myoblast Differentiation", Journal of Virology, 75(16), (2001), 7662-7671.
Duan, D., et al., "Expanding AAV Packaging Capacity with Trans-splicing or Overlapping Vectors: A Quantitative Comparison", Molecular Therapy, 4(4), http://www.idealibrary.com, (2001), 383-391.
Duan, D., "Formation of Adeno-Associated Virus Circular Genomes is Differentially Regulated by Adenovirus E4 ORF6 and E2a Gene Expression", Journal of Virology, 73(1), (Jan. 1999), 161-169.
Duan, D., "Polarity Influences the Efficiency of Recombinant Adenoassociated Virus Infection in Differentiated Airway Epithelia", Human Gene Therapy, 9, (Dec. 10, 1998), 2761-2776.
Duan, D., et al., "Structural and Functional Heterogeneity of Integrated Recombinant AAV Genomes", Virus Research, 48(1), (Jan. 1997), 41-56.
Duan, Dongsheng, et al., "Circular intermediates of recombinant adeno-associated virus have defined structural characteristics responsible for long-term episomal persistence in muscle tissue", Journal of Virology, 72(11), (Nov. 1998), 8568-77.
Duan, Dongsheng, et al., "Dynamin is required for recombinant adeno-associated virus type 2 infection", Journal of Virology, 73(12), (Dec. 1999), 10371-10376.
Duan, Dongsheng, et al., "Polarity Influences the Efficiency of Recombinant Adenoassociated Virus Infection in Differentiated Airway Epithelia", Human Gene Therapy vol. 9, (Dec. 1998), 2761-2776.
Duan, Dongsheng, et al., "Structural Analysis of adeno-associated virus transduction circular intermediates", Virology, 261(1), (Aug. 15, 1999), 8-14.
Ecelbarger, C. A., et al., "Regulation of the Abudance of Renal Sodium Transporters and Channels by Vasopressin", Experimental Neurology, 171, (2001), 227-234.
Eck, Stephen L, et al., "Chapters: Gene-Based Therapy", Goodman & Gilman's The Pharmacological Basis of Therapeutics, 9th Edition, McGraw-Hill, New York, NY, (1996), 77-101.
Elliott, P J, et al., "Recent Advances in Understanding Proteasome Function", Current Opinion in Drug Discovery and Development, 5 (2), ISSN: 1367-6733, (1999), 484-490.
Elmarakby, A., et al., "NADPH oxidase inhibition attenuates oxidative stress but not hypertension produced by chronic ET-1", Hypertension, 45(2), (Feb. 2005), 283-7.
Engelhardt, J., et al., "Adeno-Associated Virus Vectors", U.S. Appl. No. 60/086,166, filed May 20, 1998, 96 pgs.
Engelhardt, J., et al., "Compounds and Methods for Pharmico-Gene Therapy of Epithelial Sodium Channel Associated Disorders", U.S. Appl. No. 10/815,557, filed Mar. 31, 2004, 137 pgs.
Engelhardt, J., et al., "Compounds and Methods to Enhance Adenoassociated Virus Transduction", U.S. Appl. No. 60/138,188, filed Jun. 8, 1999, (Jun. 8, 1999), 102 pgs.
Engelhardt, J., et al., "Compounds and Methods to Enhance rAAV Transduction", U.S. Appl. No. 10/815,262, filed Mar. 31, 2004, 156 pgs.
Engelhardt, J. F., et al., "Direct gene transfer of human CFTR into human bronchial epithelia of xenografts with E1-deleted adenoviruses", Nature Genetics, 4(1), (1993), 27-34.
Engelhardt, J. F., "The Lung as a Metabolic Factory for Gene Therapy", The Journal of Clinical Investigation, 110(4), (2002), 429-432.
Engelhardt, John, et al., "Adeno-Associated Virus Vectors", U.S. Appl. No. 09/276,625, filed Mar. 25, 1999, (Mar. 25, 1999), 122 pgs.
Engelhardt, John, et al., "Adeno-Associated Virus Vectors", U.S. Appl. No. 10/054,665, filed Jan. 22, 2002, 138 pgs.
Engelhardt, John, et al., "Compounds and Methodsd to Enhance Adenoassociated Virus Transduction", U.S. Appl. No. 60/201,089, filed May 2, 2000, 138 pgs.
Engelhardt, John, et al., "Enhancement of Muscle Gene Delivery With Pseudotyped AAV-5 Correlates With Myoblast Differentiation", U.S. Appl. No. 60/305,204, filed Jul. 13, 2001, 117 pgs.
Englehardt, John, et al., "Adeno-Associated Virus Vectors and Uses Thereof", U.S. Appl. No. 09/684,554, filed Oct. 6, 2000, 141 pgs.
Englehardt, John, "Compounds and Methods for Pharmico-Gene Therapy of Epithelial Sodium Channel Associated Disorders", U.S. Appl. No. 60/512,347, filed Oct. 16, 2003, 135 pgs.
Englehardt, John, et al., "Compounds and Methods to Enhance rAAV Transduction", U.S. Appl. No. 60/459,323, filed Mar. 31, 2003, 173 pgs.
Englehardt, John, et al., "Compounds and Methods to Enhance rAAV Transduction", U.S. Appl. No. 09/689,136, filed Oct. 12, 2000, (, 138 pgs.
Englehardt, John, et al., "Pseudotyped Adeno-Associated Viruses and Uses Thereof", U.S. Appl. No. 10/194,421, filed Jul. 12, 2002, 138 pgs.
Everett, R D., et al., "A viral activator of gene expression functions via the ubiquitin-proteasome pathway", The EMBO Journal, 17 (24), (1998), pp. 7161-7169.
Excoffon, Katherine J. D. A, et al., "Directed Evolution of Adeno-Associated Virus to an Infectious Respiratory Virus", Proceedings of the National Academy of Sciences, vol. 106, No. 10, (Mar. 10, 2009), 3865-3870.
Fakhiri, Julia, et al., "Novel Chimeric Gene Therapy Vectors Based on Adeno-Associated Virus and Four Different Mammalian Bocaviruses", Molecular Therapy: Methods & Clinical Development vol. 12, (Mar. 2019), 202-222.
Fallin, R. A., et al., "PMA-lnduced Inhibition of Amiloride-Sensitive Sodium Absorption is Partially Mediated by ERK1/2 Activation", The FASEB Journal, 17(5) (Abstracts Part II), Abstract No. 585-19, (2003), A915.
Fasbender, Al, et al., "Complexes of adenovirus with polycationic polymers and cationic lipids increase the efficiency of gene transfer in vitro and in vivo", The Journal of Biological Chemistry, 272 (10), (Mar. 7, 1997), 6479-6489.

(56) References Cited

OTHER PUBLICATIONS

Fayadat, Laurence, et al., "Degradation of Human Thyroperoxidase in the Endoplasmic Reticulum Involves Two Different Pathways Depending on the Folding State of the Protein", Journal of Biological Chemistry, 275(21), (May 26, 2000), 15948-15954.

Fehilly, Carole B, et al., "Interspecific chimaerism between sheep and goat", Nature vol. 307, (Feb. 16, 1984.), 634-6.

Fenteany, G, et al., "Inhibition of proteasome activities and subunit-specific amino-terminal threonine modification by lactacystin", Science, 268(5211), (1995), 726-731.

Fenteany, Gabriel, et al., "Lactacystin, Proteasome Function, and Cell Fate", Journal of Biological Chemistry, 273(15), (Apr. 10, 1998), 8545-8548.

Ferrari, F K., et al., "Second-Strand Synthesis Is a Rate-Limiting Step for Efficient Transduction by Recombinant Adeno-Associated Virus Vectors", Journal of Virology, 70(5), (1996), 3227-3234.

Ferrari, Forrest, et al., "Second-Strand Synthesis Is a Rate-Limiting Step for Efficient Transduction by Recombinant Adneo-Associated Virus Vectors", Journal of Virology vol. 70, No. 5, (3227-3234), May 1996.

Figueiredo-Pereira, Maria E, et al., "The antitumor drug aclacinomycin A, which inhibits the degradation of ubiquitinated proteins, shows selectivity for the chymotrypsin-like activity of the bovine pituitary 20 S proteasome", Journal of Biological Chemistry, 271(28), (Jul. 12, 1996), 16455-16459.

Finn, J. D, et al., "Proteasome inhibitors decrease AAV2 capsid derived peptide epitope presentation on MHC class I following transduction", Mol Ther., 18(1), (Jan. 2010), 135-42.

Finn, Jonathan D., et al., "Proteasome Inhibitors Decrease AAV2 Capsid-Derived Peptide Epitope Presentation on MHC Class I Following Transduction", Molecular Therapy vol. 18 No, 1, 135-142 Jan. 2010, (Jan. 1, 2010), 135-142.

Fisher, K J., et al., "Transduction with recombinant adeno-associated virus for gene therapy is limited by leading-strand synthesis", Journal of Virology, 70(1), (Jan. 1996), 520-532.

Fisher, Krishna, et al., "Recombinant adeno-associated virus for muscle directed gene therapy", Nature Medicine, 3(3), (Mar. 1997), 306-312.

Fisher-Adams, G., et al., "Integration of Adeno-Associated Virus Vectors in CD34+ Human Hematopoietic Progenitor Cells After Transduction", Blood, 88 (2), (Jul. 15, 1996), pp. 492-504.

Flotte, T., et al., "A Phase I Study of an Adeno-Associated Virus-CFTR Gene Vector in Adult CF Patients With Mild Lung Disease", Human Gene Therapy, 7(9), (1996), 1145-1159.

Flotte, T. R., et al., "Adeno-Associated Virus Vector Gene Expression Occurs in Nondividing Cells in the Absence of Vector DNA Integration", American Journal of Respiratory Cell and Molecular Biology, 11, (1994), pp. 517-521.

Flotte, T. R., et al., "Chapter 40—Adeno-Associated Viral Vectors for CF Gene Therapy", In: Methods in Molecular Medicine, 70, (2002), 599-608.

Furst, R., et al., "Atrial natriuretic peptide induces mitogen-activated protein kinase phosphatase-1 in human endothelial cells via Rac1 and NAD(P)H oxidase/Nox2-activation", Circ Res., 96(1), (Jan. 7, 2005), 43-53.

Gabizon, Alberto, "Long-circulating liposomes fordrug delivery in cancer therapy: a review of biodistribution studies in tumor-bearing animals", Advanced Drug Delivery Reviews, (1997), 337-344.

Gabizon, Alberto, et al., "Preclinical Studies with Doxorubicin Encapsulated in Polyethyleneglycol-Coated Liposomes", Journal of Liposome Research, 3(3), (1993), 517-528.

Gadallah, M. F., et al., "Epithelial Sodium Channel-Dependent Hyptertension: An Emerging Syndrome", Journal of the American Society of Nephrology, 10 (Abstracts Issue), Abstract No. A1842, (1999), 365A.

Gadallah, M. F., et al., "Preservation of Renal Function in Patients with Hypertension and Chronic Renal Impairment; Revisited", Journal of the American Society of Nephrology, 10 (Abstracts Issue), Abstract No. A1841, (1999), 365A.

Gao, Feng, et al., "DNA-guided genome editing using the Natronobacterium gregoryi Argonaute", In Journal of Nature Biotechnology Advance Online Publication, (May 2, 2016), 1-7.

Gao, H., et al., "Critical Role for microglial NADPH Oxidase in Rotenone-induced degeneration of Dopaminergic Neurons", Journal of Neuoscience; 23(15), (Jul. 16, 2003), 6181-6187.

Gao, H. M, et al., "Critical role of microglial NADPH oxidase-derived free radicals in the in vitro MPTP model of Parkinson's disease", FASEB J., 17(13), (Oct. 2003), 1954-6.

Gao, H. M, et al., "Novel anti-inflammatory therapy for Parkinson's disease.", Trends Pharmacol Sci., 24(8), (Aug. 2003), 395-401 pgs.

Gao, Hui-Ming, et al., "Distinct Role for Microglia in Rotenone-Induced Degeneration of Dopaminergic Neurons", Journal of Neuroscience 22(3), (Feb. 1, 2002), 782-790.

Garber, Ken, "Taking Garbage In, Taking Cancer Out?", Science, vol. 295, (Jan. 25, 2002), 612-613.

Ginn, S. L., et al., "Gene therapy clinical trials worldwide to 2012—an update.", J Gene Med, 15(2), (2013), 65-77.

Giraud, Catherine, et al., "Recombinant junctions formed by site-specific integration of adeno-associated virus into an episome", Journal of Virology, 69 (11), (Nov. 1995), 6917-6924.

Goldberg, A L., et al., "New insights into proteasome function: from archaebacteria to drug development", Chemistry & Biology, 2(8), (1995), 503-508.

Goncalves, M. A, "Adeno-associated virus: from defective virus to effective vector", Virol J., 2, (May 6, 2005), 17 pgs.

Gormley, K., et al., "Regulation of the Epithelial Sodium Channel by Accessory Proteins", Biochem. J., 371, (2003), 1-14.

Gorvel, J. P, et al., "rab5 controls early endosome fusion in vitro.", Cell, 64(5), (Mar. 8, 1991), 915-25.

Gottlieb, T A., et al., "Actin Microfilaments Play a Critical Role in Endocytosis at the Apical but not the Basolateral Surface of Polarized Epithelial Cells", The Journal of Cell Biology, 120 (3), (1993), pp. 695-710.

Graham, J. M, et al., "Iodixanol—a new density gradient medium for the dissection of the endosomal compartment", Z Gastroenterol., 34 Suppl 3, (1996), 76-8.

Graham, J., "Purification of peroxisomes using a density barrier in a swinging-bucket rotor.", ScientificWorldJournal, 2, (May 22, 2002), 1400-3.

Graham, J., et al., "The preparation of subcellular organelles from mouse liver in self-generated gradients of iodixanol", Anal. Biochem., 220(2), (1994), 367-73.

Grimm, D., et al., "From Virus Evolution to Vector Revolution: Use of Naturally Occurring Serotypes of Adeno-Associated Virus (AAV) as Novel Vectors for Human Gene Therapy", Current Gene Therapy, 3, (2003), 281-304.

Gross, R., "Clinical problems of optimum bioavailability, in particular in cytostatic therapy (Abstract Only)", Arzneimittelforschung, vol. 26(1A), (1976), 130-5.

Gruchala, Marcin, et al., "Adeno-Associated Virus-Mediated Gene Transfer into Normal Rabbit Arteries. Assessment of the Tie and CMV Promoters and the Antiproteasome Treatment with MG-132", American Society of Gene Therapy, Abstracts of Scientific Presentations—abstract No. 1110, (Jun. 5, 2002), 1 page.

Gruenberg, J, et al., "Membrane traffic in endocytosis: insights from cell-free assays.", Annu Rev Cell Biol., 5, (1989), 453-81.

Guido, et al., "", World Journal of Gastroenterology, (2016), 8684-8697.

Gurda, Brittney L., et al., "Human Bocavirus Capsid Structure: Insights into the Structural Repertoire of the Parvoviridae", Journal of Virology, 84(12), (Jun. 2010), 5880-5889.

Hagstrom, J. N., et al., "Improved Muscle-Derived Expression of Human Coagulation Factor IX from a Skeletal Actin/CMV Hybrid Enhancer/Promoter", Blood, 95(8), (2000), 2536-2542.

Halbert, C. L., "Transduction by Adeno-Associated Virus Vectors in the Rabbit Airway: Efficiency, Persistence, and Readministration", Journal of Virology, 71 (8), (Aug. 1997), pp. 5932-5941.

Hamilton, Bradley A, et al., "Polarized AAVR Expression Determines Infectivity by AAV Gene Therapy Vectors", Gene Therapy, Nature Publishing Group, London, GB, vol. 26, No. 6, (Apr. 8, 2019), 240-249.

(56) References Cited

OTHER PUBLICATIONS

Hansen, J., et al., "Adeno-Associated Virus Type 2-Mediated Gene Transfer: Altered Endocytic Processing Enhances Transduction Efficiency in Murine Fibroblasts", Journal of Virology, 75(9), (2001), 4080-4090.

Hansen, J., et al., "Impaired Intracellular Trafficking of Adeno-Associated Virus Type 2 Vectors Limits Efficient Transduction of Murine Fibroblasts", Journal of Virology, 74(2), (2000), 992-996.

Harraz, et al., "SOD1 mutations disrupt redox-sensitive Rac regulation of NADPH oxidase in a familial ALS model", The Journal of Clinical Investigation, vol. 118, No. 2, (Feb. 2008), 659-670.

Hasegawa, S., et al., "Microtubule Involvement in the Intracellular Dynamics for Gene Transfection Mediated by Cationic Liposomes", Gene Therapy, 8, (2001), 1669-1673.

Hashimoto, Y, et al., "Amino- and carboxyl-terminal mutants of presenilin 1 cause neuronal cell death through distinct toxic mechanisms: Study of 27 different presenilin 1 mutants", J Neurosci Res. 75(3), Abstract Only, (Feb. 2004), 417-28.

Haung, Qinfeng, et al., "Establishment of a Reverse Genetics System for Studying Human Bocavirus in Human Airway Epithelia", Journal PLOS Pathogens vol. 8(8), (2012), 1-14.

He, Y, et al., "Minocycline inhibits microglial activation and protects nigral cells after 6-hydroxydopamine injection into mouse striatum", Brain Res. 909(1-2), Abstract Only, (Aug. 2001), 187-93.

Hermonat, Paul, et al., "Use of adeno-associated virus as a mammalian DNA cloning vector: Transduction of neomycin resistance into mammalian tissue culture cells", Proc. Natl. Acad. Sci. USA, vol. 81, (Oct. 1984), 6466-6470.

Herzog, Roland W., et al., "Stable gene transfer and expression of human blood coagulation factor IX after intramuscular injection of recombinant adeno-associated virus", Proceedings of the National Academy of Sciences of the United States of America, 94, (May 1997), 5804-9.

Higgins, D. G., "CLUSTAL: a package for performing multiple sequence alignment on a microcomputer.", Gene, 73(1), (Dec. 15, 1988), 237-44.

Higgins, D. G., "Fast and sensitive multiple sequence alignments on a microcomputer.", Comput Appl Biosci., 5(2), (Apr. 1989), 151-153.

Hong, J., et al., "Identification of SRI6975, A Compound that Enhances Adenovirus-Mediated Gene Expression in Polarized Epithelial Cells", Cystic Fibrosis Foundation: 2000 North American CF Conference, (Nov. 2000), 1-2.

Hosseini, Hassan, et al., "Protection against experimental autoimmune encephalomyelitis by a proteasome modulator", Journal of Neuroimmunology, 188, (2001), 233-244.

Houdebine, L., "Production of Pharmaceutical Proteins From Transgenic Animals", Journal of Biotechnology, vol. 34, France, (1994), 269-287.

Hsu, A., et al., "Ritonavir. Clinical pharmacokinetics and interactions with other anti-HIV agents", Clin Pharmacokinet, 35(6), abstract, (Dec. 1998), 1 page.

Hsy, Py, et al., "Effect of Polyethylenimine on Recombinant Adenoassociated Virus Mediated Insulin Gene Therapy", 1. J Gene Med. Oct. 2005;7(10):1311-21—School of Pharmacy, College of Medicine, National Taiwan University, 1, Jen-Ai Road, Section 1, Taipei 100 Taiwan, (Oct. 7, 2005), 1311-21.

Huang, L., et al., "Efficient lipofection with cisplatin-resistant human tumor cells", Cancer Gene Therapy, vol. 3, No. 2, (1996), 107-112.

Hummler, E., et al., "Genetic Disorders of Membrane Transport—V. The Epithelial Sodium Channel and its Implication in Human Diseases", American Journal of Physiology, Gastrointensinal and Liver Physiology, 276, (1999), G567-G571.

Hunziker, et al., "Review—Perspectives: toward a peptide-based vaccine against hepatitis C virus", Molecular Immunol, 38, (2001), 475-484.

Iqbal, Mohamed, et al., "Potent Inhibitors of Proteasome", Journal of Medicinal Chemistry, vol. 38, No. 13, (1995), 2276-2277.

Ishiawata, Akira, et al., "Phenotype correction of hemophilia A mice with adeno-associated virus vectors carrying the B domain-deleted canine factor VIII gene", Thrombosis Research, Tarrytown, NY, US, vol. 118, No. 5, (2006), (2006), 627-635.

Itani, O. A., et al., "Cycloheximide Increases Glucocorticoid-Stimulated alpha-ENaC mRNA in Collecting Duct Cells by p38 MAPK-dependent Pathway", Am. J. Physiol. Renal Physiol., 284, (2002), F778-F787.

Iwane, Marika, et al., "(Abstract) Population-based surveillance for hospitalizations associated with respiratory syncytial virus, influenza virus, and parainfluenza viruses among young children,", Pediatrics, 113 (6). pp. 1758-1764, (2004), 2 pgs.

Jennings, K., et al., "Proteasome inhibition enhances AAV-mediated transgene expression in human synoviocytes in vitro and in vivo", Mol Ther., 11(4), (Apr. 2005), 600-7.

Jensen, T J., et al., "Multiple Proteolytic Systems, Including the Proteasome, Contribute to CFTR Processing", Cell, 83, (1995), pp. 129-135.

Jiang, Q., et al., "Cellular Heterogenecity of CFTR Expression and Function in the Lung: Implications for Gene Therapy of Cystic Fibrosis", European Journal of Human Genetics, 6(1), (Jan. 1998), 12-31.

Johannesson, T., et al., "Neurodegenerative diseases, antioxidative enzymes and copper. A review of experimental research.]", Laeknabladid, 89(9), (Sep., 2003), 659-671.

Johnson, J. S., et al., "Enhancement of Adeno-Associated Virus Infection by Mobilizing Capsids into and Out of the Nucleolus", Journal of Virology, 83(6), (2009), 2632-2644.

Johnson, L. G, et al., "Efficiency of gene transfer for restoration of normal airway epithelial function in cystic fibrosis", Nature Genetics 2, (1992), 21-25.

Jorgensen, M. J., et al., "Expression of Completely y-Carboxylated Recombinant Human Prothrombin", The Journal of Biological Chemistry, 262(14), (1987), 6729-6734.

Julia, Fakhiri, et al., "254. New Chimeric Gene Therapy Vectors Based on Four Different Mammalian Bocaviruses", Molecular Therapy, vol. 24, No. S1, (May 1, 2016), S100.

Kamynina, E., et al., "Concerted Action of ENaC, Nedd4-2, and Sgk1 in Transepithelial Na+ Transport", Am. J. Physiol. Renal Physiol., 283, (2002), F377-F387.

Kannan, R., et al., "Impairment of conjunctival glutathione secretion and ion transport by oxidative stress in an adenovirus type 5 ocular infection model of pigmented rabbits.", Free Radic Biol Med., 37(2), (Jul. 15, 2004), 229-38.

Kaplan, Johanne M., et al., "Potentiation of gene transfer to the mouse lung by complexes of adenvirus vector and polycations improves therapeutic potential", Human Gene Therapy, vol. 9, No. 10, XP000972242, (Jul. 1, 1998), 1469-1479.

Kaplitt, M. G., "Long-Term Gene Expression and Phenotypic Correction Using Adeno-Associated Virus Vectors in the Mammalian Brain", Nature Genetics, 8(2), (Oct. 1994), 148-154.

Kapoor, A., et al., "Human bocaviruses are highly diverse, dispersed, recombination prone, and prevalent enteric infections", J Infect Dis. 201(11), (Jun. 2010), 1633-1643.

Kapoor, Amit, et al., "Bocavirus Episome in Infected Human Tissue Contains Non-Identical Termini", Plos One, (2011), vol. 6, No. 6, e21362, (2011), 8 pgs.

Kapoor, Amit, et al., "Identification and Characterization of a New Bocavirus Species in Gorillas", PLOS ONE, (2010), vol. 5, No. 7, p. e11948, (Jul. 2010), 6 pgs.

Kappell, Catherine A., et al., "Regulating gene expression in transgenic animals", Current Opinion in Biotechnology vol. 3, (1992), 548-553.

Kapturczak, M. H, et al., "Adeno-Associated Virus (AAV) as a Vehicle for Therapeutic Gene Delivery: Improvements in vector Design and Viral Production Enhance Potential to prolong Graft Survival in Pancreatic Islet Cell Transplantation for the Reversal of Type I Diabetes", Current Molecular Medicine, (2001), 245-258.

Kay, M. A., et al., "Evidence for Gene Transfer and Expression of Factor IX in Haemophilia B Patients Treated with an AAV Vector", Nature Genetics, 24, (2000), 257-261.

(56) References Cited

OTHER PUBLICATIONS

Kazi, A., et al., "Inhibition of the Proteasome Activity, a Novel Mechanism Associated with the Tumor Cell Apoptosis-Inducing Ability of Genistein", Biochemical Pharmacology, 66, (2003), 965-976.

Kearns, W. G., et al., "Recombinant Adeno-Associated Virus (AAV-CFTR) Vectors do not Integrate in a Site-Specific Fashion in an Immortalized Epithelial Cell Line", Gene Therapy, 3, (1996), 748-755.

Kellenberger, et al., "Epithelial Sodium Channel/Degenerin Family of Ion Channels: A Variety fo Functions fora Shared Structure", Physiological Review, 82, (2002), 735-767.

Kessler, P D, et al., "Gene delivery to skeletal muscle results in sustained expression and systemic delivery of a therapeutic protein", Proceedings of the National Academy of Sciences of the United States of America, 93(24), (Nov. 26, 1996), 14082-7.

Kessler, P., et al., "Sodium Butyrate Greatly Enhances the efficiency of Viral Transduction in Adult Ventricular Cardiomyocytes by Adeno-associated Viral Vectors", Circulation 92(8), (Oct. 15, 1995), 296.

Kim, Koanhoi, "Proteasome Inhibitors Sensitize Human Vascular Smooth Muscle Cells to Fas (CD95)—Mediated Death", Biochemical and Biophysical Research Communications, vol. 281, No. 2, (2001), 305-310.

Kim, Kyung Bo, et al., "Proteasome Inhibition by the Natural Products Epoxomicin and Dihydroeponemycin: Insights into Specificity and Potency", Bioorganic & Medicinal Chemistry Letters, (1999), 3335-3340.

Kiyomiya, Ken-Ichi, et al., "Mechanism of specific nuclear transport of adriamycin: the mode of nuclear translocation of adriamycin-proteasome complex", Cancer Res., 61(6), (Mar. 15, 2001), 2467-71.

Kiyomiya, Ken-Ichi, "The role of the proteasome in apoptosis induced by anthracycline anticancer agents", International Journal of Oncology, 20(6), Preliminary Report on Patentability, (Jun. 2002), 1205-9.

Kiyomiya, K-I, et al., "Proteasome is a Carrier to Translocate Doxorubicin from Cytoplasm into Nucleus", Life Sciences, 62(20), (1998), 1853-1860.

Kloetzel, P M., "The Proteasome system: a neglected tool for improvement of novel therapeutic strategies?", Gene Therapy, 5, (1998), pp. 1297-1298.

Kotin, R. M., et al., "Characterization of a preferred site on human chromosome 19q for integration of adeno-associated virus DNA by non-homologous recombination", The EMBO Journal, 11 (13), (1992), pp. 5071-5078.

Kumar, Gita, "Side-stepping the side effects", BioCentury, The Bernstein Report on BioBusiness, (Dec. 17, 2001), 7.

Lambeth, J. D., "Nox enzymes and the biology of reactive oxygen", Nature Reviews, Immunology,4(3), (2004), 181-189.

Lebkowski, J., "Adeno-Associated Virus: a Vector System for Efficient Introduction and Integration of DNA into a Variety of Mammalian Cell Types", Molecular and Cellular Biology, 8(10), (Oct. 1988), 3988-3996.

Lechardeur, D., et al., "Intracellular Barriers to Non-Viral Gene Transfer", Curr. Gene Therapy, 2, (2002), 183-194.

Lee, D. H, et al., "Proteasome inhibitors: valuable new tools for cell biologists", Trends Cell Biol., 8(10), (Oct. 1998), 397-403.

Lee, Do Hee, et al., "Selective Inhibitors of the Proteasome-dependent and Vacuolar Pathways of Protein Degradation in *Saccharomyces cerevisiae*", Journal of Biological Chemistry, (Nov. 1, 1996), 27280-27284.

Lee, Do Hee, et al., "The Proteasome Inhibitors and Their Uses", Proteasomes: The World of Regulatory Proteolysis, (2000), 154-175.

Lee, K., et al., "Shuttle PCR-based cloning of the infectious adeno-associated virus type 5 genome", Journal of Virological Methods, 111(2), (Aug. 2003), 75-84.

Lee, Sang Goo, et al., "Enhancement of adenoviral transduction with polycationic liposomes in vivo", Cancer Gene Therapy, vol. 7, No. 10, (2000), 1329-1335.

Lefebvre, R. B., et al., "Conformation Takes Precedence Over Sequence in Adeno-Associated Virus DNA Replication", Molecular and Cellular Biology, 4(7), (1984), 1416-1419.

Li, et al., "Cloned ferrets produced by somatic cell nuclear transfer", Dev. Biol vol. 293, Iss. 2, (2006), 439-448.

Li, et al., "Progress toward generating a ferret model of cystic fibrosis by somatic cell nuclear transfer", Reprod. Biol. and Endocrinology vol. 1, (2003), 1-8.

Li, M., et al., "Macrophage colony stimulatory factor and interferon-gama trigger distinct mechanisms for augmentation of beta-amyloid-induced microglia-mediated neurotoxicity", J. Neurochem 91(3), Abstract Only, (Nov. 2004), 1 pg.

Li, Q., et al., "Nox2 and Rac1 regulate H2O2-dependent recruitment of TRAF6 to endosomal interleukin-1 receptor complexes", Mol Cell Biol., 26(1), (Jan. 2005), 140-54.

Li, Wuping, et al., "Generation of Novel AAV Variants by Directed Evolution for Improved CFTR Delivery to Human Ciliated Airway Epithelium", Journal of Molecular Therapy vol. 17(12), (Dec. 2009), 2067-2077.

Liang, E., et al., "Oligonucleotide delivery: a cellular prospective", Pharmazie, vol. 54, No. 8, XP000965598, (Aug. 1999), 559-566.

Lin, H. C, et al., "Prediction of tyrosine sulfation sites in animal virus", Biochemical and Biophysical Research Communications,312(4), (Dec. 26, 2003), 1154-1158.

Lin, S, et al., "Delivery of a Novel AAV, AV.T165-CFTR, to Human Bronchial Epithelial Cells from Patients with Cystic Fibrosis Augments Functional Recovery of Chloride Conductance", Pediatric Pulmonology; 33RD Annual North American Cystic Fibrosis Conference Oct. 31, 2019 to Nov. 2, 2019 Nashville, TN, John Wiley & Sons, Inc, US, vol. 54, No. Supplement 2, (Oct. 1, 2019), p. 218.

Linden, R. M., et al., "Site-specific integration by adeno-associated virus", PNAS, 93, (Oct. 1994), pp. 11288-11294.

Linden, R. M., et al., "The Recombinant Signals for Adeno-Associated Virus Site-Specific Integration", Proc. Natl. Acad. Sci. USA, 93, (Jul. 1996), 7966-7972.

Loguercio, C., et al., "Oxidative stress in viral and alcoholic hepatitis.", Free Radic Biol Med., 34(1), (Jan. 1, 2003), 1-10.

Lu, Wei, et al., "HIV protease inhibitors restore impaired T-cell proliferative response in vivo and in vitro: a viral-suppression-independent mechanism", Blood, vol. 96, No. 1, (Jul. 1, 2000), 250-258.

Lu, X., et al., "Synthesis and biological evaluations of novel apocynin analogues", Eur J Med Chem., 46(7), (Jul. 2011), 2691-8.

Lull, M. E, et al., "Chronic apocynin treatment attenuates beta amyloid plaque size and microglial number in hAPP(751)(SL) mice", PLoS One, 6(5), (2011), e20153.

Luo, Hongyu, et al., "A Proteasome Inhibitor Effectively Prevents Mouse Heart Allograft Rejection", Transplantation, vol. 72, No. 2, (Jul. 27, 2001), 196-202.

Ma, Xiaoming, et al., "Detection of Human Bocavirus in Japanese Children with Lower Respiratory Tract Infections", J Clin Microbiol, 44, (2006), 1132-1134.

Ma, Y., et al., "p53-Independent Down-Regulation of Mdm2 in Human Cancer Cells Treated with Adriamycin", Molecular Cell Biology Research Communications, 3(2), (Feb. 2000), 122-128.

Macías-Pérez, Martha Edith, et al., "Ethers and Esters Derived Rom Apocynin Avoid the Interaction Between p47phox AND p22phox Subunits of NADPH Oxidase: Evaluation In Vitro and In Silico", (Biosci. Rep., 33: e00055 (2013)), (2013), 605-616.

Mah, C, et al., "Adeno-Assodated Virus Type 2-Mediated Gene Transfer: Role of Epidermal Growth Factor Receptor Protein Tyrosine Kinase in Transgene Expression", Journal of Virology, 72 (12), (1998), pp. 9835-9843.

Mah, C., et al., "Improved Method of Recombinant AAV2 Delivery for Systemic Targeted Gene Therapy", Molecular Therapy, 6(1), (2001), 106-112.

Maitra, R., et al., "Increased Functional Cell Surface Expression of CFTR and deltaF508-CFTR by the Anthracycline doxorubicin", Am. J. Physiol. Cell Physiol., 280, (May 2001), C1031-C1037.

(56) References Cited

OTHER PUBLICATIONS

Malik, B., et al., "ENaC Degradation in A6 Cells by the Ubiquitin-Proteosome Proteolytic Pathway", The Journal of Biological Chemistry, 276(16), (Apr. 20, 2001), 12903-12910.
Marshall, E "Gene Therapy's Growing Plans", Science 269(5227), (1995), 1050-1055.
Mastroianni, Claudio M, et al., "Ex Vivo and In Vitro Effect of Human Immunodeficiency Virus Protease Inhibitors on Neutrophil Apoptosis", Journal of Infectious Diseases (182), (Nov. 2000), 1536-1539.
Matalon, S., et al., "Lung Edema Clearance: 20 Years of Progress—Invited Review: Biophysical Properties of Sodium Channels in Lung Alveolar Epithelial Cells", J. Appl. Physiol., 93, (2002), 1852-1859.
Mattsson, Karin, et al., "Proteins associated with the promyelocytic leukemia gene product (PML)-containing nuclear body move to the nucleolus upon inhibition of proteaseome-dependent protein degradation", Proc. National Academy of Science, vol. 98, No. 3, (Jan. 30, 2001), 1012-1017.
McAuliffe, O., et al., "Lantibiotics: Structure, Biosynthesis and Mode of Action", FEMS Microbiology Reviews, 25(3), (2001), 285-308.
McCarty, D. M., et al., "Identification of Linear DNA Sequences That Specifically Bind the Adeno-Associated Virus Rep Protein", Journal of Virology, 68(8), (1994), 4988-4997.
McCarty, D. M., et al., "Interaction of the Adeno-Associated Virus Rep Protein With a Sequence Within the A Palindrome of the Viral Terminal Repeat", Journal of Virology, 68(9), (1994), 4998-5006.
McFadden, G., "Even viruses can learn to cope with stress.", Science, 279(5347), (Jan. 2, 1998), 40-1.
McLaughlin, Susan K., et al., "Adeno-associated virus general transduction vectors: analysis of proviral structures", Journal of Virology, 62 (6), (Jun. 1988), pp. 1963-1973.
Meng, Lihao, et al., "Eponemycin Exerts Its Antitumor Effect through the Inhibition of Proteasome Function", Cancer Research, vol. 59, (Jun. 15, 1999), 2798-2801.
Meng, Lihao, et al., "Epoxomicin, a potent and selective proteasome inhibitor, exhibits in vivo antiinflammatory activity", Proc Natl Acad Sci USA, 96(18), (Aug. 31, 1999), 10403-8.
Meyer, Stephanie, et al., "Cyclosporine A is an uncompetitive inhibitor of proteasome activity and prevents NF-kB activation", Federation of European Biochemical Societies, (1997), 354-358.
Mihaylov, Ivailo, et al., "Complementation for an essential ancillary non-structural protein function across parvovirus genera", Virology, vols. 468-470, (2014), 226-237.
Mihm, S., et al., "Inhibition of HIV-1 replication and NF-kappa B activity by cysteine and cysteine derivatives.", AIDS, 5(5), (May 1991), 497-503.
Mikulski, S. M, et al., "Enhanced in vitro cytotoxicity and cytostasis of the combination of onconase with a proteasome inhibitor", Int J Oncol., 13(4), (Oct. 1998), 633-44.
Mingozzi, Federico, et al., "Pharmacological Modulation of Humoral Immunity in a Nonhuman Primate Model of AAV Gene Transfer for Hemophilia B", Molecular Therapy, vol. 20, No. 7, (May 8, 2012), 1410-1416.
Mirshahi, M., et al., "Paradoxical Effects of Mineralocorticoids on the Ion Gated Sodium Channel in Embryologically Diverse Cells", Biochemical and Biophysical Research Communications, 270, (2000), 811-815.
Mitsiades, Constantine, et al., "TRAIL/Apo2L ligand selectively induces apoptosis and overcomes drug resistance in multiple myeloma: theraputic applications", Blood, vol. 98, No. 3, (Aug. 1, 2001), 795-804.
Monahan, P E, et al., "Proteasome inhibitors enhance gene delivery by AAV virus vectors expressing large genomes in hemophilia mouse and dog models: a strategy for broad clinical application", Mol Ther 18, (2010), 1907-1916.
Mondejar-Lopez, Pedro, et al., "Cystic Fibrosis Treatment: Targeting the Basic Defect", Expert Opinion On Orphan Drugs, vol. 5, No. 2, (Feb. 26, 2017), 181-192.
Mosnaim, Aron, et al., "Degradation Kinetics of Leucine5-Enkephalin by Plasma Samples from Healthy Controls and Various Patient Populations: In Vitro Drug Effects", American Journal of Therapeutics, vol. 7, (2000), 185-194.
Mullins, et al., "Perspectives Series: Molecular Medicine in Genetically Engineered Animals", J. Clin. Invest. vol. 97, (1996), 1557-1560.
Mullins, et al., "Transgenesis in nonmurine species", Hypertension vol. 22, (1993), 630-633.
Muramatsu, S., et al., "Nucleotide Sequencing and Generation of an Infectious Clone of Adeno-Associated Virus-3", Virology, 221(1), (1996), 208-217.
Murray, R. Z, et al., "Proteasome inhibitors as anti-cancer agents", Anticancer Drugs, 11(6), (Jul. 2000), 407-17.
Musatov, S. A., et al., "Induction of Circular Episomes During Rescue and Replication of Adeno-Associated Virus in Experimental Models of Virus Latency", Virology, 275, (2000), 411-432.
Muzyczka, N., "Use of Adeno-Associated Virus as a General Transduction Vector for Mammalian Cells", In: Current Topics in Microbiology and Immunology, 158, Springer-Verlag, Berlin: R.W. Compans, et al., (Eds.), (1992), pp. 97-129.
Nakai, H., et al., "Helper-Independent and AAV-ITR-Independent Chromosomal Integration of Double-Stranded Linear DNA Vectors in Mice", Molecular Therapy, 7(1), (2003), 101-111.
Nakai, H., et al., "Increasing the Size of rAAV-Mediated Expression Cassettes in vivo by Intermolecular Joining of Two Complementary Vectors", Nature Biotechnology, 18, (2000), 527-532.
Nakai, H., et al., "Recruitment of Single-Stranded Recombinant Adeno-Associated Virus Vector Genomes and Intermolecular Recombination Are Responsible for Stable Transduction of Liver In Vivo", Journal of Virology, 74(20), (2000), 9451-9463.
Nakamura, H., et al., "Redox imbalance and its control in HIV infection", Antioxid Redox Signal., 4(3), (Jun. 2002), 455-64.
Nakayama, M., et al., "Hypomethylation Status of CpG Sites at the Promoter Region and Overexpression of the Human MDR1 Gene in Acute Myeloid Leukemias", Blood, 92(11), (1998), 4296-4307.
Nam, Sangkil, et al., "Tannic Acid Potently Inhibits Tumor Cell Proteasome Activity, Increases p27 and Bax Expression, and Induces G1 Arrest and Apoptosis", Cancer Epidemiology, Biomarkers & Prevention, vol. 10, (Oct. 2001), 1083-1088.
Nathwani, Amit C et al., "Enhancing Transduction of the Liver by Adenoassociated Viral Vectors", Gene Ther. Jan. 2009; 16(1): 60-69. doi:10.1038/gt.2008.137, (Jul. 1, 2009), 60-69.
Nepka, CH., et al., "Tannins, xenobiotic metabolism and cancer chemo-prevention in experimental animals", European Journal of Drug Metabolism and Pharmacokinetics, vol. 24, No. 2, (1999), 183-189.
Nepka, Charitini, et al., "Chemopreventive activity of very low dose dietary tannic acid administration in hepatoma bearing C3H male mice", Cancer Letters, vol. 141, (1999), 57-62.
Neves, D. D. C., et al., "Differentiation-dependent sensitivity to cell death induced in the developing retina by inhibitors of the ubiquitin-proteasome proteolytic pathway", European Journal of Neuroscience, vol. 13, (2001), 1938-1944.
Newman, G. W, et al., "Opposing regulatory effects of thioredoxin and eosinophil cytotoxicity-enhancing factor on the development of human immunodeficiency virus 1.", J ExpMed., 180(1), (Jul. 1, 1994), 359-63.
Nicolaus, B. J, "Symbiotic Approach to Drug Design", Decision Making in Drug Research, (Jan. 1, 1983), 173-186.
Nielsen, J., et al., "Spironolactone-Mediated Downregulation of the Epithelial Sodium Channel (eNaC) in Rat Kidney", FASEB Journal, 15(1) (Abstracts Part I), Abstract No. 393.11, (2001), A432.
Niikura, T, et al., "Characterization of V642I-AbetaPP-induced cytoxicity in primary neurons", J. Neruosci Res. 77(1), Abstract Only, (Jul. 2004), 54-62.
Oberdorf, J., et al., "Redundancy of Mammalian Proteasome & Subunit Function during Endoplasmic Reticulum Associated Degradation", Biochemistry; 40(44), (2001), 13397-13405.
Obin, M, et al., "Neurite outgrowth in PC12 cells. Distinguishing the roles of ubiquitylation and ubiquitin-dependent proteolysis", Journal of Biological Chemistry, 274 (17), (Apr. 23, 1999), 11789-11795.

(56) References Cited

OTHER PUBLICATIONS

Oda, T., et al., "Oxygen radicals in influenza-induced pathogenesis and treatment with pyran polymer-conjugated SOD.", Science, 244(4907), (May 26, 1989), 974-6.

Ogiso, Y., et al., "Proteasome inhibition circumvents solid tumor resistance to topoisomerase II-directed drugs", Cancer Res., 60(9), (May 1, 2000), 2429-34.

Olufemi, Fasina O, et al., "NP1 protein of the Bocaparvovirus Minute Virus of Canines controls acess to the viral capsid genes via its role in RNA processing", Journal of Virology., vol. 90, No. 4, (Dec. 4, 2015), 1718-1728.

Orkin, S. H., et al., "Report and recommendation of the Panel to Assess the NIH Investment in Research on Gene Therapy", [online], [retrieved Jul. 6, 2007], Retrieved from the Internet: <URL: file://E:\Enablement Rejections\Generally usefu art\wwwnihgov-news-panelrephtm.htm>, (Dec. 7, 1995), 39 pgs.

Palombella, Vito, et al., "Role of the proteasome and NF-kB in streptococcal cell wall-induced polyarthritis", Proc. National Academy of Science USA, vol. 95, (Dec. 1998), 15671-15676.

Paolini, Rossella, et al., "Ubiquitination and degradation of Syk and ZAP-70 protein tyrosine kinases in human NK cells upon CD16 engagement", PNAS, vol. 98, No. 17, (Aug. 14, 2001), 9611-9616.

Pardridge, William M, "Blood-Brain Barrier Drug Targeting: The Future of Brain Drug Development", Molecular Interventions 3(2), (Mar. 2003), 90-105.

Parker, J. S., et al., "Cellular Uptake and Infection by Canine Parvovirus Involves Rapid Dynamin-Regulated Clathrin-Mediated Endocytosis, Followed by Slower Intracellular Trafficking", Journal of Virology, 74(4), (2000), 1919-1930.

Patel, et al., "identification of Yeast DNA Topoisomerase II Mutants Resistant to the Antitumor Drug Doxorubcin: Implications for the Mechanisms of Doxorubicin Action and Cytotoxicity", Pharmacol. 52(4), (1997), 658-666.

Petrov, Victor, et al., "Effect of Protease Inhibitors on Angiotensin-Converting Enzyme Activity in Human T-Lymphocytes", American Journal of Hypertension, vol. 13, No. 5, (May 2000), 535-539.

Phelps, C. J, et al., "Production of alpha 1,3-galactosyltransferase-deficient pigs", Science, 299(5605), (Jan. 17, 2003), 411-4.

Piccinini, M., et al., "The human 26S proteasome is a target of antiretroviral agents", AIDS, 16(5), abstract, (Mar. 29, 2002), 1 page.

Pickles, R J., et al., "Limited Entry of Adenovirus Vectors into Well-Differentiated Airway Epithelium Is Responsible for Inefficient Gene Transfer", Journal of Virology, 72 (7), (1998), pp. 6014-6023.

Plonne, D., et al., "Separation of the intracellular secretory compartment of rat liver and isolated rat hepatocytes in a single step using self-generating gradients of iodixanol.", Anal Biochem., 276(1), (Dec. 1, 1999), 88-96.

Ponnazhagan, S., et al., "Lack of Site-Specific Integration of the Recombinant Adeno-Associated Virus 2 Genomes in Human Cells", Human Gene Therapy, 8, (Feb. 10, 1997), pp. 275-284.

Pratelli, Annamaria, et al., "Host range of Canine minute virus in cell culture", Journal of Veterinary Diagnostic Investigation 24(5), (Jul. 23, 2012), 981-985.

Princiotta, Michael F, et al., "Cells adapted to the proteasome inhibitor 4-hydroxy-5-iodo-3-nitrophenylacetyl-Leu-Leu-leucinal-vinyl sulfone require enzymatically active proteasomes for continued survival", PNAS, vol. 98, No. 2, (Jan. 16, 2001), 513-518.

Prydz, K, et al., "Effects of Brefeldin A on Endocytosis, and Transport to the Golgi Complex in Polarized MDCK Cells", The Journal of Cell Biology, 119 (2), (1992), pp. 259-272.

Puttaraju, M., et al., "Spliceosome-mediated RNA trans-splicing as a tool for gene therapy", Nature Biotechnology, 17 (3), (Mar. 1999), pp. 246-252.

Qinfeng, Huang, et al., "Internal polyadenylation of parvoviral precursor mRNA limits progeny virus production", Virology, Elsevier, Amsterdam, NL, vol. 426, No. 2, (Jan. 26, 2012), 167-177.

Qing, K., et al., "Adeno-Associated Virus Type 2-Mediated Gene Transfer: Correlation of Tyrosine Phosphorylation of the Cellular Single-Stranded D Sequence-Binding Protein with Transgene Expression in Human Cells In Vitro and Murine Tissues In Vivo", Journal of Virology, 72 (2), (Feb. 1998), pp. 1593-1599.

Qing, K., et al., "Human Fibroblast Growth Factor Receptor 1 is a Co-Receptor for Infection by Adeno-Associated Virus 2", Nature Medicine, 5(1), (Jan. 1999), 71-77.

Qing, K., "Role of Tyrosine Phosphorylation of a Cellular Protein in Adeno-Associated Virus 2-Mediated Transgene Expression", Proc. Natl. Acad. Sci. USA, 94, (Sep. 1997), 10879-10884.

Qiu, Jianming, et al., "Characterization of the transcription profile of adeno-associated virus type 5 reveals a number of unique features compared to previously characterized adeno-associated viruses", Journal of Virol., 76, No. 24, (2002), 12435-12447.

Qiu, Jianming, et al., "The Transcription Profile of the Bocavirus Bovine Parvovirus Is Unlike Those of Previously Characterized Parvoviruses", Journal of Virology, vol. 81, No. 21, [Online], Retrieved from the Internet: <URL: https://jvi.asm.org/>, (2007), 12080-12085.

Rabinowitz, Joseph, et al., "Cross-Packaging of a Single Adeno-Associated Virus (AAV) Type 2 Vector Genome into Multiple AAV Serotypes Enables Transduction with Broad Specificity", Journal of Virology, (Jan. 2002), 791-801.

Ramage, A. D., et al., "Improved EBV-Based Shuttle Vector System: Dicistronic mRNA Couples the Synthesis of the Epstein-Barr Nuclear Antigen-1 Protein to Neomycin Resistance", Gene, 197(102), (1997), 83-89.

Rao, Sharmila, et al., "Lovastatin-mediated G1 arrest is through inhibition of the proteasome, independent of hydroxymethyl glutaryl-CoA reductase", Proc. National Academy of Science USA, vol. 96, (Jul. 1999), 7797-7802.

Reich, S. J., et al., "Efficient Trans-Splicing in the Retina Expands the Utility of Adeno-Associated Virus as a Vector for Gene Therapy", Human Gene Therapy, 14, (2003), 37-44.

Rendahl, K. G., et al., "Regulation of Gene Expression in vivo Following Transduction by Two Separate rAAv Vectors", Nature Biotechnology, 16, (1998), 757-761.

Richards, R. Gregg, et al., "E2-Induced Degradation of Uterine Insulin Receptor Substrate—2: Requirement for an IGF-I-Stimulated, Proteasome-Dependent Pathway", Endocrinology, 142(9), (Sep. 2001), 3842-3849.

Ricour, C., et al., "Human Bocavirus, a Newly Discovered Parvovirus of the Respiratory Tract", International Journal of Clinical and Laboratory Medicine, vol. 63, Issue 5, Abstract only, (2008), 329-334.

Rivett, A. J, et al., "Proteasome inhibitors: from in vitro uses to clinical trials", Journal of Peptide Science, 6(9), (Sep. 2000), 478-488.

Rock, K L., et al., "Inhibitors of the Proteasome Block the Degradation of Most Cell Proteins and the Generation of Peptides Presented on MHC Class I Molecules", Cell, 78, (1994), pp. 761-771.

Ros, C, et al., "The ubiquitin-proteasome machinery is essential for nuclear translocation of incoming minute virus of mice", Virology 324, (2004), 350-360.

Ross, G., et al., "Gene Therapy in the United States: A Five-Year Status Report", Human Gene Therapy, 7, (1996), 1781-1790.

Rotin, D., "Regulation of the Epithelial Sodium Channel (ENaC) by Accessory Proteins", Current Opinion in Nephrology and Hypertension, 9, (2000), 529-534.

Rotin, D., et al., "Trafficking and Cell Surface Stability of ENaC", Am. J. Physiol. Renal Physiol., 281, (2001), F391-F399.

Rubanyi, Gabor M., "The Future of Human Gene Therapy", Molecular Aspects of Medicine, 22, (2001), 113-142.

Russell, D W., et al., "DNA synthesis and topoisomerase inhibitors increase transduction by adeno-associated virus vectors", PNAS, 92, (1995), pp. 5719-5723.

Russell, S. J, "Replicating Vectors for Gene Therapy of Cancer: Risks, Limitations and Prospects", European J Cancer, vol. 30A (8), (1994), 1165-1171.

(56) References Cited

OTHER PUBLICATIONS

Ryan, J. H., et al., "Sequence Requirements for Binding of Rep68 to the Adeno-Associated Virus Terminal Repeats", Journal of Virology, 70(3), (1996), 1542-1553.
Saha, D., et al., "The antiangiogenic agent SU5416 down-regulates phorbol ester-mediated induction of cyclooxygenase 2 expression by inhibiting nicotinamide adenine dinucleotide phosphate oxidase activity", Cancer Res., 63(20), (Oct. 15, 2003), 6920-7.
Sakai, H., et al., "Cloning and functional expression of a novel degenerin-like Na+ channel gene in mammals", J. Physiol 519, (1999), 323-333.
Salganik, Max, et al., "Adeno-associated Virus as a Mammalian DNA Vector", Microbiol. Spectr., 3:10.1128, (Aug. 2015), 32 pgs.
Samulski, R. J., et al., "A Recombinant Plasmid from Which an Infectious Adeno-Associated Virus Genome Can Be Excised In Vitro and Its Use To Study Viral Replication", Journal of Virology, 61(10), (Oct. 1987), 3096-3101.
Samulski, R. J., "Adeno-Associated Virus: Integration at a Specific Chromosomal Locus", Current Opinion in Genetics & Development, 3(1), (1993), 74-80.
Samulski, R. J., et al., "Helper-Free Stocks of Recombinant Adeno-Associated Viruses: Normal Integration Does Not Require Viral Gene Expression", Journal of Virology, 63 (9), (Sep. 1989), pp. 3822-3828.
Sanlioglu, et al., "Novel Approaches To Augment Adeno-Associated Virus TYPE-2 Endocytosis and Transduction", Virus Research and Transduction,104(1), (Aug. 2004), 51-59.
Sanlioglu, S, et al., "Cellular redox state alters recombinant adeno-associated virus transduction through tyrosine phosphatase pathways", Gene Therapy vol. 6, No. 8, (Aug. 1999), pp. 1427-1437.
Sanlioglu, S., et al., "Endocytosis and Nuclear Traffickling of Adeno-Associated Virus Type 2 Are Controlled by Rac1 and Phosphatidylinositol-3 Kinase Activation", Journal of Virology, 74(19), (Oct. 2000), 9184-9196.
Sanlioglu, S., et al., "Lipopoolysaccharide Induces Rac1-Dependent Reactive Oxygen Species Formation and Coordinates Tumor Necrosis Factor-alpha Secretion Through IKK Regulation of NF-kB", The Journal of Biological Chemistry, 276(32), (2001), 30188-30198.
Sanlioglu, S., "Loss of ATM Function Enhances Recombinant Adeno-Associated Virus Transduction and Integration Through Pathways Similar to UV Irradiation", Virology, 268, (2000), 68-78.
Sanlioglu, S., et al., "Rate Limiting Steps of AAV Transduction and Implications for Human Gene Therapy", Current Gene Therapy, 1, (2001), 137-147.
Sanlioglu, S., et al., "Two Independent Molecular Pathways for Recombinant Adeno-Associated Virus Genome Conversion Occur After UV-C and E4orf6 Augmentation of Transduction", Human Gene Therapy, 10(4), (1999), 591-602.
Sasaki, T., et al., "Inhibitory Effect of di- and Tripeptidyl Aldehydes on Calpains and Cathepsins", Journal of Enzyme Inhibition, 3(3), (1990), 195-201.
Schaefer, et al., "Molecular cloning, functional expression and chromosomal localization of an amiloride-sensitive Na+ channel from human small intestine", FEBS Letters 471, (2000), 205-210.
Schnepp, B. C., et al., "Genetic Fate of Recombinant Adeno-Associated Virus Vector Genomes in Muscle", Journal of Virology, 77(6), (2003), 3495-3504.
Schreck, R., et al., "Antioxidants selectively suppress activation of NF-kappa B by human T-cell leukemia virus type I Tax protein", J Virol., 66(11), (Nov. 1992), 6288-93.
Schwartz, Donald, et al., "The neutral cysteine protease bleomycin hydrolase is essential for epidermal integrity and bleomycin resistance", Proc. National Academy of Science USA, vol. 96, (Apr. 1999), 4680-4685.
Schwartz, O, et al., "Antiviral Activity of the Proteasome on Incoming Human Immunodeficiency Virus Type 1", Journal of Virology, 72 (5), (1998), pp. 3845-3850.
Schwarz, K., "Oxidative stress during viral infection: a review.", Free Radic Biol Med., 21(5), (1996), 641-9.

Schwarz, Katrin, et al., "The Selective Proteasome Inhibitors Lactacystin and Epoxomicin can be used to either Up- or Down-Regulate Antigen Presentation at Nontoxic Doses", Journal of Immunology, (2000), 6147-6157.
Schwarzbach, M., et al., "Sensitization of Sarcoma cells to doxorubicin treatment by concomitant wild-type adeno-associated virus type 2(AAV-2) infection", Oncology,20, (2002), 1211-1218.
Sen, S, et al., "Characterisation of gene transfer to vascular cell lines using adenoassociated virus (AAV Serotype-2)", Endocrine Abstracts, 4 DP31; Dept. of medicine, National Univ, of Ireland, Galway, Ireland; 2The Ohio State Univ. School of Medicine and Molecular Virology, Columbus, Ohio, USA, (2002), 1 pg.
Serwer, et al., "Systemic and Local Drug Delivery for Treating Diseases of the Central Nervous System in Rodent Models", Jove, vol. 42, (2010), 1-6.
Shah, S. A., et al., "26S Proteasome Inhibition Induces Apoptosis and Limits Growth of Human Pancreatic Cancer", Journal of Cellular Biochemistry, vol. 82, (2001), 110-122.
Sharma, A, et al., "Pig cells that lack the gene for alpha1-3 galactosyltransferase express low levels of the gal antigen", Transplantation, 75(4), (Feb. 27, 2003), 430-6.
Shay, David, et al., "Bronchiolitis-Associated Hospitalizations Among US Children, 1980-1996", JAMA, vol. 282, No. 15, (1999), 1440-1446.
Shen, Weiran, et al., "Analysis of cis and trans Requirements for DNA Replication at the Right-End Hairpin of the Human Bocavirus 1 Genome", Journal of Virology 90.17, (2016), 7761-7777.
Shisler, J. L, et al., "Ultraviolet-induced cell death blocked by a selenoprotein from a human dermatotropic poxvirus", Science,279(5347), (Jan. 2, 1998), 102-5.
Sloots, Theo, et al., "Evidence of human coronavirus HKU1 and human bocavirus in Australian Children", J Clin Virol, 35, (2006), 99-102.
Smith, Andrew, et al., "The Role of the Epidermal Growth Factor Receptor in Recombinant Adeno-Associated Virus Type-2 Mediated Transgene Expression in Lung Epithelial Cells", Molecular Therapy, 5(5), abstract, (May 2002), S186.
Smith, H., et al., "Effect of a cancer cachectic factor on protein synthesis/degradation in murine C2C12 myoblasts: modulation by eicosapentaenoic acid", Cancer Res., 59(21), abstract, (Nov. 1999), 1 page.
Snyder, P. M., et al., "Serum and Glucocorticoid-Regulated Kinase Modulates Nedd4-2-Mediated Inhibition of the Epithelial NA+ Channel", The Journal of Biological Chemistry, 277(1), (2002), 5-8.
Snyder, R. O., et al., "Features of the Adeno-Associated Virus Origin Involved in Substrate Recognition by the Viral Rep Protein", Journal of Virology, 67(10), (1993), 6096-6104.
Snyder, R. O., et al., "Persistent and therapeutic concentrations of human factor IX in mice after hepatic gene transfer of recombinant AAV vectors", Nature Genetics, 16, (Jul. 1997), pp. 270-276.
Son, K, et al., "Factors influencing the drug sensitization of human tumor cells for in situ lipofection", Gene Therapy (3), (1996), 630-634.
Son, Kyonghee, et al., "Exposure of human ovarian carcinoma to cisplatin transiently sensitizes the tumor cells for liposome-mediated gene transfer", Proc. National Academy of Science USA, vol. 91, (Dec. 1994), 12669-12672.
Son, Kyonghee, et al., "Nitric oxide-mediated tumor cell killing of cisplatin-based interferon-y gene therapy in murine ovarian carcinoma", Cancer Gene Therapy, vol. 7, No. 10, (2000), 1324-1328.
Sonntag, Florian, et al., "Adeno-associated Virus Type 2 Capsids with Externalized VP1/VP2 Trafficking Domains Are Generated Prior to Passage through the Cytoplasm and Are Maintained until Uncoating Occurs", Journal of Virology, vol. 80, No. 22, (Nov. 2006), 11040-11054.
Spindler, B., et al., "Characterization of Early Aldosterone-induced RNAs identified in A6 Kidney Epithelia", Pfluegers Archiv, vol. 434, Springer Verlag, Berlin, De XP001025924 ISSN: 0031-6768, (1997), 323-331.
Srivastava, C. H., et al., "Construction of a Recombinant Human Parvovirus B19: Adeno-Associated Virus 2 (AAV) DNA Inverted Terminal Repeats are Functional in an AAV-B19 Hybrid Virus", Proc. Natl. Acad. Sci USA, 86(20), (1989), 8078-8082.

(56) References Cited

OTHER PUBLICATIONS

Staub, O., "Chapters Regulation of ENaC by Interacting Proteins and by Ubiquitination", Current Topics in Membranes, 47—Amiloride-Sensitive Sodium Channels—Physiology and Functional Diversity, Edited by Dale J. Benos, Academic Press, Publisher, (1999), 65-87.
Staub, O., "Regulation of Stability and Functional of the Epithelial Na+ Channel (ENaC) by Ubiquitination", The EMBO Journal, 16(21), (1997), 6325-6336.
Stockand, J. D., et al., "Targeted Degradation of the Epithelial Na Channel (ENaC) in Response to PKC Activation of the MAPK 1/2 Cascade", The FASEB Journal, 17(5), Abstracts (Part II), (Abstract No. 585.7), (2003), A913.
Stokes, J. B., "Regulation of rENac mRNA by Dietary NaCl and Steroids: Organ, Tissue, and Steroid Heterogeneity", American Journal of Physiology, Cell Physiology, 274, (1998), C1699-C1707.
Stutts, M. J, et al., "Cystic fibrosis transmembrane conductance regulator inverts protein kinase A-mediated regulation of epithelial sodium channel single channel kinetics.", J. Biol. Chem., 272(22), (1997), 14037-14040.
Sukhu, L, et al., "Characterization of the Nonstructural Proteins of the Bocavirus Minute Virus of Canines", Journal of Virology., vol. 87, No. 2, (Nov. 7, 2012), 1098-1104.
Summerford, C., et al., "alphaVbetaS integrin: a co-receptor for adeno-associated virus type 2 infection", Nature Medicine, 5 (1), (Jan. 1999), 78-82.
Summerford, C., et al., "Membrane-Associated Heparan Sulfate Proteoglycan Is a Receptor for Adeno-Associated Virus Type 2 Virions", Journal of Virology, 72 (2), (Feb. 1998), pp. 1438-1445.
Sun, et al., "Molecular Characterization of Infectious Clones of the Minute Virus of Canines Reveals Unique Features of Bocaviruses", Journal of Virology, 83(8), (Apr. 2009), 3956-3967.
Sun, A. Y, et al., "Botanical phenolics and brain health", Neuromolecular Med., 10(4), (2008), 259-74.
Swinney, David C, et al., "Targeting protein ubiquitination for drug discovery. What is in the drug discovery toolbox?", DDT, vol. 6, No. 5, (Mar. 2001), 244-250.
Tajima, Kimihisa, et al., "The proteasome inhibitor MG132 promotes accumulation of the steroidogenic acute regulatory protein (StAR) and steriodogenesis", Federation of European Biochemical Societies, 490, (Jan. 24, 2001), 59-64.
Tang, Y, "435: Immunosuppressants improve the transduction of AAV2.5T after repeat dosing of ferret lungs", Pediatric Pulmonology; 34th Annual North American Cystic Fibrosis Conference; Oct. 7, 2020 to Oct. 23, 2020; Phoenix, AZ, USA, John Wiley & Sons, Inc, US, vol. 55, No. Suppl 2, (Oct. 1, 2020), p. 208.
Tang, Y, et al., "Study of the Neutralizing Antibody after rAAV. TL65 Transduction in Ferret Airway", Pediatric Pulmonology; 33rd Annual North American Cystic Fibrosis Conference, Nashville, TN, John Wiley & Sons, Inc, US, vol. 54, No. Supplement 2, (Oct. 1, 2019), p. 325.
Tenenbaum, et al., "Cellular contaminants of adeno-associated virus vector stocks can enhance transduction", Gene Therapy, 6, (1999), 1045-1053.
Tenenbaum, et al., "Evaluation of Risks Related to the Use of Adeno-Associated Virus-Based Vectors", Current Gene Therapy, 3, (2003), 545-565.
Teodori, L., et al., "Reduction of 1-beta-D-arabinofuranosylcytosine and adriamycin cytotoxicity following cell cycle arrest by anguidine", Cancer Res., 41(4), abstract, (Apr. 1981), 1 page.
Teoh, M. L, et al., "Tumorigenic poxviruses up-regulate intracellular superoxide to inhibit apoptosis and promote cell proliferation", J Virol., 79(9), (May 2005), 5799-811.
Teramoto, S., et al., "Factors influencing adeno-associated virus-mediated gene transfer to human cystic fibrosis airway epithelial cells: comparison with adenovirus vectors.", J Virol., 72(11), (Nov. 1998), 8904-12.
Thakur, et al., "Strategies for ocular siRNA delivery: Potential and limitations of non-viral nanocarriers", Journal of Biological Engineering, 6, (2012), 1-7.

Thomas, C. P., et al., "Genomic Organization of the 5' End of Human B-ENaC and Preliminary Characterization of its Promoter", Am. J. Physiol. Renal Physiol. 282, (2002), F898-F909.
Thrasher, A J, et al., "Generation of recombinant adeno-associated virus (rAAV) from an adenoviral vector and functional reconstitution of the NADPH-oxidase", Gene Therapy, Macmillan Press Ltd., Basinstoke, GB, Vo. 2, 1995, pp. 481-485, XP000651495, (1995), 5 pgs.
Touyz, R. M, et al., "Expression of a functionally active gp91phox-containing neutrophil-type NAD(P)H oxidase in smooth muscle cells from human resistance arteries: regulation by angiotensin II", Circ Res., 90(11), (Jun. 14, 2002), 1205-13.
Trischler, M., et al., "Biochemical analysis of distinct Rab5- and Rab11-positive endosomes along the transferrin pathway.", J Cell Sci., 112 (Pt 24), (Dec. 1999), 4773-4783.
Tweedale, Tony, "[Dioxin-I] Inhibits Estrogen-Induced Breast Cancer Cell Proliferation", Reuters Health, http//lists.essential.org/pipermail/dioxin-I/Week-of-Mon-2000103/000096.html, (Dec. 1999), 1 page.
Unzu, Carmen, et al., "Transient and intensive pharmacological immunosuppression fails to improve AAV-based liver gene transfer in nonhuman primates", Journal of Translational Medicine, Biomed Central, vol. 10, No. 1, (Jun. 15, 2012), 12 pgs.
Van Den Worm, E., et al., "Apocynin: A Lead-Compound for New Respiratory Burst Inhibitors", van den Worm thesis, Chapter 3, entitled Apocynin: a lead compound for new respiratory burst inhibitors? (2001)), (2001), 49-58.
Van Den Worm, E et al., "Effects of Methoxylation of Apocynin and Analogs on the Inhibition of Reactive Oxygen Species Production by Stimulated Human Neutrophils", Eur J Pharmacol. Dec. 21, 2001;433(2-3):225-30 (Abstract), (Dec. 21, 2001), 1 pg.
Van Den Worm, E., et al., "Effects of methoxylation of apocynin and analogs on the inhibition of reactive oxygen species production by stimulated human neutrophils", Euro. Jour. of pharm.;433(2-3), (Dec. 21, 2001), 225-230 Pgs.
Van Kerkhof, Peter, et al., "Proteasome Inhibitors Block a Late Step in Lysosomal Transport of Selected Membrane but not Soluble Proteins", Molecular Biology of the Cell, vol. 12, (Aug. 2001), 2556-2566.
Verma, I. M., et al., "Gene Therapy - Promises, Problems and Prospects", Nature, 389, (1997), 239-242.
Vihinen-Ranta, M, et al., "Intracellular Route of Canine Parvovirus Entry", Journal of Virology, 72 (1), (1998), pp. 802-806.
Villani, P., et al., "Antiretrovirals: Simultaneous determination of five protease inhibitors and three nonnucleoside transcriptase inhibitors in human plasma by a rapid high-performance liquid chromatography-mass spectrometry assay", The Drug Monit., 23(4), abstract, (Aug. 2001), 1 page.
Voinea, et al., "Designing of Intelligent liposomes for efficient delivery of drugs", J. cell. Mol. Med. 6(4), (2002), 465-474.
Wagner, J. A., et al., "A Phase I/II Study of tgAAV-CF for the Treatment of Chronic Sinusitis in Patients with Cystic Fibrosis", Human Gene Therapy, 9(6), (1998), 889-909.
Wagner, J. A., et al., "Safety and Biological Efficacy of an Adeno-Associated Virus Vector-Cystic Fibrosis Transmembrane Regulator (AAV-CFTR) in the Cystic Fibrosis Maxillary Sinus", The Laryngoscope, 109(2, Part 1), (1999), 266-274.
Wall, R. J., "Transgenic Livestock: Progress and Prospects for the Future", Theriogenology, 45, (1996), 57-68.
Walsh, C. E., "Phenotypic Correction of Fanconi Anemia in Human Hematopoietic Cells with a Recombinant Adeno-associated Virus Vector", The Journal of Clinical Investigation, 94(4), (Oct. 1994), 1440-1448.
Walters, R W., et al., "Basolateral localization of fiber receptors limits adenovirus infection from the apical surface of airway epithelia", The Journal of Biological Chemistry, 274(15), (Apr. 9, 1999), 10219-10226.
Walters, R W., et al., "Incorporation of Adeno-Associated Virus in a Calcium Phosphate Coprecipitate Improves Gene Transfer to Airway Epithelia In Vitro and In Vivo", Journal of Virology, 74 (1), (2000), 535-540.

(56) References Cited

OTHER PUBLICATIONS

Wang, Jiali, et al., "Identification of a novel bocaparvovirus in a wild squirrel in Kunming, Yunnan Province, China", Archives of Virology 165, (2020), 1469-1474.

Wang, Kaiyu, et al., "Improvement of Pharmacokinetics Behavior of Apocynin By Nitrone Derivatization: Comparative Pharmacokinetics of Nitrone-Apocynin and Its Parent Apocynin in Rats", (PLoS ONE, 8:070189 (2013)), (2013), 6 pgs.

Wang, Zekun, et al., "Development of a Novel Recombinant Adeno-Associated Virus Production System Using Human Bocavirus 1 Helper Genes", Molecular Therapy: Methods & Clinical Development vol. 11, (Dec. 2018), 40-51.

Wang, Zekun, et al., "Parvovirus Expresses a Small Noncoding RNA That Plays an Essential Role in Virus Replication", Journal of Virology, vol. 91 Issue 8, (2017), 1-20.

Wei, Ran Shen, et al., "Identification and functional analysis of novel nonstructural proteins of human bocavirus 1", Journal of Virology., vol. 89, No. 19, (Oct. 1, 2015), 10097-10109.

Wei, Zou, et al., "Nonstructural Protein NP1 of Human Bocavirus 1 Plays a Critical Role in the Expression of Viral Capsid Proteins", Journal of Virology., vol. 90, No. 9, (May 1, 2016), 4658-4669.

Weitzman, M. D., et al., "Adeno-Associated Virus (AAV) Rep Proteins Mediate Complex Formation Between AAV DNA and its Integration Site in Human DNA", Proc. Nat. Acad. Sci. USA, 91(13), (1994), 5808-5812.

Westfall, T. D., et al., "The Ecto-ATPase Inhibitor ARL 67156 Enhances Parasympathetic Neurotransmission in the Guinea-Pig Urinary Bladder", European Journal of Pharmacology, 329, (1997), 169-173.

Whitehouse, Alison, et al., "Downregulation of Ubiquitin-Dependent Proteolysis by Eicosapentaenoic Acid in Acute Starvation", Biochemical and Biophysical Research Communications, vol. 285, No. 3, (2001), 598-602.

Wickham, T J., et al., "Adenovirus targeted to heparan-containing receptors increases its gene delivery efficiency to multiple cell types", Nature Biotechnology, 14, (1996), pp. 1570-1573.

Wickham, T J., et al., "Targeted Adenovirus Gene Transfer to Endothelial and Smooth Muscle Cells by Using Bispecific Antibodies", Journal of Virology, 70 (10), (1996), pp. 6831-6838.

Woessner, Richard, et al., "Comparison of Three Approaches to Doxorubicin Therapy: Free Doxorubicin, Liposomal Doxorubicin, and B-Glucuronidase-Activated Prodrug (HMR 1826)", Anticancer Research, (2000), 2289-2296.

Wojcik, "Inhibition of the proteasome as a therapeutic approach", Drug Discovery Today, 4 (4), (Apr. 1999), pp. 188-189.

Wojcik, Cezary, et al., "Lovastatin and simvastatin are modulators of the proteasome", Int J Biochem Cell Biol., 32(9), (Sep. 2000), 957-65.

Working, Peter, et al., "Pharmacological-Toxicological Expert Report (Stealth Liposomal Doxorubicin HCI)", Human & Experimental Toxicology, (1996), 752-785.

Wu, C. W, et al., "Gene Therapy for Detached Retina by Adeno-Associated virus vecto Expressing Glial Line-Derived Neurotrophic Factor", Investigative Ophthalmology and visual science, 43(11), (Nov. 2002), 3480-3488.

Wu, D., et al., "NADPH-oxidase in a transgenic mouse model of familial amyotrophic lateral sclerosis", Society for Neuroscience Abstract Viewer and Iteinerary Planner, 2003, Abstract No. 528-13, URL—http://sf, XP008085727 & 33RD Annual Meeting of the Society of Neuroscience, New Orleans, LA, USA, (Nov. 8-12, 2003), 1 pg.

Wu, D., et al., "NADPH-Oxidase in a transgenic mouse model of familial amyotrophic lateral sclerosis (Abstract)", Program No. 528.12. Abstract Viewer/Itinerary Planner, (2003), 1 pg.

Wu, D., et al., "The inflammatory NADPH oxidase enzyme modulates motor neuron degeneration in amyotrophic lateral sclerosis mice", Proc Natl Acad Sci U S A., 103(32), (Aug. 8, 2006), 12132-7.

Wu, Du Chu, et al., "Blockade of Microglial Activation Is Neuroprotective in the 1-Methyl-4-Phenyl-1,2,3,6-Tetrahydropyridine Mouse Model of Parkinson Disease", Journal of Neuroscience, (Mar. 1, 2002), 1763-1771.

Wu, J., "On the role of proteasomes in cell biology and proteasome inhibition as a novel frontier in the development of immunosuppressants.", Am J Transplant., 2(10), (Nov. 2002), 904-12.

Wu, Jihong, et al., "Enhanced transduction and improved photoreceptor survival of retinal degeneration by the combinatorial use of rAAV2 with a lower dose of adenovirus", Vision Research 48, (2008), 1648-1654.

Wu, P., et al., "Adeno-Associated Virus Vector-Mediated Transgene Integration into Neurons and Other Nondividing Cell Targets", Journal of Virology, 72 (7), (Jul. 1998), pp. 5919-5926.

Xia, W., et al., "Presenilin 1 regulates the processing of beta-amyloid precursor protein C-terminal fragments and the generation of amyloid beta-protein in endoplasmic reticulum and Golgi", Biochemistry, 37(47), (Nov. 24, 1998), 16465-71.

Xiao, et al., "Efficient Long-Term Gene Transfer Into Muscle Tissue of Immunocomponent Mice by Adeno-Associated Virus Vector", Journal of Virology, 70(11), (1, Nov. 1996), 8098-8108.

Xiao, W, et al., "Adeno-Associated Virus as a Vector for Liver-Directed Gene Therapy", Journal of Virology, 72 (12), (1998), pp. 10222-10226.

Xiao, X., et al., "A Novel 165-Base-Pair Terminal Repeat Sequence Is the Sole cis Requirement for the Adeno-Associated Virus Life Cycle", Journal of Virology, 71(2), (Feb. 1997), 941-948.

Xuefeng, Deng, et al., "DNA Damage Signaling Is Required for Replication of Human Bocavirus 1 DNA in Dividing HEK293 Cells", Journal of Virology, vol. 91 No. 1, (Jan. 1, 2017), 20 pgs.

Xuefeng, Deng, et al., "Replication of an Autonomous Human Parvovirus in Non-dividing Human Airway Epithelium Is Facilitated through the DNA Damage and Repair Pathways", PLOS Pathogens vol. 12 No. 1, (Jan. 14, 2016), 25 pgs.

Y, Sun, et al., "Molecular Characterization of Infectious Clones of the Minute Virus of Canines Reveals Unique Features of Bocaviruse", Journal of Virology vol. 83 No. 8, (Feb. 11, 2009), 3956-3967.

Yalkinoglu, A. O, et al., "Inhibition of N-methyl-N'-nitro-N-nitrosoguanidine-induced methotrexate and adriamycin resistancce in CHO cells by adeno-associated virus type 2", Cancer,45(6), (1990), 1195-1203.

Yamagishi, S., et al., "Nifedipine inhibits tumor necrosis factor-alpha-induced monocyte chemoattractant protein-1 overexpression by blocking NADPH oxidase-mediated reactive oxygen species generation", Drugs Exp Clin Res., 29(4), (2003), 147-52.

Yan, Z, et al., "A Novel Chimeric Adenoassociated Virus 2/ Human Bocavirus 1 Parvovirus Vector Efficiently Transduces Human Airway Epithelia", Molecular Therapy, vol. 21 No. 12, (Dec. 2013), 2181-2194.

Yan, Z, "Trans-splicing vectors expand the utility of adeno-associated virus for gene therapy", Proc Natl Acad Sci U S A, 97(12), (Jun. 6, 2000), 6716-6721.

Yan, Z., et al., "A New Class of Hybrid Adeno-Associated Viral Vectors with Non-Homologous ITRs Improves Directional Recombination and Dual-Vector Reconstitution of Large Transgenes", Molecular Therapy, 9(Suppl. 1), (2004), S5-S6.

Yan, Z., et al., "A novel chimeric adenoassociated virus 2/human bocavirus 1 parvovirus vector efficiently transduces human airway epithelia", Mol Ther. vol. 21, No. 12, (Jul. 30, 2013), 2181-2194.

Yan, Z., et al., "Distinct classes of proteasome-modulating agents cooperatively augment recombinant adeno-associated virus type 2 and type 5-mediated transduction from the apical surfaces of human airway epithelia", J Virol., 78(6), (Mar. 2004), 2863-74.

Yan, Z., et al., "Inverted terminal repeat sequences are important for intermolecular recombination and circularization of adeno-associated virus genomes", Journal of Virology, 79(1), (Jan. 2005), 364-379.

Yan, Z., "Recombinant AAV-Mediated Gene Delivery Using Dual Vector Heterodimerizatiion", In: Methods in Enzmology, vol. 346: Gene Therapy Methods, Phillips, M. I., Editor, Academic Press, San Diego, CA, (2002), 334-357.

(56) References Cited

OTHER PUBLICATIONS

Yan, Z., et al., "Ubiquitination of Both Adeno-Associated Virus Type 2 and 5 Capsid Proteins Affects the Transduction Efficiency of Recombinant Vectors", Journal of Virology, 76(5), (2002), 2043-2053.

Yan, Ziying, et al., "A Common Theme for Ubiquitination-Dependent Transduction of rAAV Type 2 and 5", American Society of Gene Therapy, Abstracts of Scientific Presentations-Abstract No. 569, (Jun. 5, 2002), 1 page.

Yan, Ziying, et al., "Human Bocavirus Type-1 Capsid Facilitates the Transduction of Ferret Airways by Adeno-Associated Virus Genomes", Human Gene Therapy, vol. 28, No. 8, (2017), 612-625.

Yang, J., et al., "Concatamerization of Adeno-Associated Virus Circular Genomes Occurs Through Intermolecular Recombination", Journal of Virology, 73(11), (Nov. 1999), 9468-9477.

Yang, Wan-Zhu, et al., "Genome characterization of a novel porcine bocavirus", Archives of Virology; Official Journal of the Virology Division of the International Union of Microbiological Societies, Springer-Verlag, VI, (2012), vol. 157, No. 11, (Jul. 21, 2012), 2125-2132.

Yu, J., et al., "The Role of the Methoxyphenol Apocynin, a Vascular NADPH Oxidase Inhibitor, as a Chemopreventative Agent in the Potential Treatment of Cardiovascular Diseases", (Curr. Vasc. Pharmacol., 6:204 (2008), (2008), 14 pgs.

Zabner, J, et al., "Adenovirus-mediated gene transfer to ciliated airway epithelia requires prolonged incubation time", Journal of Virology, 70(10), (Oct. 1996), 6994-7003.

Zabner, J, et al., "Adenovirus-mediated generation of cAMP-stimulated Cl-transport in cystic fibrosis airway epithelia in vitro: effect of promoter and administration method.", Gene Therapy, 3(5), (1996), 458-465.

Zeitlin, Pamela L, "Novel pharmacologic therapies for cystic fibrosis", Perspective Series on cystic fibrosis 103(4), (Feb. 1999), 447-452.

Zentner, M. D, et al., "The Amiloride-sensitive epithelial Sodium Channel Alpha subunit is Transcriptionally down regulated in rat parotid cells by the extracellular signal-regulatedprotine Kinase pathway.", The Journal of the Biological Chemistry, vol. 273(46), (1998), 30770-30776.

Zhang, Chi, et al., "Identification and characterization of a novel rodent bocavirus from different rodent species in China", Emerging Microbes & Infections 7:48, (2018), 11 pgs.

Zhang, F, et al., "Proteasome Function is Regulated by Cyclic AMP-dependent Protein Kinase through Phosphorylation of Rpt6", The journal of Biological Chemistry;282(31), (Aug. 3, 2007), 22460-22471.

Zhou, Liqiao, et al., "Improvement of Transduction Efficiency from Split AAV Vectors", American Society of Gene Therapy, Abstracts of Scientific Presentations—Abstract, (Jun. 5, 2002), 1 page.

Zinn, Eric, et al., "Adeno-associated Virus: Fit to serve", Curr Opin Virol., (Oct. 2014), 13 pgs.

Zou, Wei, et al., "Nonstructural Protein NP1 of Human Bocavirus 1 Plays Critical Role in the Expression of Viral Capsid Protein", Journal of Virology May 2016 vol. 90 No. 9, (Feb. 18, 2016), 4658-4669.

"Israel Application Serial No. 261642, Notification of Defects in Patrent Application dated Mar. 15, 2023", w/ English Translation, 7 pgs.

\* cited by examiner

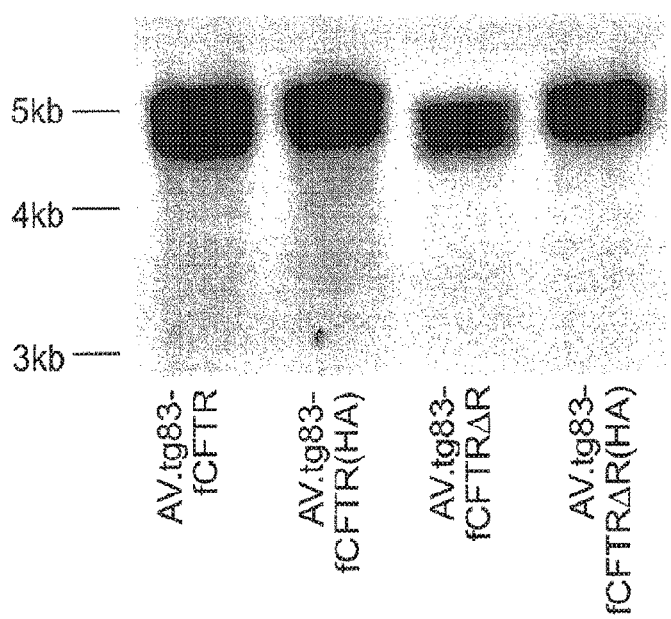
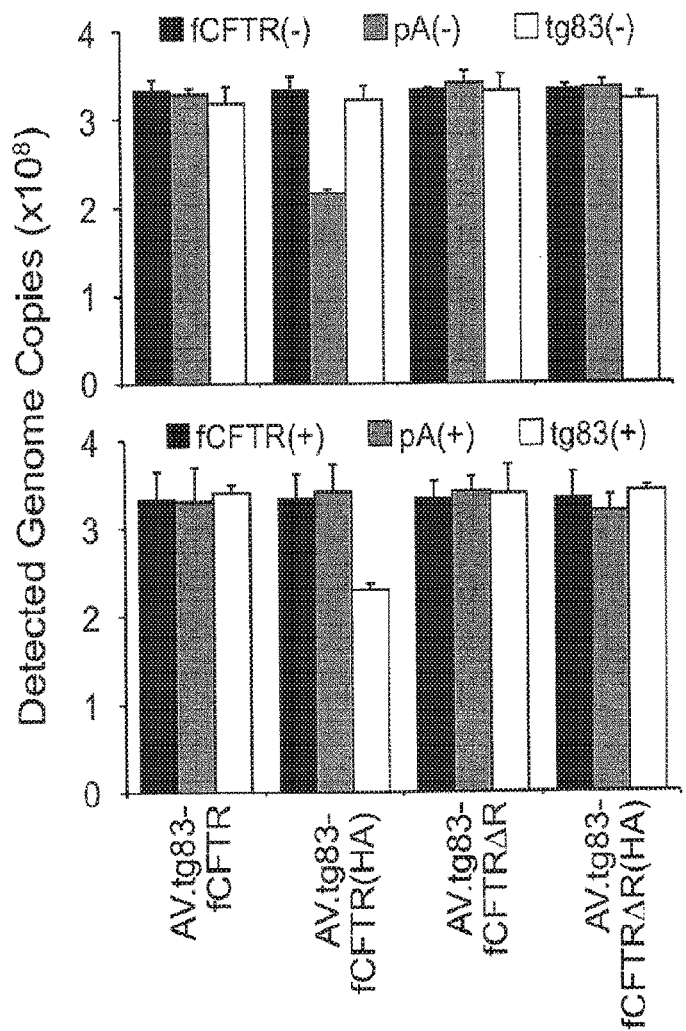
Figure 4

| Identifier | Binding Factor | Sequence (Search Pattern) |
|---|---|---|
| HS$A11COL_02 | | GTGGTTAGC |
| MOUSE$IAP_01 | | GTGGT |
| MOUSE$IAP_03 | EBP-80 | GTGGT |
| EBV$IR4_04 | R | CACCAC |
| EBV$IR4_05 | R | CACCAC |
| HS$PR264_01 | c-Myb | GGTGAG |
| HS$APOA2_06 | | TCACC |
| TDNA$NOS_01 | ASF-1, OBF3.1, TGA1a, TGA1b | TGAGC |
| DROME$UBX_08 | Zeste | TGAGCG |
| DROME$E74_07 | Zeste | TGAGCG |
| DROME$E74_08 | Zeste | TGAGCG |
| DROME$WHLO_04 | Zeste | TGAGCG |
| DROME$ZESTE_02 | Zeste | TGAGCG |
| DROME$UBX_06 | Zeste | CGCTCA |
| DROME$EVE_04 | GAGA factor | CGCTC |
| DROME$EVE_08 | GAGA factor | CGCTC |
| DROME$EVE_10 | GAGA factor | CGCTC |
| AS$PAX4_29 | Pax-4a | CATTCCCAGACG (SEQ ID NO:31) |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:32) |
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |

FIGURE 8A

| Identifier | Binding Factor | Sequence (Search Pattern) |
|---|---|---|
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:33) |
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:34) |
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |

FIGURE 8B

| Identifier | Binding Factor | Sequence (Search Pattern) |
|---|---|---|
| HS$CATHD_01 | ER-alpha, Sp1 | GGGCA |
| RAT$VEGF_01 | ER-alpha, ER-beta | GGGCA |
| CHICK$BAG_03 | | TGCCC |
| RAT$VEGF_02 | ER-alpha, ER-beta | TGCCC |
| HS$APAF1_01 | p53 | CGACAAGCCC (SEQ ID NO:35) |
| AS$HOXA3_13 | HOXA3 | CATGTTGGG |
| AS$FTZ_56 | Ftz | CCGACA |
| HSV1$GD_01 | ICP4 | CCGAC |
| AT$COR15A_01 | ANT, CBF1, CBF2, CBF3 | CCGAC |
| AT$RD29B_01 | CBF1 | CCGAC |
| AT$RD29A_01 | CBF1, DREB1A, DREB2A | CCGAC |
| AT$COR78_01 | ANT, CBF1, CBF2, CBF3 | CCGAC |
| AT$COR15B_01 | CBF1, CBF2, CBF3 | CCGAC |
| HS$CGB_03 | | CGGGCATCCTG (SEQ ID NO:36) |
| HS$CETP_02 | LXR-alpha, LXR-beta, RXR-alpha, | CGGGCA |
| HS$CYCD1_15 | Sp1, Sp2, Sp3, Sp4 | GCCCG |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER- | GGGCA |

FIGURE 8C

| Identifier | Binding Factor | Sequence (Search Pattern) |
|---|---|---|
| | alpha, ER-beta | |
| CHICK$BAG_03 | | TGCCC |
| RAT$VEGF_02 | ER-alpha, ER-beta | TGCCC |
| ASPN$ABAA_03 | abaA | CATTCT |
| ASPN$ABAA_04 | abaA | CATTCT |
| ASPN$ABAA_05 | abaA | CATTCT |
| ASPN$BRLA_03 | abaA | CATTCT |
| ASPN$RODA_05 | abaA | CATTCT |
| ABAA$CONS_01 | abaA | CATTCY |
| ASPN$BRLA_05 | abaA | CATTCT |
| ASPN$YA_02 | abaA | AGAATG |
| I$HSF_01 | HSF | AGAAN |
| F$HSF_01 | HSF | AGAAN |
| SV$SV40_37 | | CTGGG |
| RAT$IGFBP2_03 | Sp1 | TGGGCGTGTG (SEQ ID NO:37) |
| SV$SV40_63 | T-Ag | TGGGC |
| Y$HOP1_01 | | TGGGCGGCT |
| RAT$BMHC_04 | NFe | TGACGCCCA |
| MOUSE$GLUT4_03 | Sp1 | GGGCGT |
| HS$U2SN_04 | Sp1 | ACGCCC |
| HS$CD11B_01 | Sp1 | CGCCC |
| AS$PAX4_29 | Pax-4a | CATTCCCAGACG (SEQ ID NO:38) |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:39) |
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |

FIGURE 8D

| Identifier | Binding Factor | Sequence (Search Pattern) |
|---|---|---|
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:40) |
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |
| CHICK$BAG_09 | CTF | TCTGGGCA |
| SV$SV40_37 | | CTGGG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| CHICK$BAG_03 | | TGCCC |
| RAT$VEGF_02 | ER-alpha, ER-beta | TGCCC |

FIGURE 8E

| Identifier | Binding Factor | Sequence (Search Pattern) |
|---|---|---|
| Y$MAL61_04 | MIG1 | AATTG |
| RAT$TH_03 | ARIX | AATTGA |
| PSAM$U7SN_04 | | ATTGA |
| HS$EGFR_15 | | TCAAT |
| AS$TWRKY_01 | WRKY3, WRKY4 | TTGAC |
| AS$WRKY_01 | WRKY1, WRKY2 | TTGAC |
| AS$WRKY_02 | WRKY1, WRKY2 | TTGAC |
| AS$WRKY_03 | WRKY1, WRKY2 | TTGAC |
| AS$WRKY_04 | WRKY1, WRKY2 | TTGAC |
| AT$RLK4_01 | WRKY18 | TTGAC |
| AT$RLK4_02 | WRKY18 | TTGAC |
| CAMV$35SR_01 | ASF-1, OBF4, OBF5, SARP, TGA1, TGA1a, TGA1b, TGA2, TGA2.1, TGA2.2, TGA3, TGA6, ZAP1 | TGACG |
| PIG$UPA_02 | CREB | TGACG |
| PIG$UPA_03 | CREB, CREBbeta | TGACG |
| HS$INS_04 | CREB | TGACG |
| HS$PL_12 | | TGACG |
| HS$CFOS_11 | AP-1, ATF | TGCGTCA |
| HS$PK_02 | | TGCGTCA |
| HS$PK_03 | AP-1, ATF3, c-Fos, c-Jun, CRE-BP1, CREB, CREBbeta | TGCGTCA |
| HS$VIP_01 | c-Fos, c-Jun, CRE-BP1, CREB | CGTCA |
| BOVIN$PPTA_01 | C/EBPdelta, CRE-BP2 | TGCGTCA |
| RAT$PDYN_01 | CREB | TGCGTCA |
| AS$PAX2_67 | Pax-2.1, Pax-2.2 | AATAAATGC |
| RAT$GLU_04 | | TATAT |

FIGURE 8F

| Identifier | Binding Factor | Sequence (Search Pattern) |
|---|---|---|
| HS$HH4_08 | HiNF-D, HiNF-M, HiNF-P, TFIID, TMF | TATAT |
| MOUSE$SRF_03 | SRF (504 AA) | TATAT |
| RAT$GLU_04 | | TATAT |
| HS$HH4_08 | HiNF-D, HiNF-M, HiNF-P, TFIID, TMF | TATAT |
| MOUSE$SRF_03 | SRF (504 AA) | TATAT |
| RAT$DBH_01 | ARIX, c-Fos, c-Jun, CREB, CREMtau | TGCGTCATTA (SEQ ID NO:41) |
| PSAM$U7SN_04 | | ATTGA |
| HS$EGFR_15 | | TCAAT |
| AS$TWRKY_01 | WRKY3, WRKY4 | TTGAC |
| AS$WRKY_01 | WRKY1, WRKY2 | TTGAC |
| AS$WRKY_02 | WRKY1, WRKY2 | TTGAC |
| AS$WRKY_03 | WRKY1, WRKY2 | TTGAC |
| AS$WRKY_04 | WRKY1, WRKY2 | TTGAC |
| AT$RLK4_01 | WRKY18 | TTGAC |
| AT$RLK4_02 | WRKY18 | TTGAC |
| CAMV$35SR_01 | ASF-1, OBF4, OBF5, SARP, TGA1, TGA1a, TGA1b, TGA2, TGA2.1, TGA2.2, TGA3, TGA6, ZAP1 | TGACG |
| PIG$UPA_02 | CREB | TGACG |
| PIG$UPA_03 | CREB, CREBbeta | TGACG |
| HS$INS_04 | CREB | TGACG |
| HS$PL_12 | | TGACG |
| HS$CFOS_11 | AP-1, ATF | TGCGTCA |
| HS$PK_02 | | TGCGTCA |
| HS$PK_03 | AP-1, ATF3, c-Fos, c-Jun, | TGCGTCA |

FIGURE 8G

| Identifier | Binding Factor | Sequence (Search Pattern) |
|---|---|---|
| | CRE-BP1, CREB, CREBbeta | |
| HS$VIP_01 | c-Fos, c-Jun, CRE-BP1, CREB | CGTCA |
| BOVIN$PPTA_01 | C/EBPdelta, CRE-BP2 | TGCGTCA |
| RAT$PDYN_01 | CREB | TGCGTCA |
| RAT$DBH_01 | ARIX, c-Fos, c-Jun, CREB, CREMtau | TGCGTCATTA (SEQ ID NO:42) |
| PSAM$U7SN_04 | | ATTGA |
| HS$EGFR_15 | | TCAAT |
| AS$TWRKY_01 | WRKY3, WRKY4 | TTGAC |
| AS$WRKY_01 | WRKY1, WRKY2 | TTGAC |
| AS$WRKY_02 | WRKY1, WRKY2 | TTGAC |
| AS$WRKY_03 | WRKY1, WRKY2 | TTGAC |
| AS$WRKY_04 | WRKY1, WRKY2 | TTGAC |
| AT$RLK4_01 | WRKY18 | TTGAC |
| AT$RLK4_02 | WRKY18 | TTGAC |
| CAMV$35SR_01 | ASF-1, OBF4, OBF5, SARP, TGA1, TGA1a, TGA1b, TGA2, TGA2.1, TGA2.2, TGA3, TGA6, ZAP1 | TGACG |
| PIG$UPA_02 | CREB | TGACG |
| PIG$UPA_03 | CREB, CREBbeta | TGACG |
| HS$INS_04 | CREB | TGACG |
| HS$PL_12 | | TGACG |
| HBV$HBVE_27 | CRE-BP1, CREB, pX | TGACGCAA |
| HS$CFOS_11 | AP-1, ATF | TGCGTCA |
| HS$PK_02 | | TGCGTCA |
| HS$PK_03 | AP-1, ATF3, c-Fos, c-Jun, | TGCGTCA |

FIGURE 8H

| Identifier | Binding Factor | Sequence (Search Pattern) |
|---|---|---|
| | CRE-BP1, CREB, CREBbeta | |
| HS$VIP_01 | c-Fos, c-Jun CRE-BP1, CREB, | CGTCA |
| BOVIN$PPTA_01 | C/EBPdelta, CRE-BP2 | TGCGTCA |
| RAT$PDYN_01 | CREB | TGCGTCA |
| AS$NCX_33 | Ncx | ACGTAAATTG (SEQ ID NO:43) |
| HS$EGFR_14 | | CAAAT |
| MAIZE$PMS1_01 | | CAAAT |
| HS$IGH_04 | | ATTTG |
| Y$MAL61_04 | MIG1 | AATTG |
| RAT$TH_03 | ARIX | AATTGA |
| PSAM$U7SN_04 | | ATTGA |
| HS$EGFR_15 | | TCAAT |
| AS$TWRKY_01 | WRKY3, WRKY4 | TTGAC |
| AS$WRKY_01 | WRKY1, WRKY2 | TTGAC |
| AS$WRKY_02 | WRKY1, WRKY2 | TTGAC |
| AS$WRKY_03 | WRKY1, WRKY2 | TTGAC |
| AS$WRKY_04 | WRKY1, WRKY2 | TTGAC |
| AT$RLK4_01 | WRKY18 | TTGAC |
| AT$RLK4_02 | WRKY18 | TTGAC |
| CAMV$35SR_01 | ASF-1, OBF4, OBF5, SARP, TGA1, TGA1a, TGA1b, TGA2, TGA2.1, TGA2.2, TGA3, TGA6, ZAP1 | TGACG |
| PIG$UPA_02 | CREB | TGACG |
| PIG$UPA_03 | CREB, CREBbeta | TGACG |
| HS$INS_04 | CREB | TGACG |
| HS$PL_12 | | TGACG |
| HBV$HBVE_27 | CRE-BP1, | TGACGCAA |

FIGURE 8I

| Identifier | Binding Factor | Sequence (Search Pattern) |
|---|---|---|
|  | CREB, pX |  |
| HS$CFOS_11 | AP-1, ATF | TGCGTCA |
| HS$PK_02 |  | TGCGTCA |
| HS$PK_03 | AP-1, ATF3, c-Fos, c-Jun, CRE-BP1, CREB, CREBbeta | TGCGTCA |
| HS$VIP_01 | c-Fos, c-Jun, CRE-BP1, CREB | CGTCA |
| BOVIN$PPTA_01 | C/EBPdelta, CRE-BP2 | TGCGTCA |
| RAT$PDYN_01 | CREB | TGCGTCA |
| HS$EGFR_14 |  | CAAAT |
| MAIZE$PMS1_01 |  | CAAAT |
| DROME$SNA_12 | Twi | CAAATG |
| HS$IGH_04 |  | ATTTG |
| XENLA$AC_05 | EMF1, MyoD | CATTTG |
| MOUSE$ACRG_01 | MyoD | CATTTG |
| HS$IRF1_02 | IPCS-BF | AAATGACGGC (SEQ ID NO:44) |
| HS$GMCSF_03 | YY1 | CATTT |
| MOUSE$IL4_01 | NF-CLE0a, NF-CLE0b | TCATTT |
| HS$UPA_05 | UEF-1 | CATGACAGC |
| HS$FN_05 | PEBP2 | ATGACCGCAA (SEQ ID NO:44) |
| HS$UPA_06 | Pbx-1a, Pbx-1b, Pbx-2, PKNOX1, PKNOX2, UEF-3 | TGACAG |
| AS$MEIS1_01 | Meis-1a, Meis-1b | TGACAG |
| AS$MEIS1_03 | Meis-1a, Meis-1b | TGACAG |
| AS$MEIS1_04 | Meis-1a, Meis-1b | TGACAG |
| AS$MEIS1_05 | Meis-1a, Meis-1b | TGACAG |
| AS$MEIS1_06 | Meis-1a, Meis-1b | TGACAG |
| AS$MEIS1_07 | Meis-1a, | TGACAG |

FIGURE 8J

| Identifier | Binding Factor | Sequence (Search Pattern) |
|---|---|---|
| | Meis-1b | |
| AS$MEIS1_08 | Meis-1a, Meis-1b | TGACAG |
| AS$MEIS1_14 | Meis-1a, Meis-1b | TGACAG |
| AS$MEIS1_19 | Meis-1a, Meis-1b | TGACAG |
| AS$MEIS1AHOXA9_01 | HOXA9, Meis-1a | TGACAG |
| AS$MEIS1AHOXA9_02 | HOXA9, Meis-1a | TGACAG |
| AS$MEIS1AHOXA9_03 | HOXA9, Meis-1a | TGACAG |
| AS$MEIS1AHOXA9_04 | HOXA9, Meis-1a | TGACAG |
| AS$MEIS1AHOXA9_05 | HOXA9, Meis-1a | TGACAG |
| AS$MEIS1AHOXA9_06 | HOXA9, Meis-1a | TGACAG |
| AS$MEIS1AHOXA9_09 | HOXA9, Meis-1a | TGACAG |
| AS$MEIS1AHOXA9_10 | HOXA9, Meis-1a | TGACAG |
| AS$MEIS1AHOXA9_13 | HOXA9, Meis-1a | TGACAG |
| AS$MEIS1BHOXA9_01 | HOXA9, Meis-1b | TGACAG |
| AS$MEIS1BHOXA9_02 | HOXA9, Meis-1b | TGACAG |
| AS$MEIS1BHOXA9_03 | HOXA9, Meis-1b | TGACAG |
| AS$MEIS1BHOXA9_04 | HOXA9, Meis-1b | TGACAG |
| AS$MEIS1BHOXA9_05 | HOXA9, Meis-1b | TGACAG |
| AS$MEIS1BHOXA9_06 | HOXA9, Meis-1b | TGACAG |
| AS$MEIS1BHOXA9_07 | HOXA9, Meis-1b | TGACAG |
| POT$PR10a_01 | PBF-1, PBF-2 (p24) | TGACA |
| AS$TGIF_01 | TGIF | TGTCA |
| AS$TGIF_02 | TGIF | TGTCA |
| AS$TGIF_03 | TGIF | TGTCA |
| AS$TGIF_04 | TGIF | TGTCA |
| AS$TGIF_05 | TGIF | TGTCA |
| AS$TGIF_06 | TGIF | TGTCA |

FIGURE 8K

| Identifier | Binding Factor | Sequence (Search Pattern) |
|---|---|---|
| AS$TGIF_07 | TGIF | TGTCA |
| AS$TGIF_08 | TGIF | TGTCA |
| AS$TGIF_10 | TGIF | TGTCA |
| AS$TGIF_11 | TGIF | TGTCA |
| AS$TGIF_12 | TGIF | TGTCA |
| AS$TGIF_13 | TGIF | TGTCA |
| AS$TGIF_14 | TGIF | TGTCA |
| AS$TGIF_15 | TGIF | TGTCA |
| HS$D1A_01 | Meis-2a, Meis-2b, Meis-2c, Meis-2d, TGIF | CTGTCA |
| AS$MEIS1_11 | Meis-1a, Meis-1b | CTGTCA |
| AS$MEIS1_12 | Meis-1a, Meis-1b | CTGTCA |
| POT$PR10a_01 | PBF-1, PBF-2 (p24) | TGTCA |
| HS$GG_12 | NF-E | CTGTC |
| DROME$EVE_10 | GAGA factor | CTGTC |
| MOUSE$M2EAK_03 | NF-Y | CAGCA |
| MOUSE$THY1_06 |  | CAGCAA |
| RAV0$RAV0_01 | C/EBPalpha | GCAAG |
| AMV$AMV_02 | C/EBPalpha | CTTGC |
| XENLA$ACY_01 | SRF | AAGAT |
| XENLA$ACY_01 | SRF | ATCTT |
| HS$GG_26 | GATA-1 | AGATTG |
| MOUSE$BMG_04 | GATA-1 | AATCT |
| PSAM$U7SN_04 |  | ATTGA |
| HS$EGFR_15 |  | TCAAT |
| AS$TWRKY_01 | WRKY3, WRKY4 | TTGAC |
| AS$WRKY_01 | WRKY1, WRKY2 | TTGAC |
| AS$WRKY_02 | WRKY1, WRKY2 | TTGAC |
| AS$WRKY_03 | WRKY1, WRKY2 | TTGAC |
| AS$WRKY_04 | WRKY1, WRKY2 | TTGAC |
| AT$RLK4_01 | WRKY18 | TTGAC |
| AT$RLK4_02 | WRKY18 | TTGAC |
| CAMV$35SR_01 | ASF-1, OBF4, OBF5, SARP, TGA1, | TGACG |

FIGURE 8L

| Identifier | Binding Factor | Sequence (Search Pattern) |
|---|---|---|
|  | TGA1a,TGA1b, TGA2, TGA2.1,TGA2.2, TGA3, TGA6, ZAP1 |  |
| PIG$UPA_02 | CREB | TGACG |
| PIG$UPA_03 | CREB, CREBbeta | TGACG |
| HS$INS_04 | CREB | TGACG |
| HS$PL_12 |  | TGACG |
| HBV$HBVE_27 | CRE-BP1, CREB, pX | TGACGCAA |
| HS$CFOS_11 | AP-1, ATF | TGCGTCA |
| HS$PK_02 |  | TGCGTCA |
| HS$PK_03 | AP-1, ATF3, c-Fos, c-Jun, CRE-BP1, CREB, CREBbeta | TGCGTCA |
| HS$VIP_01 | c-Fos, c-Jun, CRE-BP1, CREB | CGTCA |
| BOVIN$PPTA_01 | C/EBPdelta, CRE-BP2 | TGCGTCA |
| RAT$PDYN_01 | CREB | TGCGTCA |
| AS$NCX_33 | Ncx | ACGTAAATTG (SEQ ID NO:45) |
| HS$EGFR_14 |  | CAAAT |
| MAIZE$PMS1_01 |  | CAAAT |
| HS$IGH_04 |  | ATTTG |
| Y$MAL61_04 | MIG1 | AATTG |
| RAT$TH_03 | ARIX | AATTGA |
| PSAM$U7SN_04 |  | ATTGA |
| HS$EGFR_15 |  | TCAAT |
| TDNA$NOS_01 | ASF-1, OBF3.1, TGA1a, TGA1b | TGAGC |
| DROME$UBX_08 | Zeste | TGAGCG |
| DROME$E74_07 | Zeste | TGAGCG |
| DROME$E74_08 | Zeste | TGAGCG |
| DROME$WHLO_04 | Zeste | TGAGCG |
| DROME$ZESTE_02 | Zeste | TGAGCG |
| DROME$UBX_06 | Zeste | CGCTCA |

FIGURE 8M

| Identifier | Binding Factor | Sequence (Search Pattern) |
|---|---|---|
| DROME$EVE_04 | GAGA factor | CGCTC |
| DROME$EVE_08 | GAGA factor | CGCTC |
| DROME$EVE_10 | GAGA factor | CGCTC |
| MOUSE$MT1_06 | MTF-1 | TGCGCTC |
| HS$EGFR_14 | | CAAAT |
| MAIZE$PMS1_01 | | CAAAT |
| HS$IGH_04 | | ATTTG |
| Y$MAL61_04 | MIG1 | AATTG |
| RAT$TH_03 | ARIX | AATTGA |
| PSAM$U7SN_04 | | ATTGA |
| HS$EGFR_15 | | TCAAT |
| AS$TWRKY_01 | WRKY3, WRKY4 | TTGAC |
| AS$WRKY_01 | WRKY1, WRKY2 | TTGAC |
| AS$WRKY_02 | WRKY1, WRKY2 | TTGAC |
| AS$WRKY_03 | WRKY1, WRKY2 | TTGAC |
| AS$WRKY_04 | WRKY1, WRKY2 | TTGAC |
| AT$RLK4_01 | WRKY18 | TTGAC |
| AT$RLK4_02 | WRKY18 | TTGAC |
| CAMV$35SR_01 | ASF-1, OBF4, OBF5, SARP, TGA1, TGA1a, TGA1b, TGA2, TGA2.1, TGA2.2, TGA3, TGA6, ZAP1 | TGACG |
| PIG$UPA_02 | CREB | TGACG |
| PIG$UPA_03 | CREB, CREBbeta | TGACG |
| HS$INS_04 | CREB | TGACG |
| HS$PL_12 | | TGACG |
| HBV$HBVE_27 | CRE-BP1, CREB, Px | TGACGCAA |
| HS$CFOS_11 | AP-1, ATF | TGCGTCA |
| HS$PK_02 | | TGCGTCA |
| HS$PK_03 | AP-1, ATF3, c-Fos, c-Jun, CRE-BP1, CREB, CREBbeta | TGCGTCA |

FIGURE 8N

| Identifier | Binding Factor | Sequence (Search Pattern) |
|---|---|---|
| HS$VIP_01 | c-Fos, c-Jun, CRE-BP1, CREB | CGTCA |
| BOVIN$PPTA_01 | C/EBPdelta, CRE-BP2 | TGCGTCA |
| RAT$PDYN_01 | CREB | TGCGTCA |
| HS$EGFR_14 | | CAAAT |
| MAIZE$PMS1_01 | | CAAAT |
| HS$IGH_04 | | ATTTG |
| AS$ATHB1_26 | ATHB-1 | CAATTAATTG |
| AS$NKX61_02 | Nkx6-1 | TTAATTT |
| AS$ATHB1_26 | ATHB-1 | CAATTAATTG (SEQ ID NO:46) |
| Y$SUC2_02 | MIG1 | AATTA |
| RAT$DBH_01 | ARIX, c-Fos, c-Jun, CREB, CREMtau | AATTA |
| DROME$EN_01 | En, Eve, Ftz, Prd, Zen-1, Zen-2 | TCAATCAATT (SEQ ID NO:47) |
| DROME$EN_01 | En, Eve, Ftz, Prd, Zen-1, Zen-2 | TCAATTAAAT (SEQ ID NO:48) |
| DROME$EN_04 | En, POU2F2 (Oct-2.1) | TCAATTAAAT (SEQ ID NO:49) |
| AS$FTZ_47 | Ftz, Prd, Zen-1, Zen-2 | TCAATTAAAT (SEQ ID NO:50) |
| AS$EN_01 | En | TCAATTAAAT (SEQ ID NO:51) |
| EN$CONS | Abd-A, Abd-B, BarH1, Cf1a, Cut, Ems, En, Lab, PDM-1, Zfh-1, Zfh-2 | TCAATTAAAT (SEQ ID NO:52) |
| Y$MEL1_02 | MIG1 | ATTAA |
| CHICK$MGF_01 | Gbx2 | ATTAA |
| DROME$EN_05 | En | TCAATTAAA |
| DROME$ADH_29 | | CTCAATTAAT (SEQ ID NO:53) |

FIGURE 8O

| Identifier | Binding Factor | Sequence (Search Pattern) |
|---|---|---|
| CHICK$MGF_02 | Gbx2 | TTAAT |
| UBX$CONS_02 | Ubx | TTAATKG |
| MOUSE$HOXC8_04 | | TTAATTG |
| CHICK$MGF_02 | Gbx2 | TTAAT |
| AS$NKX61_01 | Nkx6-1 | TTAATTG |
| AS$NKX61_02 | Nkx6-1 | TTAATTG |
| AS$NKX61_03 | Nkx6-1 | TTAATTG |
| AS$NKX61_05 | IPF1, Nkx6-1 | TTAATTG |
| AS$NKX61_06 | Nkx6-1 | TTAATTG |
| AS$NKX61_08 | Nkx6-1 | TTAATTG |
| AS$NKX61_09 | Nkx6-1 | TTAATTG |
| AS$NKX61_10 | Nkx6-1 | TTAATTG |
| Y$MEL1_02 | MIG1 | ATTAA |
| BOVIN$RHO_02 | Crx | CAATTAA |
| CHICK$MGF_01 | Gbx2 | ATTAA |
| Y$SUC2_02 | MIG1 | AATTA |
| RAT$DBH_01 | ARIX, c-Fos, c-Jun, CREB, CREMtau | AATTA |
| Y$MAL61_04 | MIG1 | AATTG |
| RAT$TH_03 | ARIX | AATTGA |
| PSAM$U7SN_04 | | ATTGA |
| HS$EGFR_15 | | TCAAT |
| AS$TWRKY_01 | WRKY3, WRKY4 | TTGAC |
| AS$WRKY_01 | WRKY1, WRKY2 | TTGAC |
| AS$WRKY_02 | WRKY1, WRKY2 | TTGAC |
| AS$WRKY_03 | WRKY1, WRKY2 | TTGAC |
| AS$WRKY_04 | WRKY1, WRKY2 | TTGAC |
| AT$RLK4_01 | WRKY18 | TTGAC |
| AT$RLK4_02 | WRKY18 | TTGAC |

| Identifier | Binding Factor | Sequence (Search Pattern) |
|---|---|---|
| HS$A11COL_02 | | GTGGTTAGC |
| MOUSE$IAP_01 | | GTGGT |
| MOUSE$IAP_03 | EBP-80 | GTGGT |
| EBV$IR4_04 | R | CACCAC |
| EBV$IR4_05 | R | CACCAC |

FIGURE 8P

| Identifier | Binding Factor | Sequence (Search Pattern) |
|---|---|---|
| HS$PR264_01 | c-Myb | GGTGAG |
| HS$APOA2_06 | | TCACC |
| TDNA$NOS_01 | ASF-1, OBF3.1, TGA1a, TGA1b | TGAGC |
| DROME$UBX_08 | Zeste | TGAGCG |
| DROME$E74_07 | Zeste | TGAGCG |
| DROME$E74_08 | Zeste | TGAGCG |
| DROME$WHLO_04 | Zeste | TGAGCG |
| DROME$ZESTE_02 | Zeste | TGAGCG |
| DROME$UBX_06 | Zeste | CGCTCA |
| DROME$EVE_04 | GAGA factor | CGCTC |
| DROME$EVE_08 | GAGA factor | CGCTC |
| DROME$EVE_10 | GAGA factor | CGCTC |
| AS$PAX4_29 | Pax-4a | CATTCCCAGACG (SEQ ID NO:54) |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:55) |
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |

FIGURE 8Q

| Identifier | Binding Factor | Sequence (Search Pattern) |
|---|---|---|
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:56) |
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:57) |
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| CHICK$BAG_03 | | TGCCC |
| RAT$VEGF_02 | ER-alpha, ER-beta | TGCCC |

FIGURE 8R

| Identifier | Binding Factor | Sequence (Search Pattern) |
|---|---|---|
| HS$APAF1_01 | p53 | CGACAAGCCC (SEQ ID NO:58) |
| AS$HOXA3_13 | HOXA3 | CATGTTGGG |
| AS$FTZ_56 | Ftz | CCGACA |
| HSV1$GD_01 | ICP4 | CCGAC |
| AT$COR15A_01 | ANT, CBF1, CBF2, CBF3 | CCGAC |
| AT$RD29B_01 | CBF1 | CCGAC |
| AT$RD29A_01 | CBF1, DREB1A, DREB2A | CCGAC |
| AT$COR78_01 | ANT, CBF1, CBF2, CBF3 | CCGAC |
| AT$COR15B_01 | CBF1, CBF2, CBF3 | CCGAC |
| HS$CGB_03 |  | CGGGCATCCTG (SEQ ID NO:59) |
| HS$CETP_02 | LXR-alpha, LXR-beta, RXR-alpha | CGGGCA |
| HS$CYCD1_15 | Sp1, Sp2, Sp3, Sp4 | GCCCG |
| CHICK$BAG_03 |  | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| CHICK$BAG_03 |  | TGCCC |
| RAT$VEGF_02 | ER-alpha, ER-beta | TGCCC |
| ASPN$ABAA_03 | abaA | CATTCT |
| ASPN$ABAA_04 | abaA | CATTCT |
| ASPN$ABAA_05 | abaA | CATTCT |
| ASPN$BRLA_03 | abaA | CATTCT |
| ASPN$RODA_05 | abaA | CATTCT |
| ABAA$CONS_01 | abaA | CATTCY |
| ASPN$BRLA_05 | abaA | CATTCT |
| ASPN$YA_02 | abaA | AGAATG |

FIGURE 8S

| Identifier | Binding Factor | Sequence (Search Pattern) |
| --- | --- | --- |
| I$HSF_01 | HSF | AGAAN |
| F$HSF_01 | HSF | AGAAN |
| SV$SV40_37 | | CTGGG |
| RAT$IGFBP2_03 | Sp1 | TGGGCGTGTG (SEQ ID NO:60) |
| SV$SV40_63 | T-Ag | TGGGC |
| Y$HOP1_01 | | TGGGCGGCT |
| RAT$BMHC_04 | NFe | TGACGCCCA |
| MOUSE$GLUT4_03 | Sp1 | GGGCGT |
| HS$U2SN_04 | Sp1 | ACGCCC |
| HS$CD11B_01 | Sp1 | CGCCC |
| AS$PAX4_29 | Pax-4a | CATTCCCAGACG (SEQ ID NO:63) |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:64) |
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |
| CHICK$BAG_09 | CTF | TCTGGGCA |
| SV$SV40_37 | | CTGGG |
| RAT$TAT_06 | NRF-1 | CATGCGCAG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| MOUSE$PIDD_01 | p53 | GGACATGTCT (SEQ ID NO:65) |

FIGURE 8T

| Identifier | Binding Factor | Sequence (Search Pattern) |
|---|---|---|
| CHICK$BAG_03 | | TGCCC |
| RAT$VEGF_02 | ER-alpha, ER-beta | TGCCC |
| RAT$SPI23_02 | C/EBPalpha | CCCAGAAAT |
| AS$TGIF_09 | TGIF | TGTCT |
| CHICK$BAG_04 | | TCTGGGCA |
| CHICK$BAG_09 | CTF | TCTGGGCA |
| SV$SV40_37 | | CTGGG |
| SV$SV40_63 | T-Ag | TGGGC |
| CHICK$BAG_03 | | GGGCA |
| RAT$NF1_01 | LF-A1 | GGGCA |
| HS$CATHD_01 | ER-alpha, Sp1 | GGGCA |
| RAT$VEGF_01 | ER-alpha, ER-beta | GGGCA |
| CHICK$BAG_03 | | TGCCC |
| RAT$VEGF_02 | ER-alpha, ER-beta | TGCCC |
| AS$STAT5A_44 | STAT5A | TTCTCGACA |
| I$HSF_01 | HSF | AGAAN |
| F$HSF_01 | HSF | AGAAN |
| HS$TERT_01 | c-Myc | CACCGT |
| WHEAT$H4_01 | ssDBP-1, ssDBP-2 | CCACGTCACCG (SEQ ID NO:66) |
| CREB$CONS_02 | CREB, CREBbeta, deltaCREB | GNTGACGY |
| AS$BZIP911_27 | bZIP911 | GGTGACGTGTAC (SEQ ID NO:67) |
| AS$BZIP911_28 | bZIP911 | GGTGACGTGTAC (SEQ ID NO:68) |
| AS$BZIP911_30 | bZIP911 | GGTGACGTGTAC (SEQ ID NO:68) |
| HS$APOA2_06 | | TCACC |
| AD$MLP_10 | USF | CACGTGACC |
| AD$E4_02 | E4F1 | GTGACGT |
| AD$E4_03 | CRE-BP1, E4F1 | GTGACGT |
| AD$E4_05 | E4F1 | GTGACGT |
| AD5$E1A_14 | ATF | GTGACGT |

FIGURE 8U

| Identifier | Binding Factor | Sequence (Search Pattern) |
|---|---|---|
| AD5$E1A_16 | ATF | GTGACGT |
| AD5$E1A_21 | ATF | GTGACGT |
| HS$M1B7_03 |  | GTGACG |
| HS$P53_03 | Pax-2, Pax-5, Pax-8 | GTGAC |
| HS$MMP1_06 |  | GTCAC |
| CAMV$35SR_01 | ASF-1, OBF4, OBF5, SARP, TGA1, TGA1a, TGA1b, TGA2, TGA2.1, TGA2.2, TGA3, TGA6, ZAP1 | TGACG |
| HS$GHA_03 | GR, GR-alpha, GR-beta | TGACGT |
| PIG$UPA_02 | CREB | TGACG |
| PIG$UPA_03 | CREB, CREBbeta | TGACG |
| HS$VIP_04 | ATF | TGACGT |
| CAMV$35SR_03 | HBP-1, HBP-1a, HBP-1a(1), HBP-1a(c14), HBP-1b, HBP-1b(c1) | TGACGT |
| HS$INS_04 | CREB | TGACG |
| RAT$TH2A_01 |  | TGACGT |
| AT$DBP_01 | GBF1, HBP-1a, HBP-1b, OBF3.1, OBF3.2, OBF4, OBF5, TGA1, TGA3, TGA6 | TGACGT |

FIGURE 8V

| Identifier | Binding Factor | Sequence (Search Pattern) |
|---|---|---|
| PEA$LEGA_01 | HBP-1a, HBP-1b | TGACGT |
| HS$PL_12 | | TGACG |
| HT1$HTLV1_20 | TAF-I, TAF-II, Tax | TGACGT |
| BZIP910$CONS_01 | bZIP910 | TGACGTG |
| BZIP910$CONS_02 | bZIP910 | TGACGT |
| AD$E4_16 | ATF, atf1, ATF3, c-Jun, CRE-BP1, CREB, deltaCREB, EivF, TREB-1 | ACGTCA |
| RAT$TH_02 | ATF | ACGTCA |
| HS$VIP_01 | c-Fos, c-Jun, CRE-BP1, CREB | CGTCA |
| TDNA$NOS_02 | HBP-1, HBP-1a, HBP-1b | ACGTCA |
| RAT$TH2B_04 | | ACGTCA |
| RICE$NR1_01 | HBP-1a, HBP-1b | ACGTCA |
| Y$LPD1_02 | ATF | ACGTCA |
| HS$ENO1_01 | HIF-1 | GACGTG |
| AT$GST6_02 | OBF4 | GACGTG |
| RICE$EM_01 | OSBZ8, TRAB1 | ACGTG |
| RICE$EM_02 | OSBZ8 | ACGTG |
| HS$ET1_03 | HIF-1 | GCACGT |
| AS$mEMBP_15 | EmBP-1a | CACGT |
| MOUSE$MT1_01 | Sp1 | TGCAC |
| MOUSE$MT1_01 | Sp1 | TGCAC |
| RAT$CYTOP_04 | AhR, Arnt | CACGC |
| DAUCE$DC3_04 | DPBF-1, DPBF-2 | CACGCG |
| AS$AHRARNT_50 | AhR, Arnt | GCGTG |
| AS$DSC1_01 | DSC1 | ACGCGT |
| Y$CDC9_02 | DSC1 | ACGCGT |
| Y$POL1_01 | MCBF | ACGCGT |

FIGURE 8W

SEQUENCE LISTING

<160> NUMBER OF SEQ ID NOS: 68

<210> SEQ ID NO 1
<211> LENGTH: 21
<212> TYPE: DNA
<213> ORGANISM: Artificial Sequence
<220> FEATURE:
<223> OTHER INFORMATION: A synthetic primer

<400> SEQUENCE: 1
tttttgaagc gaaggttgtg g                                           21

<210> SEQ ID NO 2
<211> LENGTH: 21
<212> TYPE: DNA
<213> ORGANISM: Artificial Sequence
<220> FEATURE:
<223> OTHER INFORMATION: A synthetic primer

<400> SEQUENCE: 2
cacacacagt tcgcctcttt g                                           21

<210> SEQ ID NO 3
<211> LENGTH: 32
<212> TYPE: DNA
<213> ORGANISM: Artificial Sequence
<220> FEATURE:
<223> OTHER INFORMATION: A synthetic probe

<400> SEQUENCE: 3
atctggatac cgggaaaacg ctgggcgtta at                               32

<210> SEQ ID NO 4
<211> LENGTH: 22
<212> TYPE: DNA
<213> ORGANISM: Artificial Sequence
<220> FEATURE:
<223> OTHER INFORMATION: A synthetic primer

<400> SEQUENCE: 4
gacgatgttg aaagcatacc ac                                          22

<210> SEQ ID NO 5
<211> LENGTH: 22
<212> TYPE: DNA
<213> ORGANISM: Artificial Sequence
<220> FEATURE:
<223> OTHER INFORMATION: A synthetic primer

<400> SEQUENCE: 5
cacaaccaaa gaaatagcca cc                                          22

<210> SEQ ID NO 6
<211> LENGTH: 27
<212> TYPE: DNA
<213> ORGANISM: Artificial Sequence
<220> FEATURE:
<223> OTHER INFORMATION: A synthetic probe

<400> SEQUENCE: 6
agtgacaaca tggaacacat acctccg                                     27

<210> SEQ ID NO 7
<211> LENGTH: 22
<212> TYPE: DNA
<213> ORGANISM: Artificial Sequence -continued

```
<220> FEATURE:
<223> OTHER INFORMATION: A synthetic probe

<400> SEQUENCE: 7
taccctcgag aacggtgacg tg                                           22

<210> SEQ ID NO 8
<211> LENGTH: 25
<212> TYPE: DNA
<213> ORGANISM: Artificial Sequence
<220> FEATURE:
<223> OTHER INFORMATION: A synthetic probe

<400> SEQUENCE: 8
ggagatgcgc ctgtctcctg gaatg                                        25

<210> SEQ ID NO 9
<211> LENGTH: 32
<212> TYPE: DNA
<213> ORGANISM: Artificial Sequence
<220> FEATURE:
<223> OTHER INFORMATION: A synthetic probe

<400> SEQUENCE: 9
gcatcgatca gagtgtgttg gttttttgtg tg                                32

<210> SEQ ID NO 10
<211> LENGTH: 45
<212> TYPE: RNA
<213> ORGANISM: Artificial Sequence
<220> FEATURE:
<223> OTHER INFORMATION: A synthetic primer

<400> SEQUENCE: 10
gcacgagggc gacugucaug aucgaugcau cugagcucuu uauua                  45

<210> SEQ ID NO 11
<211> LENGTH: 20
<212> TYPE: DNA
<213> ORGANISM: Artificial Sequence
<220> FEATURE:
<223> OTHER INFORMATION: A synthetic primer

<400> SEQUENCE: 11
tgcagatgag gttggactca                                              20

<210> SEQ ID NO 12
<211> LENGTH: 21
<212> TYPE: DNA
<213> ORGANISM: Artificial Sequence
<220> FEATURE:
<223> OTHER INFORMATION: A synthetic primer

<400> SEQUENCE: 12
caagtctcgc tctcaaattg c                                            21

<210> SEQ ID NO 13
<211> LENGTH: 18
<212> TYPE: DNA
<213> ORGANISM: Artificial Sequence
<220> FEATURE:
<223> OTHER INFORMATION: A synthetic primer

<400> SEQUENCE: 13
gcacgagggc gactgtca                                                18
```

```
<210> SEQ ID NO 14
<211> LENGTH: 25
<212> TYPE: DNA
<213> ORGANISM: Artificial Sequence
<220> FEATURE:
<223> OTHER INFORMATION: A synthetic primer

<400> SEQUENCE: 14
acctcttctt ccgtctcctc cttca                                              25

<210> SEQ ID NO 15
<211> LENGTH: 99
<212> TYPE: DNA
<213> ORGANISM: Artificial Sequence
<220> FEATURE:
<223> OTHER INFORMATION: A synthetic oligonucleotide

<400> SEQUENCE: 15
agtcagggca agtcagtggc aagtcagggc agtcagggca gtcagggcaa gtcagggcaa        60
gtcagggcaa gtcagggcaa gtcagggcaa gtcagggca                               99

<210> SEQ ID NO 16
<211> LENGTH: 100
<212> TYPE: DNA
<213> ORGANISM: Artificial Sequence
<220> FEATURE:
<223> OTHER INFORMATION: A synthetic oligonucleotide

<400> SEQUENCE: 16
gaattgacgc atatattgac gcatattgac gcaaattgac gcaaatgaca gcaagattga        60
cgcaaattga gcgcaaattg acgcaaatta attgacgcat                             100

<210> SEQ ID NO 17
<211> LENGTH: 98
<212> TYPE: DNA
<213> ORGANISM: Artificial Sequence
<220> FEATURE:
<223> OTHER INFORMATION: A synthetic oligonucleotide

<400> SEQUENCE: 17
ctgatgcaat ctgatgcaat ctgatgcaat ctgatgcaat ctgatgcaat ctgagcaatc        60
tgatgcaatc tgatgcaata tgatgaatgt gatgcaat                                98

<210> SEQ ID NO 18
<211> LENGTH: 93
<212> TYPE: DNA
<213> ORGANISM: Artificial Sequence
<220> FEATURE:
<223> OTHER INFORMATION: A synthetic oligonucleotide

<400> SEQUENCE: 18
tggtgagcgt ctgggcatgt ctgggcatgt ctgggcatgt ctgggcatgt cgggcattct        60
gggcgtctgg gcatgtctgg gcatgtctgg gca                                     93

<210> SEQ ID NO 19
<211> LENGTH: 100
<212> TYPE: DNA
<213> ORGANISM: Artificial Sequence
<220> FEATURE:
<223> OTHER INFORMATION: A synthetic oligonucleotide
```

```
<400> SEQUENCE: 19
gctgatgcaa tctgatgcaa tctgatgcaa tctgatgcaa tctgatgcaa tctgagcaat      60
ctgatgcaat ctgatgcaat atgatgaatg tgatgcaatt                            100

<210> SEQ ID NO 20
<211> LENGTH: 100
<212> TYPE: DNA
<213> ORGANISM: Artificial Sequence
<220> FEATURE:
<223> OTHER INFORMATION: A synthetic oligonucleotide

<400> SEQUENCE: 20
gctgatgcaa tctgatgcaa tctgatgcaa tctgatgcaa tctgatgcaa tctgagcaat      60
ctgatgcaat ctgatgcaat atgatgaatg tgatgcaatt                            100

<210> SEQ ID NO 21
<211> LENGTH: 60
<212> TYPE: DNA
<213> ORGANISM: Artificial Sequence
<220> FEATURE:
<223> OTHER INFORMATION: A synthetic oligonucleotide

<400> SEQUENCE: 21
attgacgcgg attgacgcgg attgacgcgg attgacgcgg attgacgcgg attgacgcgg      60

<210> SEQ ID NO 22
<211> LENGTH: 79
<212> TYPE: DNA
<213> ORGANISM: Artificial Sequence
<220> FEATURE:
<223> OTHER INFORMATION: A synthetic oligonucleotide

<400> SEQUENCE: 22
attgacgcgg attgacgcgg attgacgcgg attgacgcgg attgacgcgg attgacgcgg      60
attgacgcgg attgacgcg                                                   79

<210> SEQ ID NO 23
<211> LENGTH: 83
<212> TYPE: DNA
<213> ORGANISM: Artificial Sequence
<220> FEATURE:
<223> OTHER INFORMATION: A synthetic oligonucleotide

<400> SEQUENCE: 23
ctcgagaacg gtgacgtgca cgcgtgggcg gagccatcac gcaggttgct atataagcag      60
agctcgttta gtgaaccgtc aga                                              83

<210> SEQ ID NO 24
<211> LENGTH: 182
<212> TYPE: DNA
<213> ORGANISM: Artificial Sequence
<220> FEATURE:
<223> OTHER INFORMATION: A synthetic oligonucleotide

<400> SEQUENCE: 24
agtcagggca agtcagtggc aagtcagggc agtcagggca gtcagggcaa gtcagggcaa      60
gtcagggcaa gtcagggcaa gtcagggcaa gtcagggcac tcgagaacgg tgacgtgcac     120
gcgtgggcgg agccatcacg caggttgcta tataagcaga gctcgtttag tgaaccgtca     180
ga                                                                    182
```

<210> SEQ ID NO 25
<211> LENGTH: 179
<212> TYPE: DNA
<213> ORGANISM: Artificial Sequence
<220> FEATURE:
<223> OTHER INFORMATION: A synthetic oligonucleotide

<400> SEQUENCE: 25
gaattgacgc atatattgac gcatattgac gcaaattgac gcaaatgaca gcaagattga      60
cgcaaattga gcgcaaattg acgcaaatta attgacctcg agaacggtga cgtgcacgcg     120
tgggcggagc catcacgcag gttgctatat aagcagagct cgtttagtga accgtcaga     179

<210> SEQ ID NO 26
<211> LENGTH: 181
<212> TYPE: DNA
<213> ORGANISM: Artificial Sequence
<220> FEATURE:
<223> OTHER INFORMATION: A synthetic oligonucleotide

<400> SEQUENCE: 26
ctgatgcaat ctgatgcaat ctgatgcaat ctgatgcaat ctgatgcaat ctgagcaatc      60
tgatgcaatc tgatgcaata tgatgaatgt gatgcaatct cgagaacggt gacgtgcacg     120
cgtgggcgga gccatcacgc aggttgctat ataagcagag ctcgtttagt gaaccgtcag     180
a                                                                      181

<210> SEQ ID NO 27
<211> LENGTH: 178
<212> TYPE: DNA
<213> ORGANISM: Artificial Sequence
<220> FEATURE:
<223> OTHER INFORMATION: A synthetic oligonucleotide

<400> SEQUENCE: 27
gtggtgagcg tctgggcatg tctgggcatg tctgggcatg tctgggcatg tcgggcattc      60
tgggcgtctg ggcatgtctg ggcatgtctg ggcatctcga gaacggtgac gtgcacgcgt     120
gggcggagcc atcacgcagg ttgctatata agcagagctc gtttagtgaa ccgtcaga      178

<210> SEQ ID NO 28
<211> LENGTH: 183
<212> TYPE: DNA
<213> ORGANISM: Artificial Sequence
<220> FEATURE:
<223> OTHER INFORMATION: A synthetic oligonucleotide

<400> SEQUENCE: 28
gctgatgcaa tctgatgcaa tctgatgcaa tctgatgcaa tctgatgcaa tctgagcaat      60
ctgatgcaat ctgatgcaat atgatgaatg tgatgcaatt ctcgagaacg gtgacgtgca     120
cgcgtgggcg gagccatcac gcaggttgct atataagcag agctcgttta gtgaaccgtc     180
aga                                                                    183

<210> SEQ ID NO 29
<211> LENGTH: 183
<212> TYPE: DNA
<213> ORGANISM: Artificial Sequence
<220> FEATURE:
<223> OTHER INFORMATION: A synthetic oligonucleotide

<400> SEQUENCE: 29
gctgatgcaa tctgatgcaa tctgatgcaa tctgatgcaa tctgatgcaa tctgagcaat        60
ctgatgcaat ctgatgcaat atgatgaatg tgatgcaatt ctcgagaacg gtgacgtgca       120
cgcgtgggcg gagccatcac gcaggttgct atataagcag agctcgttta gtgaaccgtc       180
aga                                                                    183

<210> SEQ ID NO 30
<211> LENGTH: 143
<212> TYPE: DNA
<213> ORGANISM: Artificial Sequence
<220> FEATURE:
<223> OTHER INFORMATION: A synthetic oligonucleotide

<400> SEQUENCE: 30
attgacgcgg attgacgcgg attgacgcgg attgacgcgg attgacgcgg attgacgcgg        60
ctcgagaacg gtgacgtgca cgcgtgggcg gagccatcac gcaggttgct atataagcag       120
agctcgttta gtgaaccgtc aga                                               143

<210> SEQ ID NO 31
<211> LENGTH: 12
<212> TYPE: DNA
<213> ORGANISM: Artificial Sequence
<220> FEATURE:
<223> OTHER INFORMATION: A synthetic oligonucleotide

<400> SEQUENCE: 31
cattcccaga cg                                                           12

<210> SEQ ID NO 32
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 32
ggacatgtct                                                              10

<210> SEQ ID NO 33
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 33
ggacatgtct                                                              10

<210> SEQ ID NO 34
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 34
ggacatgtct                                                              10

<210> SEQ ID NO 35
<211> LENGTH: 10
<212> TYPE: DNA
<213> ORGANISM: Artificial Sequence

```
<220> FEATURE:
<223> OTHER INFORMATION: A synthetic oligonucleotide

<400> SEQUENCE: 35
cgacaagccc                                                          10

<210> SEQ ID NO 36
<211> LENGTH: 11
<212> TYPE: DNA
<213> ORGANISM: Artificial Sequence
<220> FEATURE:
<223> OTHER INFORMATION: A synthetic oligonucleotide

<400> SEQUENCE: 36
cgggcatcct g                                                        11

<210> SEQ ID NO 37
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 37
tgggcgtgtg                                                          10

<210> SEQ ID NO 38
<211> LENGTH: 12
<212> TYPE: DNA
<213> ORGANISM: Artificial Sequence
<220> FEATURE:
<223> OTHER INFORMATION: A synthetic oligonucleotide

<400> SEQUENCE: 38
cattcccaga cg                                                       12

<210> SEQ ID NO 39
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 39
ggacatgtct                                                          10

<210> SEQ ID NO 40
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 40
ggacatgtct                                                          10

<210> SEQ ID NO 41
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 41
tgcgtcatta                                                          10
```

```
<210> SEQ ID NO 42
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 42
tgcgtcatta                                                         10

<210> SEQ ID NO 43
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 43
acgtaaattg                                                         10

<210> SEQ ID NO 44
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 44
aaatgacggc                                                         10

<210> SEQ ID NO 45
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 45
atgaccgcaa                                                         10

<210> SEQ ID NO 46
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 46
acgtaaattg                                                         10

<210> SEQ ID NO 47
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 47
caattaattg                                                         10

<210> SEQ ID NO 48
<211> LENGTH: 10
<212> TYPE: DNA
<213> ORGANISM: Artificial Sequence
<220> FEATURE:
<223> OTHER INFORMATION: A synthetic oligonucleotide
```

```
<400> SEQUENCE: 48
caattaattg                                                              10

<210> SEQ ID NO 49
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 49
tcaatcaatt                                                              10

<210> SEQ ID NO 50
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 50
tcaattaaat                                                              10

<210> SEQ ID NO 51
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 51
tcaattaaat                                                              10

<210> SEQ ID NO 52
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 52
tcaattaaat                                                              10

<210> SEQ ID NO 53
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 53
tcaattaaat                                                              10

<210> SEQ ID NO 54
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 54
tcaattaaat                                                              10
```

```
<210> SEQ ID NO 55
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 55
ctcaattaat                                                                 10

<210> SEQ ID NO 56
<211> LENGTH: 12
<212> TYPE: DNA
<213> ORGANISM: Artificial Sequence
<220> FEATURE:
<223> OTHER INFORMATION: A synthetic oligonucleotide

<400> SEQUENCE: 56
cattcccaga cg                                                              12

<210> SEQ ID NO 57
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 57
ggacatgtct                                                                 10

<210> SEQ ID NO 58
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 58
ggacatgtct                                                                 10

<210> SEQ ID NO 59
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 59
ggacatgtct                                                                 10

<210> SEQ ID NO 60
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 60
cgacaagccc                                                                 10

<210> SEQ ID NO 61
<211> LENGTH: 11
<212> TYPE: DNA
<213> ORGANISM: Artificial Sequence
<220> FEATURE:
<223> OTHER INFORMATION: A synthetic oligonucleotide
```

-continued

```
<400> SEQUENCE: 61
cgggcatcct g                                                          11

<210> SEQ ID NO 62
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 62
tgggcgtgtg                                                            10

<210> SEQ ID NO 63
<211> LENGTH: 12
<212> TYPE: DNA
<213> ORGANISM: Artificial Sequence
<220> FEATURE:
<223> OTHER INFORMATION: A synthetic oligonucleotide

<400> SEQUENCE: 63
cattcccaga cg                                                         12

<210> SEQ ID NO 64
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 64
ggacatgtct                                                            10

<210> SEQ ID NO 65
<211> LENGTH: 10
<212> TYPE: DNA
<213> ORGANISM: Artificial Sequence
<220> FEATURE:
<223> OTHER INFORMATION: A synthetic oligonucleotide

<400> SEQUENCE: 65
ggacatgtct                                                            10

<210> SEQ ID NO 66
<211> LENGTH: 12
<212> TYPE: DNA
<213> ORGANISM: Artificial Sequence
<220> FEATURE:
<223> OTHER INFORMATION: A synthetic oligonucleotide

<400> SEQUENCE: 66
ggtgacgtgt ac                                                         12

<210> SEQ ID NO 67
<211> LENGTH: 12
<212> TYPE: DNA
<213> ORGANISM: Artificial Sequence
<220> FEATURE:
<223> OTHER INFORMATION: A synthetic oligonucleotide

<400> SEQUENCE: 67
ggtgacgtgt ac                                                         12
```

```
<210> SEQ ID NO 68
<211> LENGTH: 12
<212> TYPE: DNA
<213> ORGANISM: Artificial Sequence
<220> FEATURE:
<223> OTHER INFORMATION: A synthetic oligonucleotide

<400> SEQUENCE: 68
ggtgacgtgt ac                                                            12
```

AAV-MEDIATED EXPRESSION USING A SYNTHETIC PROMOTER AND ENHANCER

CROSS-REFERENCE TO RELATED APPLICATIONS

This application is a U.S. National Stage Filing under 35 U.S.C. 371 from International Application No. PCT/US2017/021124, filed on 7 Mar. 2017, and published as WO 2017/155973 on 14 Sep. 2017, which application claims the benefit of the filing date of U.S. application Ser. No. 62/304,656, filed on Mar. 7, 2016, the disclosures of which are incorporated by reference herein.

STATEMENT OF GOVERNMENT RIGHTS

The invention was made with government support under grant HU 08902 awarded by the National Institutes of Health. The Government has certain rights in the invention.

BACKGROUND

Cystic fibrosis (CF) is a lethal, autosomal-recessive disorder that affects at least 30,000 people in the U.S. alone (O'Sullivan et al., 2009), The genetic basis of CF is mutation of a single gene that encodes the cystic fibrosis transmembrane conductance regulator (CFTR) (Riordan et al., 1989; Rommens et al., 1989). This results in a defective CFTR protein and consequent abnormalities in the transport of electrolytes and fluids in multiple organs (Welsh, 1990; Rowe et al., 2005). The most life-threatening outcome is CF pulmonary disease, which is characterized by viscous mucous secretions and chronic bacterial infections (Welsh, 1990). With improvement in patient care and advances in pharmacologic therapies for CF, the lifespan of CF patients has steadily been extended over the past decades; however, the quality of life for CF patients remains poor, and medications that alleviate pulmonary complications are expensive and efficacious only in select patients. Since lung disease is the major cause of mortality in CF patients and the genetic basis is a single-gene defect, gene therapy for CF lung disease has the potential to cure all CF patients, regardless of their CFTR mutation. Thus, clinical trials for CF lung gene therapy were initiated in the mid-1990s. However, all trials to date have been unsuccessful (Sumner-Jones et al., 2010). The underlying reason is that the vectors available for gene transfer to the human airway epithelium (HAE) are inefficient (Mueller & Flute, 2008; Griesenbach & Alton, 2009; Griesenbach et al., 2010).

Adeno-associated virus (AAV), a member of the human parvovirus family, is a non-pathogenic virus that depends on helper viruses for its replication. For this reason, rAAV vectors are among the most frequently used in gene therapy pre-clinical studies and clinical trials (Carter, 2005; Wu et al., 2006; Daya & Berns, 2008). Indeed, CF lung disease clinical trials with rAAV2 demonstrated both a good safety profile and long persistence of the viral genome in airway tissue (as assessed by biopsy) relative to other gene transfer agents (such as recombinant adenovirus). Nevertheless, gene transfer failed to improve lung function in CF patients because transcription of the rAAV vector-derived CFTR mRNA was not detected (Flotte, 2001; Aitken et al., 2001; Wagner et al., 2002; Moss et al., 2007; Duan et al., 2000). These observations are consistent with later studies on rAAV transduction using an in vitro model of the polarized HAE, in which the cells are grown at an air-liquid interface (ALI) (Flotte, 2001; Duan et al., 1998). The poor efficiency of rAAV2 as a vector for CFTR expression in the HAE is largely due to two major barriers: 1) inefficient post-entry processing of the virus, and 2) the limited packaging capacity of rAAV.

The initial preclinical studies with rAAV2-CFTR that supported the first clinical trial in CF patients were performed in rhesus monkeys. These studies demonstrated that viral DNA and transgene-derived CFTR mRNA persisted in the lung for long periods following rAAV2-mediated CFTR gene transfer (Conrad et al., 1996), However, later studies comparing the efficiency of rAAV2 transduction between human and rhesus monkey airway epithelial ALI cultures demonstrated that the tropism of rAAV2 for apical transduction was significantly higher in the rhesus monkeys cultures than in their human counterparts (Liu et al., 2007), likely due to species-specific differences in the AAV2 receptors and co-receptors that exist on the apical surface. In studies of polarized HAE, the majority of AAV2 virions were internalized following apical infection, but accumulated in the cytoplasm rather than entering the nucleus (Duan et al., 2000; Ding et al. 2005). One obstacle to the intracellular trafficking required for productive viral transduction is the ubiquitin-proteasome pathway (Duan et al., 2000; Yan et al., 2002); transient inhibition of proteasome activity dramatically enhances transduction (700-fold) of rAAV2-luciferase vectors from the apical surface by facilitating translocation of the vector to the nucleus (Yan et al., 2006). However, the application of proteasome inhibitors to enhance transduction efficiency of rAAV-CFTR vectors only marginally improves CFTR expression, most likely due to the low activity of the short promoter used in the rAAV-CFTR vectors (Zhang et al., 2004). The open reading frame (ORF) of the CFTR gene is 4.443 kb, and thus approaches the size of the 4.679 kb AAV genome. Although the AAV capsid can accommodate content in excess of its native DNA genome, its maximum packaging capacity is approximately 5.0 kb (Dong et al., 1996), and transgene expression from vectors exceeding this limit result in significantly reduced function (Wu et al., 1993). Given the requirements for 300 by of cis-elements from the AAV genome (two ITR sequences at the termini) and the 4,443 by CFTR coding sequence, there is little space left in the vector genome (257 bp) for a strong promoter and polyadenylation signal, Thus, the first-generation rAAV-CFTR vector (AV2.tgCF) that was tested in clinical trials, relied on the cryptic promoter activity of the AAV2 ITR to drive transcription of the full-length CFTR cDNA with a synthetic polyadenylation signal (Flotte et al., 1993; Aitken et al., 2003).

More recently, a rAAV vector, AV2.tg83-CFTR was developed, which uses an 83-bp synthetic promoter (tg83) (Zhang et al., 2004) to improve expression of the full-length human CFTR cDNA. The genome of this vector is 4.95 kb in size. Although this vector produced a 3-fold increase in cAMP-mediated Cl$^-$ currents in CF HAE ALI cultures relative to AV2.tgCF, this level of expression remained suboptimal for application in CF gene therapy. Other groups have attempted to use a CFTR minigene to create space for incorporating a better promoter into the rAAV vectors; this seemed justified based on earlier studies of CFTR gene function and structure indicating that the deletion of short, nonessential sequences from the C-terminus and regulatory domain (R-domain) had only minimal effects on the chloride channel function of CFTR (Zhang et al., 1998). One widely used CFTR minigene is CFTRΔR, which lacks 156 bp encoding 52 amino acid residues (708-759) at the N-terminus of the R-domain. Gene transfer with a recombinant adenoviral vector encoding CFTRΔR in CF HAE ALI cultures demonstrated that this transgene retains at least 80% of the transepithelial Cl⁻ transport supported by full-length CFTR (Ostedgaard et al., 2002). In addition, the expression of CFTRΔR in CFTR⁻/⁻ knockout mice rescued the lethal intestinal phenotype (Ostedgaard et al., 2011). This 156 bp deletion made it possible to package a rAAV CFTR expression vector 4.94 kb in length, with expression driven by a minimal CMV promoter (173 bp), into an AAV5 capsid (Ostedgaard et al., 2005). Additional efforts were aimed at developing AAV variant vectors of higher apical tropism, through directed evolution of the AAV capsid in polarized HAE ALI cultures (Li et al., 2009). However, these rAAV vectors did not provide efficient CFTR expression because the minimal CMV promoter did not function well in fully differentiated airway epithelia.

SUMMARY

To circumvent the size limitation of the promoter in a recombinant adeno-associated viral (rAAV) vector that can be used to express certain transgenes, a set of 100-mer synthetic enhancer elements, composed of ten 10 bp repeats, were screened for the ability to augment CFTR transgene expression from a short 83 bp synthetic promoter in the context of a rAAV vector for application in cystic fibrosis (CF) gene therapy. Screening for the effectiveness of synthetic enhancers to augment transgene expression was conducted in a stepwise fashion-in plasmids without AAV sequences, proviral vectors in the form of plasmids with AAV sequences, and rAAV vectors. Both plasmid transfection and viral vector transduction in cultured cell lines and whole animals in vivo were evaluated. Initial studies assessing transcriptional activity in monolayer (non-polarized) cultures of human airway cell lines and primary ferret airway cells revealed that three of these synthetic enhancers (F1, F5, and F10) significantly promoted transcription of a luciferase transgene in the context of plasmid transfection. Further analysis in polarized cultures of human and ferret airway epithelia at an air-liquid interface (ALI), as well as in the ferret airway in vivo, demonstrated that the F5 enhancer produced the highest level of transgene expression in the context of an AAV vector. Furthermore, it was demonstrated that increasing the size of the viral genome from 4.94 to 5.04 kb did not significantly affect particle yield of the vectors, but dramatically reduced the functionality of rAAV-CFTR vectors because of small terminal deletions that extended into the CFTR expression cassette of the 5.04 kb oversized genome. Since rAAV-CFTR vectors greater than 5 kb in size are dramatically impaired with respect to vector efficacy, a shortened ferret CFTR minigene with a 159 bp deletion in the R-domain was utilizing to construct a rAAV vector (AV2/2.F5tg834CFTRΔR). This vector yielded an about 17-fold increase in expression of CFTR and significantly improved Cl⁻ currents in CF ALI cultures. This small enhancer/promoter combination may have broad utility for rAAV-mediated gene therapy, e.g., CF gene therapy, to the airway.

The disclosure provides a recombinant vector such as a parvovirus vector, e.g., a recombinant adeno-associated virus (rAAV) vector or a bocavirus (BoV), such as a human BoV, vector, comprising a synthetic enhancer having a plurality of synthetic enhancer sequences operably linked to a promoter, e.g., a synthetic promoter. In one embodiment, each of the plurality of enhancers has the same sequence. In one embodiment, at least 2 of the plurality of enhancers have a different sequence. In one embodiment, the synthetic enhancer is formed of different enhancer sequences, where each unique sequence may be represented once or more than once, and if more than once, may be in tandem or interspersed with other (different) enhancer sequences. For example, the synthetic enhancer may have five different enhancer sequences, each represented twice in the synthetic enhancer, and the repeated sequences may be in tandem (or not). In one embodiment, at least one of the enhancer sequences has a TP53 binding site. In one embodiment, at least one of the enhancer sequences has a CREB binding site. In one embodiment, at least one of the enhancer sequences has a NRF-1 binding site (CATGCGCAG). In one embodiment, plurality has a combination of one or more TP53 binding sites, one or more NRF-1 binding sites, and/or one or more CREB, e.g., CREB7, binding sites. In one embodiment, the enhancer sequence has a binding site shown in one of FIGS. 8A-8C. In one embodiment, the plurality has 2 up to 20 distinct synthetic enhancer sequences In one embodiment, at least one of the enhancer sequences has no more than 15 bp. In one embodiment, the plurality is up to about 150 nucleotides in length, e.g., from about 20, 30, 40, 50, 60, 70, 80, 90, 100, 110, 120, 130, or 140 nucleotides in length. In one embodiment, the synthetic enhancer comprises F1, F5 or F10. In one embodiment, the enhancer has at least 80%, 85%, 90%, 92%, 95%, 98% or 99% nucleotide sequence identity to F1, F5 or F10. In one embodiment, the linked promoter is a synthetic promoter. In one embodiment, the promoter is tg83. In one embodiment, the promoter is an AAV promoter. In one embodiment, the promoter is a heterologous promoter, e.g., from a different virus or from a mammalian genome. In one embodiment, the promoter is operably linked to an open reading frame, e.g., a heterologous open reading frame. In one embodiment, the open reading frame encodes a prophylactic or a therapeutic gene product, e.g., cystic fibrosis transmembrane conductance regulator, α-antitrypsin, β-globin, γ-globin, tyrosine hydroxylase, glucocerebrosidase, aryl sulfatase A, factor VIII, dystrophin or erythropoietin. In one embodiment, the combination of the plurality of enhancer sequences and the promoter is no more than 300 nucleotides in length, e.g., no more than 125, 150, 175, 200, 250, or 275 nucleotides in length. In one embodiment, the combination of the plurality of enhancer sequences and the promoter is less than 500 nucleotides in length. In one embodiment, the vector is a parvovirus vector such as a rAAV vector, e.g., an AAV1, AAV2, AAV3, AAV4, AAV5, AAV6, AAV7, AAV8, or AAV9 vector, or a human bocavirus vector, e.g., HBoV1, HBoV2, HBoV3 or HBoV4, or an evolved AAV or HBoV vector that adapts a unique tropism, e.g., optionally one with slightly altered capsid sequences from known serotypes This disclosure also relates to an approach to screen tissue-specific as well as ubiquitous synthetic promoter/enhancer combinations in a step-wise fashion, in plasmids, proviral vectors, and rAAV vectors, which can be used in the application of rAAV gene therapy for the delivery of large transgene cassette. Examples of use include but are not limited to express 4.3 kb B-domain deleted Factor-VIII in muscle and/or liver for hemophilia A, or to deliver the 4.2 kb the gene-editing tool of *Streptococcus pyogenes* (SpCas9) and a chimeric sgRNA together in any desired tissue and organ in vivo.

Further provided are methods of using the recombinant parvovirus vector to infect cells, e.g., mammalian cells such as ferret, canine, feline, bovine, equine, caprine, or porcine cells, or primate cells, e.g., human cells, for example, administering a composition comprising the recombinant parvovirus vector to a mammal. For example, the recombinant parvovirus genome may include an expression cassette encoding a heterologous gene product, e.g., which is a therapeutic protein such as cystic fibrosis transmembrane conductance regulator, α-antitrypsin, β-globin, γ-globin, tyrosine hydroxylase, glucocerebrosidase, aryl sulfatase A, factor VIII, dystrophin, erythropoietin, alpha 1-antitrypsin, surfactant protein SP-D, SP-A or SP-C, erythropoietin, or a cytokine, e.g., IFN-alpha, IFNγ, TNF, IL-1, IL-17, or IL-6, or a prophylactic protein that is an antigen such as viral, bacterial, tumor or fungal antigen, or a neutralizing antibody or a fragment thereof that targets an epitope of an antigen such as one from a human respiratory virus, e.g., influenza virus or RSV including but not limited to HBoV protein, influenza virus protein, RSV protein, or SARS protein.

FIGS. 2A-2F. Effectiveness of enhancers F1, F5 and F10 in augmenting activity of the tg83 promoter in the context of proviral plasmids and rAAV. A) Effect of the AAV2 ITR on transcription from the tg83 promoter, as evaluated following transfection of A549 and primary airway ferret cells with pGL3-tg83 or pAV2-tg83luc, Data represent the mean (+/−SEM, N=3) relative luciferase activity (RLU) 24 hours post-transfection. B) Effectiveness of enhancers on transcription following transfection of A549 and primary ferret airway cells with the indicated AAV2 proviral plasmids, Data represent the mean (+/−SEM, N=3) relative luciferase activity of each transfection, normalized to the enhancer-less vector pAV2-tg83luc (set to 1 for each cell type), at 24 hours post-transfection. C) Effectiveness of enhancers on transcription following infection of A549 cells with the indicated rAAV2 vectors at 24 hours post-infection. Data represent the mean (+/−SEM, N=3) relative luciferase activity for each infection, normalized to the enhancer-less vector pAV2-tg83luc (set to 1). (D and E) Effectiveness of enhancers on transcription following basolateral infection of polarized (D) human and (E) ferret airway epithelia infected with $2\times10^{10}$ DRP of the indicated rAAV2 vectors. Data represent the mean (+/−SEM, N=4) relative luciferase activity (RLU) for each condition at 2 days post-infection. (F) Effectiveness of enhancers on transcription in lung and tracheal tissue following infection of 5 day-old ferret pups with $2\times10^{11}$ DRP of AV2/1.F5tg83luc or AV2/1.F10tg83luc, in the presence of proteasome inhibitors, Luciferase activity was measured 8 days post-infection, Data represent the mean (+/−SEM, N=4) relative luciferase activity (RLU/μg protein).

FIGS. 3A-3C. Impact of rAAV-CFTR construct size on restoration of CFTR chloride currents in polarized CF airway epithelium, A) Schematic illustration of structures of rAAV2 vectors of distinct sizes that encode the full-length ferret CFTR open reading frame (ORF) and R domain-deleted variants, under the control of the same transcriptional elements: the 83 by synthetic promoter (tg83), a 62 bp synthetic polyadenylation signal (pA), a 17 bp 5' untranslated region (UTR), and a 9 bp 3' UTR, The ORF of full-length ferret CFTR (fCFTR) is 4455 bp. The 99 bp 3×HA tag was inserted between amino acid residues 5900 and 1901, bringing fCFTR(HA) to 4554 bp. The fCFTRΔR has a shortened ORF (4,296 bp); 53 amino acid residues (I708-I760, 159 bp) are deleted from the R-domain. fCFTRΔR(HA) is 4395 bp in length, having a 99 bp HA-tag insertion and a 159 bp deletion in the R-domain. The functionalities of these vectors on rescue of CFTR specific $Cl^-$ transport (reflecting by transepithelial short-circuit currents (lsc)) were compared in differentiated CF HAE ALI cultures, following infection at $10^{11}$ DRP per Millicell insert (MOI of about $10^5$ DRP/cell) in the presence of the proteasome inhibitors LLnL (10 μM) and doxorubicin (2 μM). CF HAE ALI cultures were generated from a conditionally transformed human CF airway cell line (CuFi8; genotype ΔF508/ΔF508). B) Typical traces of the lsc changes from CF ALI cultures, infected indicated AAV-CFTR vectors, following the sequential addition of various inhibitors and agonists. Amiloride and DIDS were used to block ENaC-mediated sodium currents and non-CFTR chloride channels prior to addition of cAMP agonist (forskolin and IBMX), and GlyH101 was used to block CFTR-specific currents. Δlsc (IBMX & Forsk) reflects the activation of CFTR-mediated chloride currents following induction with cAMP agonist, and Δlsc (GlyH101) reflects the inhibition of CFTR-mediated chloride currents following addition of GlyH101. C) Effects of vector size on rescue of chloride lsc currents. rAAV-CFTR vectors were increased by about 100 bp increments. Shown are the Δlsc (IBMX & Forsk) and Δlsc (GlyH101) responses, indicating the magnitude of CFTR-mediated chloride transport following basolateral infection CF HAE ALI, as described in (B). CFTR currents generated from primary non-CF HAE (N=14) are provided for comparison. Data represent the mean (+/−SEM) for N=3 independent Millicell inserts.

FIGS. 4A-4B. Analyses of integrity of the viral genome by denaturing gel electrophoresis and slot blot analysis. A) Viral DNA was extracted from $10^9$ DRP of the indicated AAV-CFTR vectors, resolved on a 0.9% alkaline agarose gel, and transferred to a Nylon membrane. Southern blotting was performed with a $^{32}P$-labeled CFTR probe to visualize the viral DNA. B) To assess potential deletion that may have occurred at the termini of positive and minus strand viral genomes, $3.33\times10^8$ DRP of each virus (titer determined by TaqMan PCR with probe/primer set against fCFTR cDNA) were loaded in triplicate onto a Slot-Dot® SF Module (Bio-Rad, Hercules, Calif.) fitted with a Nylon membrane. 3-fold serial dilution of proviral plasmid ($3\times10^9$ to $3.7\times10^7$ copies) was also loaded for generating the standard curves for quantitation. The blots were probed with $^{32}P$-labeled oligonucleotides against the tg83 promoter, CFTR cDNA, or polyA. (−) and (+) represent the probes hybridizing to the minus and positive strand of the single stranded rAAV genome. Hybridization was first conducted with the set of probes that hybridize to the minus strand, and then reprobed with the set of oligonucleotides that hybridize to the positive strand. The number of viral genome copies detected by each probe was determined (mean+/−S.E.M, N=3) based on measurement of the signal density using NIH ImageJ and comparison to standard curves.

FIG. 5. Effects of the F5 enhancer on CFTR currents generated by CF HAE following infection with rAAV vectors. CF HAE ALI were infected with AV2/2.tg83-fCFTRΔR or AV2/2.F5tg83-fCFTRΔR, at the indicated MOIs, from the apical or basolateral surface. Proteasome inhibitors were co-administrated during the 16 hours infection period. lsc measurements of the infected ALI cultures were conducted at 2 weeks post-infection. The mean (+/−SEM) Δlsc (IBMX & Forsk) and Δlsc (GlyH101) are shown with the N for independent transwells assays indicated. Mock-infected CF and non-CF HAE cultures are shown for reference.

FIGS. 6A-6B. Effects of the F5 enhancer on CFTR currents and tg83-directed CFTR transcription following infection with rAAV vectors. CF HAE ALI were infected with AV2/2.tg83-fCFTRΔR or AV2/2.F5tg83-fCFTRΔR at an MOI of 2×10⁴ DRP/cell from the basolateral surface, in the presence of proteasome inhibitors. A) lsc was measured in the infected ALI cultures at 3 and 10 days post-infection. Δlsc (IBMX & Forsk) and Δlsc (GlyH101) values are presented. B) The abundance of vector-derived CFTR mRNAs in cultures evaluated in Panel a, as determined using RS-PCR and normalized to GAPDH transcripts in each sample. Data represent the mean (+/−SEM) for N=3 independent transwells in each panel.

Figure 7A:
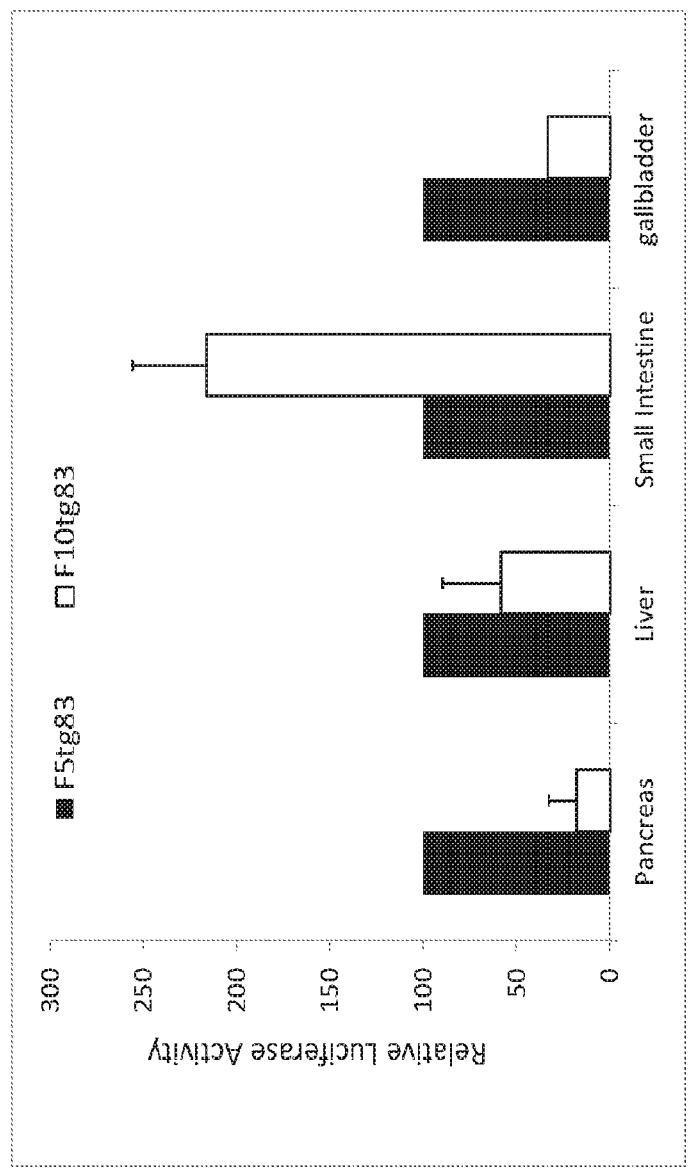
Figure 7B:
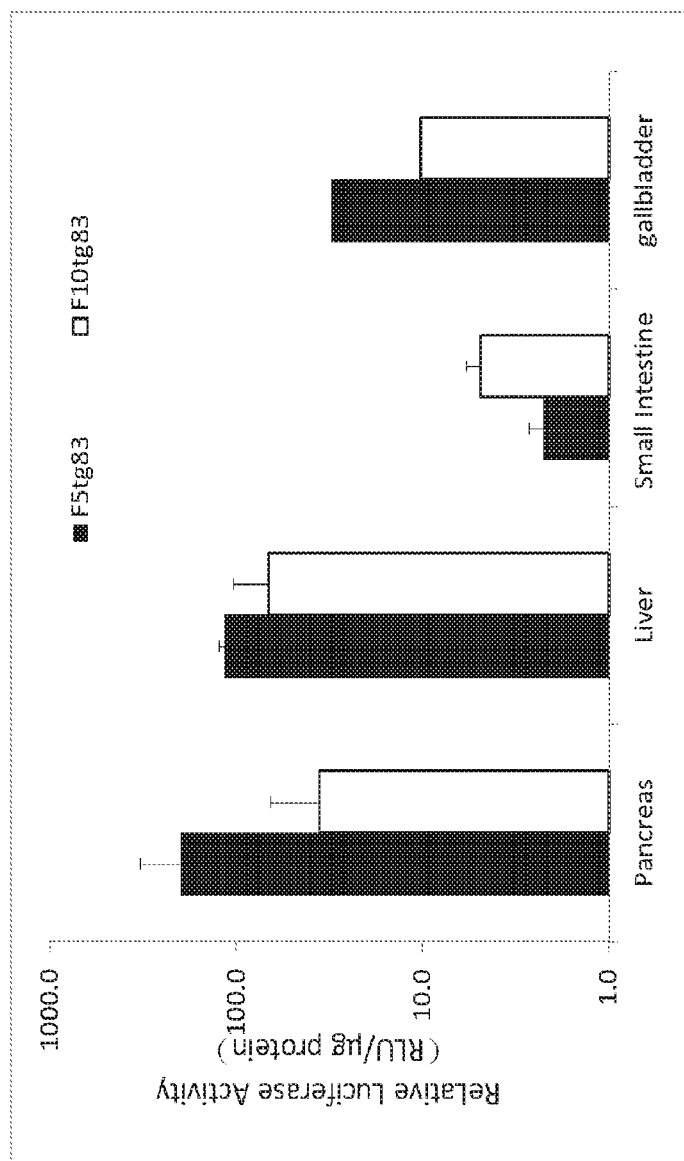
Figure 9B:
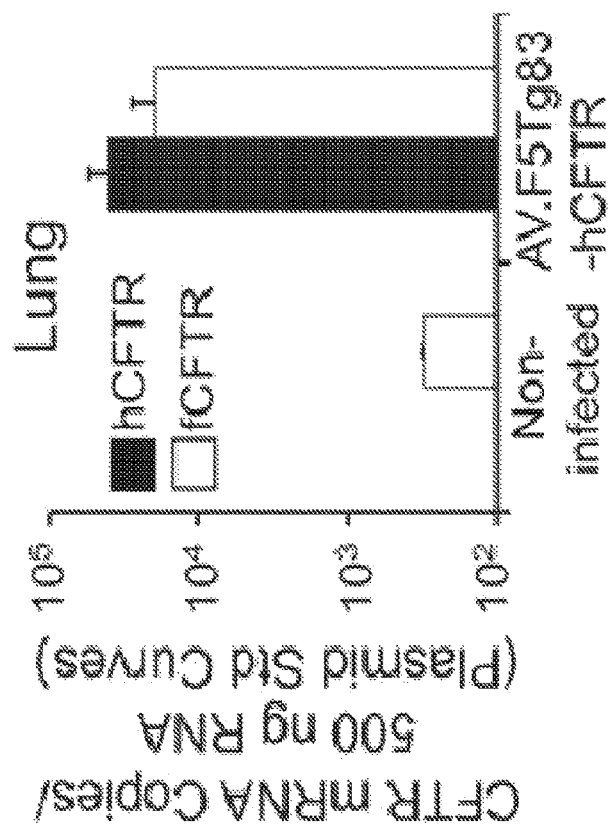
Figure 9A:
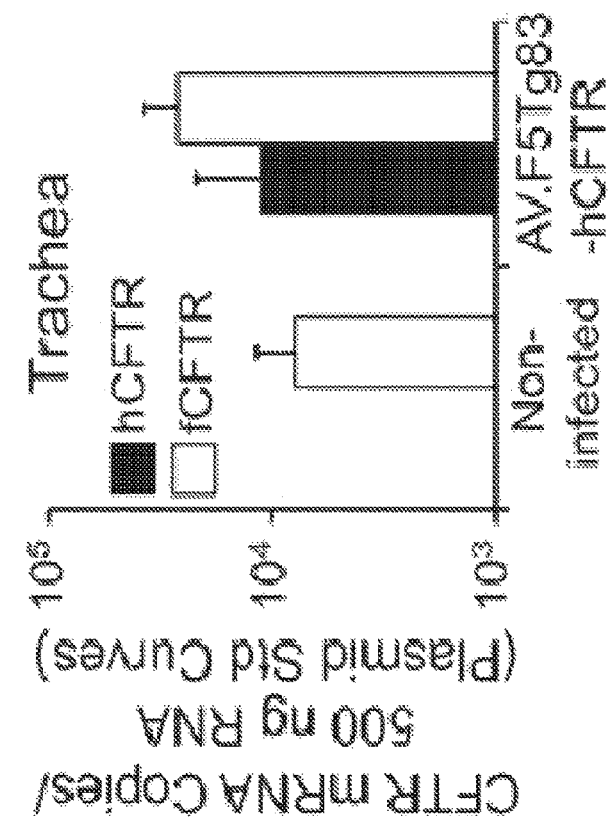
Figure 9D:
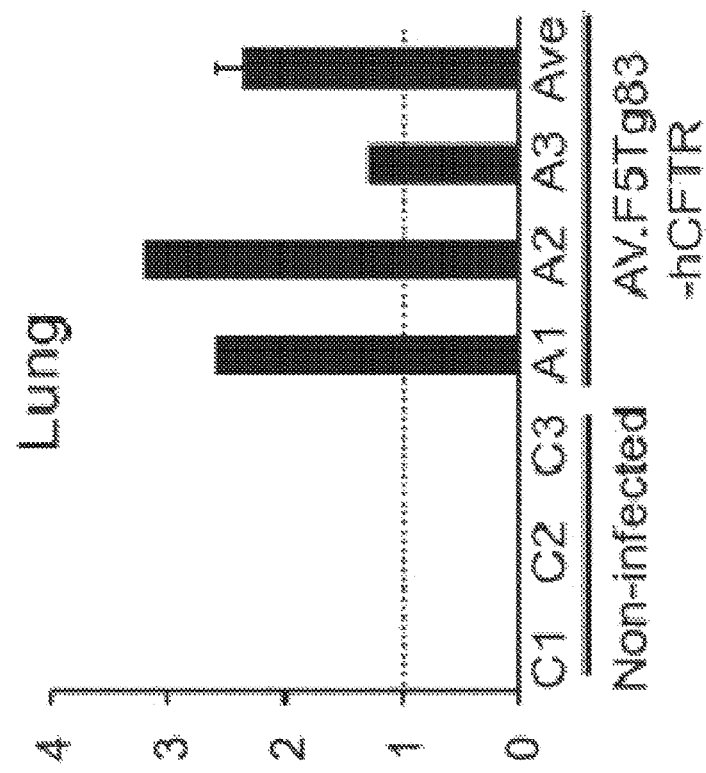
Figure 9C:
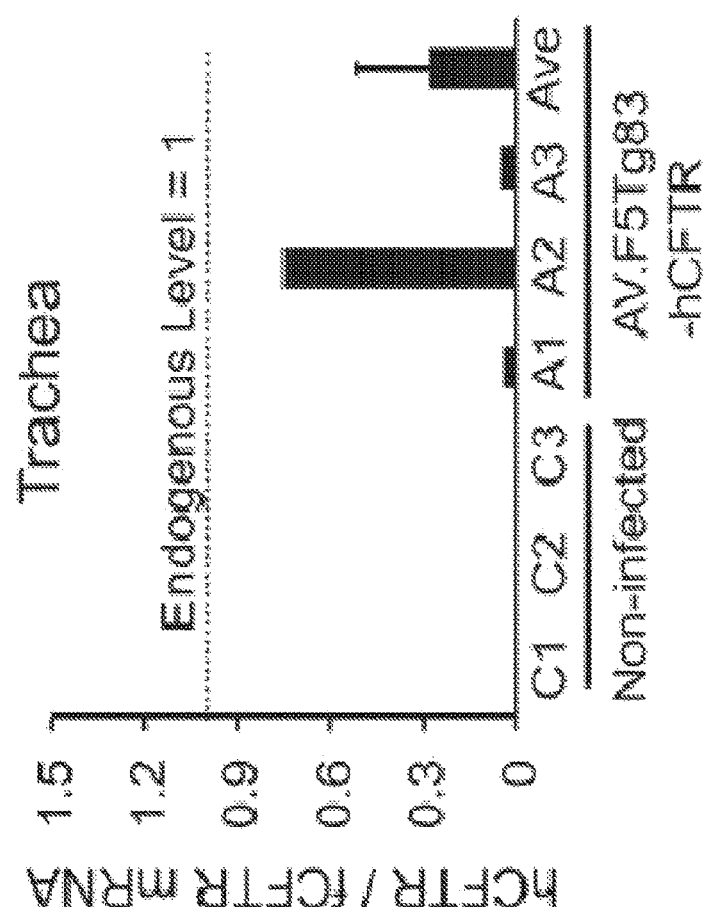
Figures 10A, 10B:
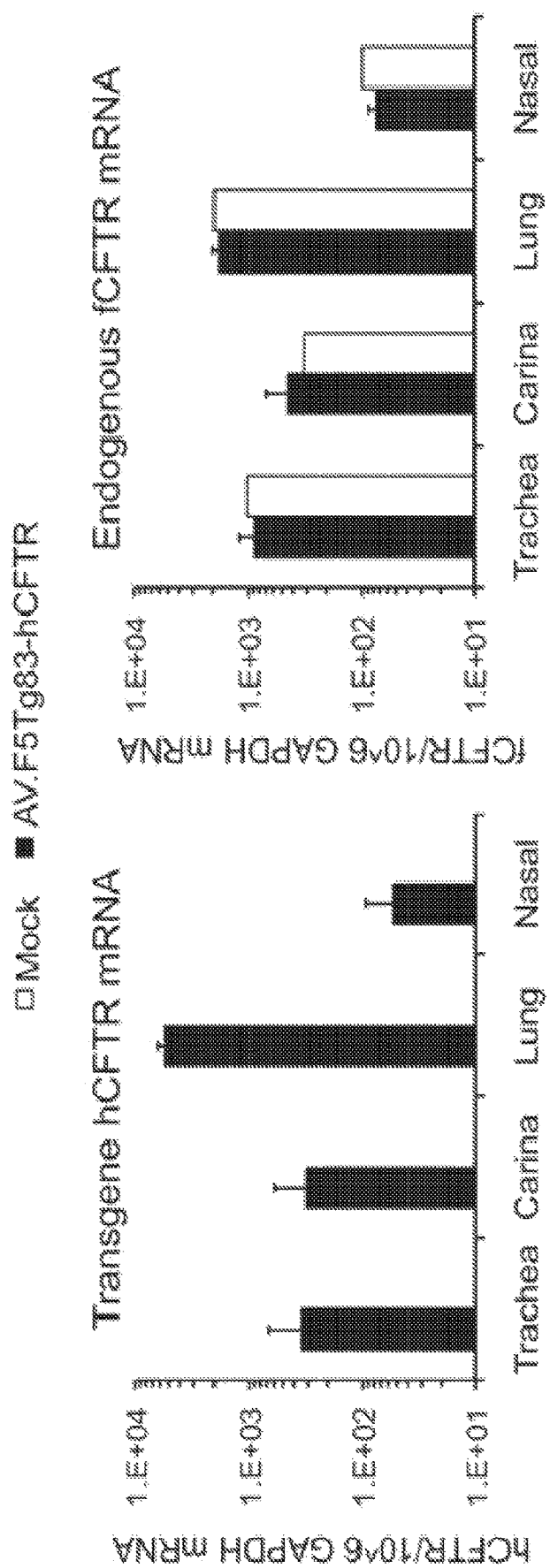
Figures 10C, 10D:
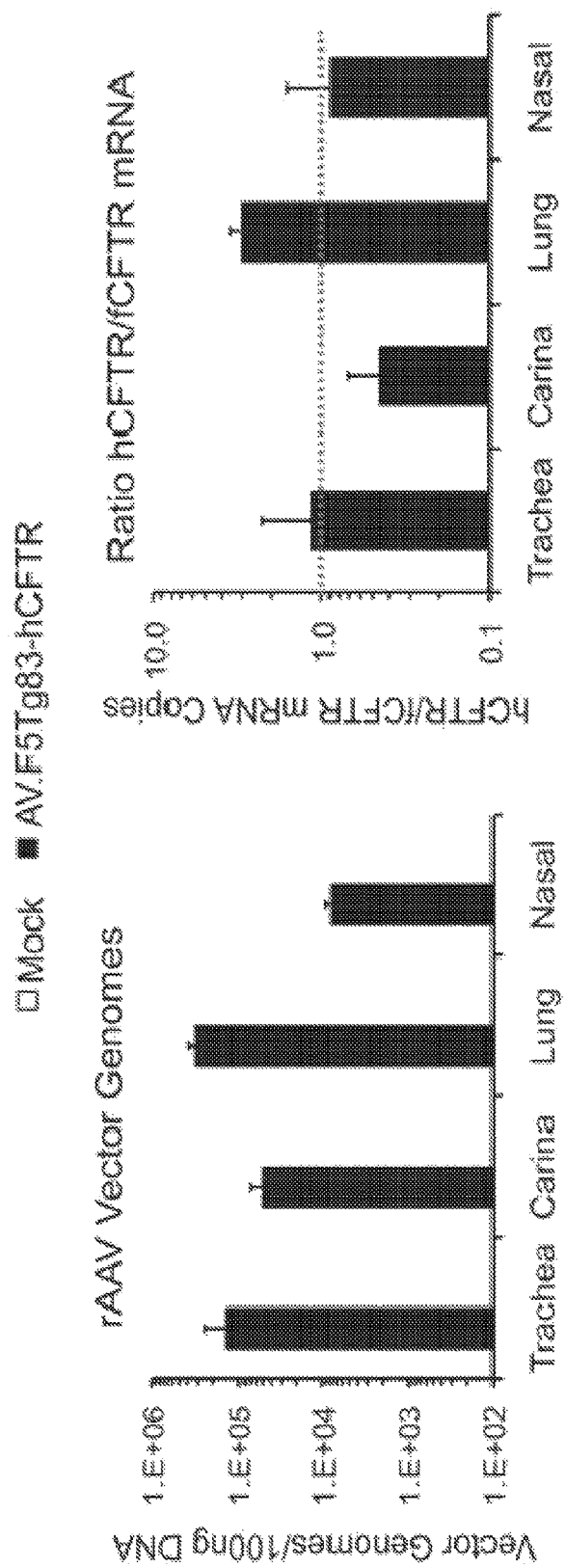

FIGS. 7A-7B. 5 day old ferrets were systemically infected with 2×10¹¹ DRP AAV2/9F5tg83luc or AAV2/9F10tg83luc via jugular vein injection. Animals were euthanized 8 day post-infection, snap tissues from different organs were harvested and homogenized in reporter lysis buffer (Promega) for luciferase assays. A) Data compare the luciferase expression from the infections of AAV2/9F5tg83luc or AAV2/9F10tg83luc when the luciferase expression from F5tg83 promoter was arbitrarily set as 100 in each tissue. B) Values represent the (mean +SEM, n=3) relative luciferase activity (RLU/μg protein).

FIGS. 8A-8W, A-E) Binding sites in F5 which may be employed to prepare synthetic enhancers as described herein. F-P) Binding sites in F10 which may be employed to prepare synthetic enhancers as described herein. Q-W) Binding sites in F5tg83, which may be employed to prepare synthetic enhancers or promoter as described herein. SEQ NOs: 31-60 and 63-68.

FIGS. 9A-D. Gene transfer efficiency of AV.F5Tg83-hCFTRΔR to the ferret trachea and lung. Three day old ferrets were infected with a 100 μL volume of 6×10¹¹ DRP of AV.F5Tg83-hCFTRΔR in 500 μM doxorubicin. Non-infected animals were given an equal volume of vehicle with doxorubicin. At 10 days post-infections the entire lung and trachea were harvested and snap frozen in liquid nitrogen. Tissue was pulverized and mRNA and cDNA generated for Q-PCR of human and ferret CFTR. (A and B) Copies of hCFTR and fCFTR mRNA in the (A) trachea and (B) lung. Copy number was determined using a standard curve generated from serial dilutions of plasmid CFTR cDNA for each species. (C and D) Ratio of transgene-derived hCFTR to endogenous fCFTR mRNA. C1-C3 represent animals in the mock-infected group and A1-A3 represent animals in the AAV-infected group. The average is also shown for the three AAV-infected animals. The dashed line represents endogenous levels of CFTR (ratio=1). Data depicts the mean +/−SEM for N=3 animals in each group.

FIGS. 10A-D. AV.F5Tg83-hCFTRΔR effectively transduces the mature ferret airways. The lungs of 1 month old ferrets (N=3) were transduced with 7.5×10¹² DRP of AV.F5Tg83-hCFTRΔR harboring the hCFTRΔR cDNA in a 500 μL volume of PBS in the presence of 250 μM doxorubicin. A mock-infected control animal (N=1) received 500 μL PBS with no vector in the presence of 250 μM doxorubicin. Vector was delivered to the lung with a PennCentury microsprayer through tracheal intubation. Nasal delivery in the same animals was also performed using 100 μL containing 1.5×10¹² DRP with 250 μM doxorubicin by instillation of fluid. Mock-infected nasal delivery received PBS with 250 μM doxorubicin. At 12 days following infection, the lung lobes were harvested separately along with the trachea, carina, and nasal turbinates with surrounding adventitia. The tissues were snap frozen and pulverized samples were processed separately for mRNA and DNA. A) TaqMan RNA-specific PCR (RS-PCR) for human CFTR mRNA and endogenous ferret GAPDH mRNA for vector and mock treated animals. Results show the ratio of hCFTR/fGAPDH mRNA. B) TaqMan RS-PCR for endogenous ferret CFTR mRNA and endogenous ferret GAPDH mRNA for vector and mock treated animals. Results show the ratio of fCFTR/fGAPDH mRNA. C) TaqMan Q-pCR for the number vector genomes in each sample per 100 ng DNA. D) The ratio of mRNA copies for hCFTR/fCFTR for each sample. 1 is equal to endogenous levels of CFTR (red dashed line). Lung samples contained on average 3.0+/−0.5 copies of transgene derived hCFTR mRNA per copy of fCFTR mRNA. Trachea and nasal tissue transduction was more variable, but averaged one copy of transgene derived hCFTR/fCFTR mRNA. Results depict the mean +/−SEM for the vector treated animals.

DETAILED DESCRIPTION

Gene therapy has been widely used in clinical trials since 1990s with many successful cases reported using viral or non-viral vectors to deliver therapeutic genes, rAAV is the most widely used one proven of high safety profile, broad tissue/organ tropism and persistence transgene expression. AAV is a small single stranded DNA virus of an inherently small 4.679 kb genome, thus the application of rAAV for gene therapy is restricted to delivering relative small transgenes. Although AAV capsid can house a rAAV genome slightly larger than its original size, 4.95 kb appears to be the maximal size for efficient transgene expression. Since a 300-bp sequence of an AAV essential cis element (terminal repeats at both termini) is included in a rAAV vector, the actual insertion of an exogenous gene expression cassette cannot exceed 4.6 kb. This is a challenge for delivering effective expression of a large gene whose size approaches to this limit.

One typical example is to deliver the CFTR gene (cystic fibrosis transmembrane conductance regulator) for cystic fibrosis (CF) gene therapy using rAAV vector. The coding sequence for CFTR gene is as large as 4.443 kb. To construct a CFTR expressing AAV vector, with the necessity of minimal 5' and 3' UTR and the cloning sites, there is a room of less than 200 bp to incorporate promoter and polyadenylation signal to direct the transcription of full-length CFTR cDNA.

Recently, a CFTR knockout ferret model was established that spontaneously develops a lung phenotype that mirrors key features of human CF disease, including spontaneous bacterial infection of the lung, defective secretion from submucosal glands, diabetes, and gastrointestinal disease (Sun et al., 2008; Sun et al., 2010; Oliver et al., 2012; Sun et al., 2014; Yan et al., 2013. It has been demonstrated that the airways of newborn ferrets can be efficiently transduced by rAAV1 in the presence of proteasome inhibitors (Yan et al., 2013). Thus, preclinical studies in the CF ferret model can be initiated as soon as a rAAV vector that effectively expresses CFTR in airway epithelium is generated, rAAV inherently small 4.679 kb genome necessitates the use of a short but robust transcription regulatory element to effectively express a large transgene whose size approaches to the package limit. cassette was generated that efficiently expresses the ferret CFTR (fCFTR) gene.

The first-generation rAAV-CFTR vector (AV2.tgCF), relied on the cryptic promoter activity of the AAV2 ITR, inefficiently expressed CFTR in clinical trials. To overcome this problem, another rAAV vector, AV2.tg83-CFTR, which uses an 83-bp synthetic promoter (tg83) was used to improve expression. Although this vector produced a 3-fold higher in cAMP-mediated Cl– currents in CF HAE ALI cultures than AV2.tgCF, this level of expression remains suboptimal for application in CF gene therapy. So, there is an immediate need for a strong short promoter to direct the CFTR expression in the AAV vector for CF gene therapy. Similarly, to express the 4.3 kb B-domain deleted Factor-VIII in muscle and/or liver for hemophilia gene therapy using rAAV, short promoter effective in muscle and liver is also needed.

Another example is to deliver the CRISPR/Cas9 system for gene editing. The recent development of CRISPR/Cas9 gene editing technique promotes a new human gene therapy strategy by correcting a defect gene at pre-chosen sites without altering the endogenous regulation of gene of interest. This system consists of two key components: Cas9 protein and sgRNA, as well as a correction template when needed, rAAV can be used to deliver these elements in vivo to various target organs, but the co-delivery of Cas9 protein and the a chimeric sgRNA in the same cell is required while the dual-AAV vector delivery system is low efficient. Because the size of the expression cassette for *Streptococcus pyogenes* (SpCas9) and the transcription cassette sgRNA together exceeds 4.2 kb, to use a single rAAV vector to deliver the efficient expression SpCas9 protein, it necessitates the use of small but robust promoter/enhance sequence to direct the SpCas9 expression, thus, ubiquitous and/or tissue-specific enhancers are desired. Although *Staphylococcus aureus* Cas9 (SaCas9), which is about 1.0 kb smaller in size, fits together with its sgRNA and relevant expression cassettes within a single AAV vector, using short synthetic promoter allows for the additional incorporation of the gene correction template for an all-in-one rAAV vector in the application of gene editing-based gene therapy.

As described below, short (less than 0.2 kb) synthetic enhancer/promoters provide a solution to solve the current problem of rAAV vector in delivering a large transgene cassette. This disclosure, in one embodiment, relates to the use of a 183-bp F5tg83 synthetic enhancer/promoter to rAAV vectors to deliver effective CFTR expression in lung airway tissue for CF gene therapy. This disclosure, in one embodiment, also provides an effective approach to screen and identify tissue-specific or ubiquitous synthetic promoter/enhancer combinations.

Since enhancer activity differs by cell lines and state of cell differentiation, as well as is influenced by the AAV ITRs and by the sequence of gene of interest, the screening was conducted in a step-wise fashion, e.g., in plasmids, proviral vectors, and rAAV vectors.

In one embodiment, the screening system includes a defined 83-mer synthetic core promoter (tg83p) and a set of random 100-mer synthetic sequence of potent enhancer activity. The screening approach can be used to screen the 100-mer synthetic sequences for their enhancer activity to enhance promoter transcription, e.g., the 83 bp tg83promoter transcription, in different in organ/tissue for different gene of interests, in a similar in a step-wise fashion: such as to direct the Factor VIII expression in muscle or liver, as well as to direct the Cas9 protein expression in any specific tissues or stem cells. Besides tissue-specific expression, the approach also can be used to identify an enhancer of ubiquitous effect to improve the tg83p promoter activity in a wide range of tissue/organ, through testing rAAV derived reporter gene expressions at a multi-organ level.

Specifically, a set of vectors containing the synthetic tg83 promoter linked with different synthetic sequences (about 100 bp) of potent enhancer activity, was constructed for initial screening in monolayer (non-polarized) cultures of human airway cell lines and primary ferret airway cells, which as discussed below revealed that three of these synthetic enhancers (F1, F5, and F10) significantly promoted transcription of a luciferase transgene from tg83p in the context of plasmid transfection. The next was to construct rAAV reporter vectors with pre-chosen candidates (F1-, F5-, or F5-tg83p enhancer/prompter combination). These vectors also incorporated a partial sequence of the gene of interest (CFTR here) that can maximally fit into the rAAV genome; this approach allows for the screening of cDNA sequences that will ultimately reside in the recombinant virus and also influences enhancer/promoter activity through unknown processes (likely secondary structure of the DNA). Analysis in polarized cultures of human and ferret airway epithelia at an air-liquid interface (ALI) in the context of AAV vector infection found that the combination of F5tg83 (183 bp in length) was the most efficient promoter in both ALI cultures, leading to 19.6-fold and 57.5-fold increases in reporter (firefly luciferase) expression, respectively, over the enhancer-less counterpart. The F5tg83 promoter also produced the highest level of transgene expression in the ferret airway in vivo. Finally, the F5tg83 promoter was used the rAAV-CFTR vector to direct the CFTR expression, the vector (AV.F5tg83CFTRΔR) yielded an about 17-fold increase related to the enhancer-less vector (AV.tg83CFTRR) in vector derived CFTR mRNA transcription and significantly improved Cl– currents in human CF ALI cultures.

Thus, expression from rAAV vectors having a large transgene was enhanced using small synthetic enhancer/promoter combinations having from a defined 83-mer synthetic core promoter and a set of random synthetic 100-mer synthetic enhancers. In particular, several short 183 bp synthetic promoter/enhancer combinations (F5tg83, F1tg83 and F10tg83) were capable to direct strong transgene expression in human as well as non-human mammalian (such as ferret) airway cells. In one embodiment, the robust F5tg83 promoter can be used in rAAV vector to deliver the 4.4 kb cystic fibrosis transmembrane conductance regulator (CFTR) for cystic fibrosis gene therapy.

The invention will be further described by the following non-limiting examples.

EXAMPLE 1

Materials and Methods

Production of rAAV Vectors. All rAAV vector stocks were generated in HEK293 cells by triple plasmid co-transfection using an adenovirus-free system, and purified with two rounds of CsCl ultracentrifugation as reported in Yan et al. (2004), For all viral vectors and proviral plasmids, rAAV2 genomes were used and packaged into AAV2 or AAV1 capsid to generate rAAV2/2 and rAAV2/1 viruses, respectively. TaqMan real-time FOR was used to quantify the physical titer (DNase resistant particles, DRP) of the purified viral stocks as described in Yan et al. (2006) and Ding et al. (2006). The PCR primer/probe set used to titer luciferase vectors was: 5'-TTTTTGAAGCGAAGGTTGTGG-3'

(forward primer) (SEQ ID NO:1), 5'-CACACACAGTTCGCCTCTTTG-3' (reverse primer) (SEQ ID NO:2) and 5'-FAM-ATCTGGATACCGG-GAAAACGCTGGGCGTTAAT-TAMRA-3' probe) (SEQ ID NO:3); the primer/probe set used for ferret CFTR vectors was 5'-GACGATGTTGAAAGCATACCAC-3' (forward primer) (SEQ ID NO:4), 5'-CACAACCAAAGAAATAGC-CACC-3' (reverse primer) (SEQ ID NO:5) and 5'-FAM-AGTGACAACATGGAACACATACCTCCG-TAMRA-3' (probe) (SEQ ID NO:6). All primers and probes were synthesized by IDT (Coralville, Iowa). The FOR reaction was performed and analyzed using a Bio-Rad My IQ™ Real-time FOR detection system and software.

Analysis of Integrity of Viral Genomes. Viral DNA was extracted from $10^9$ DRP of AAV-CFTR vectors and resolved in 0.9% alkaline denatured agarose gel at 20 volts overnight in 50 mM NaOH/1 mM EDTA buffer. Following transfer to a Nylon membrane, Southern blotting was performed with a $^{32}$P-labeled CFTR probe to visualize the viral DNA. For examination of 5' end genome deletions in the oversized rAAV vectors, $3.33\times10^8$ DRP of each virus (quantitated by TaqMan PCR with probe/primer set against fCFTR cDNA) was loaded into a slot blotting Nylon membrane. The blots were first hybridized to a set of three $^{32}$P-labeled oligonucleotide probes against the minus strand of the rAAV genome: at the 5' sequence of the tg83 promoter: taccctcgagaacggtgacgtg (SEQ ID NO:7); the center of ferret CFTR cDNA: ggagatgcgcctgtctcctggaatg (SEQ ID NO:8); and the 3' sequence of the synthetic polyA: gcatc-gatcagagtgtgttggttttttgtgtg (SEQ ID NO:9). After exposure to X-film, the membranes were stripped of probe and hybridized again to another set of three $^{32}$P-labeled oligonucleotide probes complimentary to the positive strand. NIH ImageJ software was used to quantify the signal intensity of hybridization to determine the corresponding number of genomes detected by each probe with serial dilutions of the proviral plasmid as standards.

Cell Culture and Conditions for Transfections and Infections. Human airway cell lines A549 and IB3, as well as HEK 293 cells, were cultured as monolayers in Dulbecco's modified Eagle medium (DMEM), supplemented with 10% fetal bovine serum and penicillin-streptomycin, and maintained in a 37° C. incubator at 5% $CO_2$. Primary ferret airway cells were isolated and cultured as non-polarized monolayer or at an ALI to generate polarized epithelia as described in Liu et al. (2007). Polarized primary HAE were generated from lung transplant airway tissue as described in Karp et al. (2002) by the Cells and Tissue Core of The Center for Gene Therapy at the University of Iowa. Polarization of cells of the CuFi8 line, a conditionally transformed cell line that was generated from ΔF508/ΔF508 CF airway cells (Zabner et al., 2003), were polarized at an ALI using conditions similar to those used for primary HAE (Yan et al., 2013). Ferret and human airway epithelia were grown on 12 mm Millicell membrane inserts (Millipore) and differentiated with USG medium of 2% Ultroser G supplement (Pall BioSepra, SA, France) at an ALI prior to use. Cell lines and primary monolayer cultures of airway cells were transfected with plasmids using lipofectamine and 1.0 µg of plasmid. For rAAV infections of A549 cells, polarized human or ferret airway epithelial cells, vectors were typically left in the culture medium for 24 hours (A549 cells) or 16 hours (polarized cells). For apical infection of the polarized HAE ALI cultures, vectors were diluted in USG medium to a final volume of 50 µL and applied to the upper chamber of the Millicell insert. For basolateral infections, vectors were directly added to the culture medium in the bottom chamber. Proteasome inhibitors were supplied in the culture medium throughout the period of infection to polarized cells, at 40 µM LLnL (N-Acetyl-L-leucine-L-leucine-L-norleucine) and 5 µM doxorubicin in the case of polarized human, and 10 µM LLnL and 2 µM doxorubicin in the case of CuFI ALI cultures and ferret ALI cultures. Epithelia were exposed to the viruses and chemicals for 16 hours and then removed. At this time, the Millicell inserts were briefly washed with a small amount USG medium and fresh USG medium was added to the bottom chamber only. Doxorubicin was from Sigma (St, Louis, Mo.) and LLnL was from Boston Biochem (Cambridge, Mass.).

rAAV Infection of Ferret Lungs. All animal experimentation was performed according to protocols approved by the Institutional Animal Care and Use Committee of the University of Iowa. In vivo infection of ferret lungs was performed by intra-tracheal injection of a 300 µl inoculum containing $2\times10^{11}$ DRP of rAAV2/1 and 250 µM doxorubicin. Prior to infection at 5 days of age, ferret kits were anesthetized by inhalation of a mixture of isofluorane and oxygen. At 8-day post-infection, the animals were euthanized with an overdose sodium pentobarbital intraperitoneal injection. For luciferase expression assays, the ferret trachea and lung cassette was immediately frozen in liquid nitrogen and then pulverized using a cryogenic tissue pulverizer. 1 ml of Passive Lysis Buffer (Promega, Madison, Wis.) was added to the pulverized tissue to extract protein. After four freeze-thaw cycles, the tissue extract was centrifuged at 15,000 rpm for 5 minutes, and the clarified tissue extract was used for luciferase assays with a luciferase assay kit from Promega.

Measurement of Expression of the Firefly Luciferase Reporter. At the indicated times post-infection or transfection, cells were lysed with luciferase cell lysis buffer and luciferase enzyme activity in cell lysates was determined using the Luciferase Assay System (Promega) in a 20/20 luminometer equipped with an automatic injector (Turner Biosystems, Sunnyvale, Calif.).

Measurement of Short-Circuit Currents. Transepithelial short circuit currents (lsc) were measured using an epithelial voltage clamp (Model EC-825) and a self-contained Ussing chamber system (both purchased from Warner Instruments, Inc., Hamden, Conn.) as described in Liu et al. (2007). Throughout the experiment the chamber was kept at 37° C., and the chamber solution was aerated. The basolateral side of the chamber was filled with buffered Ringer's solution containing 135 mM NaCl, 1.2 mM $CaCl_2$, 1.2 mM $MgCl_2$, 2.4 mM $KH_2PO_4$, 0.2 mM $K_2HPO_4$, and 5 mM Hepes, pH 7.4. The apical side of the chamber was filled with a low-chloride Ringer's solution in which 135 mM Na-gluconate was substituted for NaCl. Transepithelial voltage was clamped at zero, with current pulses applied every 5 seconds and the short-circuit current recorded using a VCC MC8 multichannel voltage/current clamp (Physiologic Instruments) with Quick DataAcq software. The following chemicals were sequentially added to the apical chamber: (1) amiloride (100 µM), to inhibit epithelial sodium conductance by ENaC; (2) 4,4'-diisothiocyanato-stilbene-2,2'-disulfonic acid (DIDS) (100 µM), to inhibit non-CFTR chloride channels; (3) the cAMP agonists forskolin (10 µM) and 3-isobutyl-1-methylxanthine (IBMX) (100 µM) to activate CFTR chloride channels; and (4) the CFTR inhibitor GlyH-101 (N-(2-naphthalenyl)-[(3,5-dibromo-2,4-dihydroxyphenyl) methylene] glycine hydrazide) (10 µM) to block Cl⁻ secretion through CFTR. Δlsc was calculated by taking the difference of the plateau measurement average over 45 seconds before and after each change in conditions (chemical stimulus).

Quantitative Analysis of Vector-Derived CFTR mRNA Following Transduction with rAAV. The total RNA from rAAV-infected cells was prepared using the RNeasy Mini plus Kit (Qiagen). Since the residual ssDNA rAAV genome in the RNA sample can be an undesirable template for traditional Real Time PCR, a modified RNA-specific method for PCR of the rAAV vector[46] was used to detect the vector-derived ferret CFTR mRNA. In brief, the 1$^{st}$-strand cDNA synthesis was primed with an adapter (lower case)-linked, vector-specific primer that targets the synthetic polyadenylation signal sequence (upper cases). The sequence of this primer is 5'-gcacgagggcgacugucaUGAUCGAUG-CAUCUGAGCUCUUUAUUA-3' (SEQ ID NO:10), in which all dTs are replaced with dU. After RNase H digestion was carried out to eliminate the RNA templates, a ferret CFTR-specific primer (5'-TGCAGAT-GAGGTTGGACTCA-3'; SEQ ID NO:11) was used for synthesis of the 2$^{nd}$ strand. In order to avoid false amplification from cDNA produced from the single-stranded viral DNA, all of the dU components in the 1$^{st}$-and 2$^{nd}$-strand cDNA products, as well as the excess adapter primers, were degraded by applying uracyl-N-glycosylase (UNG). Thus, a 2$^{nd}$-strand cDNA product linked to the complementary sequence of the adapter derived exclusively from rAAV transcripts was produced. The primer set for TaqMan PCR contained the ferret CFTR sequence 5'-CAAGTCTCGCTCTCAAATTGC-3' (SEQ ID NO:12), and the adapter sequence 5'-GCACGAGGGCGACTGTCA-3' (SEQ ID NO:13). The TaqMan probe used was 5'-FAM-ACCTCTTCTTCCGTCTCCTCCTTCA-TAMRA-3' (SEQ ID NO:14).

Results

Synthetic Oliqonucleotide Enhancers that Increase tg83 Promoter-Driven Transcription in Airway Cells A previous unbiased screen evaluating short synthetic enhancers from a library containing 52,429 unique sequence identified enhancer elements capable of activating transcription from the 128 bp minimal cytomegalovirus (CMV) IE promoter (−53 to +75) in HeLa cells (Schlabach et al., 2010). This library comprised all possible 10-mer DNA sequences, printed on microarrays as 10 tandem repeats (for a total length of 100 bases each). The best-performing 100-mer oligonucleotides enhanced the transcription of this 128 bp CMV IE minimal promoter to 75%-137% of that induced by the 600 bp wild type CMV IE promoter (Schlabach et al., 2010). In previous studies, a 83 bp synthetic promoter sequence (tg83) was used to express the full-length CFTR gene from a rAAV vector (AV2.tg83-CFTR), and it was found to produce higher transgene expression in CF HAE cultures than the cryptic promoter of the AAV2 ITR (Zhang et al., 2009). The tg83 promoter consists of an ATF-1/CREB site and an Sp1-binding site from the promoter of the Na,K-ATPase α1 subunit, and the TATA box and transcription start site from the CMV IE promoter. It was hypothesized that combining the tg83 promoter with a synthetic enhancer identified through this library screen would produce transcriptional units of greater efficiency in polarized human and/or ferret airway epithelia in vitro and in vivo. To test this possibility, the top eight enhancer sequences identified by Schlabach et al. (F1, F4, F5, F10, C9, D3, CREB6 and CREB8; Schlabach et al., 2010) were evaluated for their ability to enhance tg83 transcription in human and ferret airway epithelium.

F1
(SEQ ID NO: 15)
AGTCAGGGCAAGTCAGTGGCAAGTCAGGGCAGTCAGGGCAGTCAGGGCAA
GTCAGGGCAAGTCAGGGCAAGTCAGGGCAAGTCAGGGCAAGTCAGGGCA

F10
(SEQ ID NO: 16)
gaattgacgcatatattgacgcatattgacgcaaattgacgcaaatgaca
gcaagattgacgcaaattgagcgcaaattgacgcaaattaattgacgcat F4
(SEQ ID NO: 17)
CTGATGCAATCTGATGCAATCTGATGCAATCTGATGCAATCTGATGCAAT
CTGAGCAATCTGATGCAATCTGATGCAATATGATGAATGTGATGCAAT F5
(SEQ ID NO: 18)
TGGTGAGCGTCTGGGCATGTCTGGGCATGTCTGGGCATGTCTGGGCATGT
CGGGCATTCTGGGCGTCTGGGCATGTCTGGGCATGTCTGGGCA C3
(SEQ ID NO: 19)
GCTGATGCAATCTGATGCAATCTGATGCAATCTGATGCAATCTGATGCAA
TCTGAGCAATCTGATGCAATCTGATGCAATATGATGAATGTGATGCAATT D9
(SEQ ID NO: 20)
GCTGATGCAATCTGATGCAATCTGATGCAATCTGATGCAATCTGATGCAA
TCTGAGCAATCTGATGCAATCTGATGCAATATGATGAATGTGATGCAATT CREB6
(SEQ ID NO: 21)
ATTGACGCGGATTGACGCGGATTGACGCGGATTGACGCGGATTGACGCGG
ATTGACGCGG CREB8
(SEQ ID NO: 22)
ATTGACGCGGATTGACGCGGATTGACGCGGATTGACGCGGATTGACGCGG
ATTGACGCGGATTGACGCGGATTGACGCG Enhancer/Promoter Combinations tg83
(SEQ ID NO: 23)
ctcgagaacggtgacgtgcacgcgtgggcggagccatcaggcaggttgct aataaggagagctcgtttagtgaaccgtcaga F1tg83
(SEQ ID NO: 24)
AGTCAGGGCAAGTCAGTGGCAAGTCAGGGCAGTCAGGGCAGTCAGGGCAA GTCAGGGCAAGTCAGGGCAAGTCAGGGCAAGTCAGGGCAAGTCAGGGCAc tcgagaacggtgacgtgcacgcgtgggcggagccatcacgcaggttgcta tataagcagagctcgtttagtgaaccgtcaga F10tg83
(SEQ ID NO: 25)
GAATTGACGCATATATTGACGCATATTGACGCAAATTGACGCAAATGACA GCAAGATTGACGCAAATTGAGCGCAAATTGACGCAAATTAATTGACctcg agaacggtgacgtgcaggcgtgggcggagccatcacgcaggttgctatat aagcagagctcgtttagtgaaccgtcaga F4tg83
(SEQ ID NO: 26)
CTGATGCAATCTGATGCAATCTGATGCAATCTGATGCAATCTGATGCAAT CTGAGCAATCTGATGCAATCTGATGCAATATGATGAATGTGATGCAATct cgagaacggtgacgtgcacgcgtgggcggagccatcaggcaggttgctat ataaggagagctcgtttagtgaaccgtcaga -continued F5tg83
(SEQ ID NO: 27)
GTGGTGAGCGTCTGGGCATGTCTGGGCATGTCTGGGCATGTCTGGGCATG TCGGGCATTCTGGGCGTCTGGGCATGTCTGGGCATGTCTGGGCATctcga gaacggtgacgtgcacgcgtgggcggagccatcacgcaggttgctatata agcagagctcgtttagtgaaccgtcaga C3tg83
(SEQ ID NO: 28)
GCTGATGCAATCTGATGCAATCTGATGCAATCTGATGCAATCTGATGCAA

TCTGAGCAATCTGATGCAATCTGATGCAATATGATGAATGTGATGCAATT ctcgagaacggtgacgtgcacgcgtgggcggagccatcacgcaggttgct atataaggagagctcgtttagtgaaccgtcaga D9tg83
(SEQ ID NO: 29)
GCTGATGCAATCTGATGCAATCTGATGCAATCTGATGCAATCTGATGCAA

Figure 1:
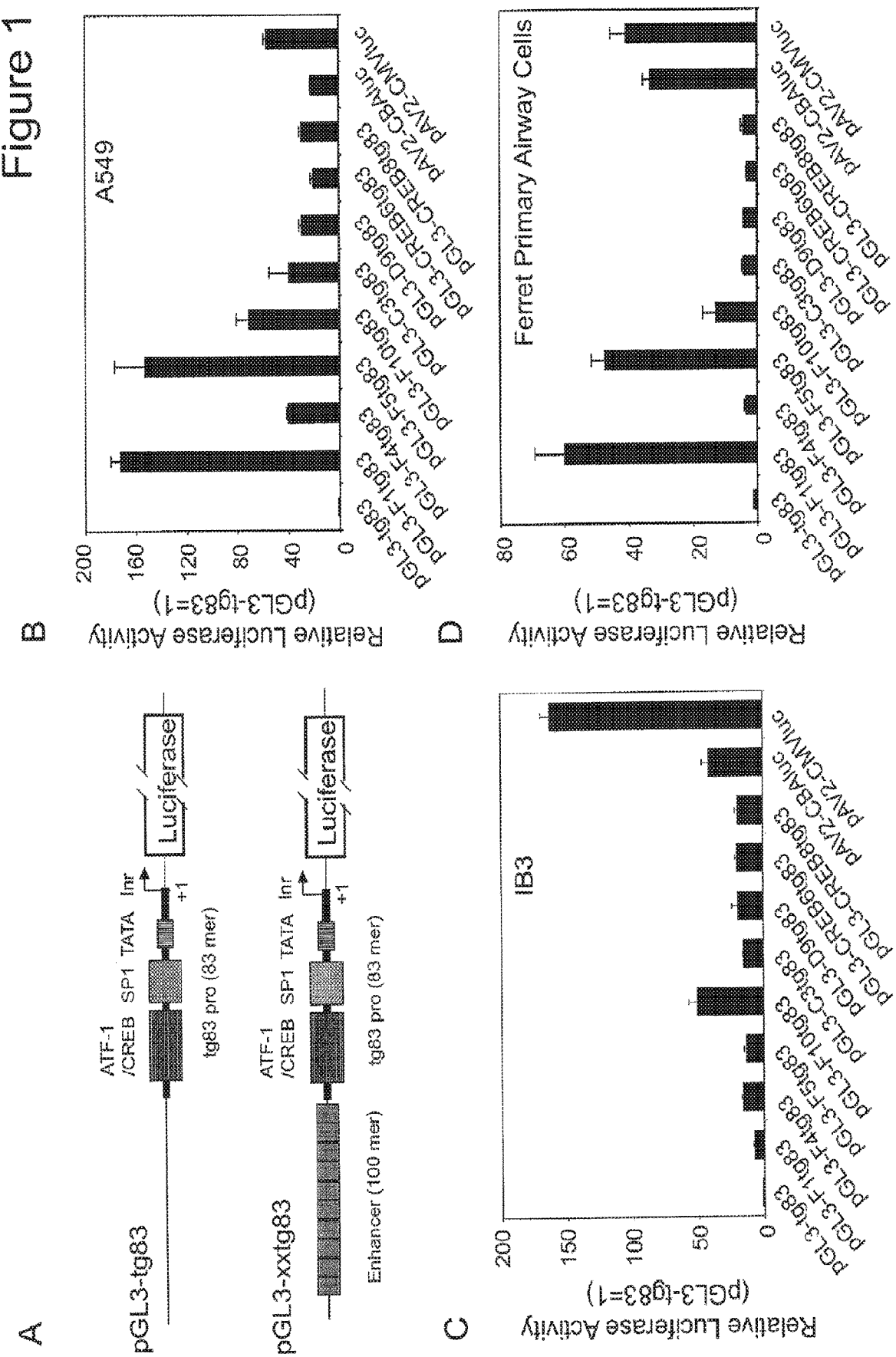
FIGS. 1A-1D. Effectiveness of synthetic oligonucleotide enhancers in augmenting activity of tg83-directed luciferase reporter plasmids in monolayer cultures. A) Schematic structure of the reporter vectors used to screen the enhancer library. The transcriptional motifs of the synthetic tg83 promoter are indicated. (B-D) Reporter activity in monolayer cultures of human airway cell lines (B) A549 and (C) IB3, and (D) ferret primary airway cells, following transfection with the indicated plasmids. Luciferase assays were conducted 24 hours post-transfection. Data represent the mean (+/−SEM, N=3) relative luciferase activity of each transfection normalized to that of the enhancerless vector pGL3-tg83luc, whose value in each cell-type tested was set to 1.

TCTGAGCAATCTGATGCAATCTGATGCAATATGATGAATGTGATGCAATT ctcgagaagggtgacgtgcaggcgtgggcggagccatcacgcaggttgct atataagcagagctcgtttagtgaaccgtcaga CREB6tg83
(SEQ ID NO: 30)
ATTGACGCGGATTGACGCGGATTGACGCGGATTGACGCGGATTGACGCGG ATTGACGCGGctcgagaacggtgacgtgcacgcgtgggcggagccatcac gcaggttgctatataagcagagctcgtttagtgaaccgtcaga The tg83 promoter was cloned into the promoter-less luciferase reporter plasmid pGL3-Basic Vector (Promega) to generate pGL3-tg83. Next a series of luciferase reporter expression plasmids were constructed, in which one of the eight 100-mer enhancers was placed in front of the tg83 promoter of pGL3-tg83 (FIG. 1A). Comparison of reporter expression from pGL3-tg83 and its enhancer-containing derivatives was conducted in monolayer (non-polarized) cultures of two human airway cell lines (A549 and IB3) and primary ferret airway cells (FIGS. 1B-1D). Two additional luciferase expression plasmids, pAV2-CMV-luc (contains the wild type, 600 bp CMV IE enhancer-promoter) and pAV2-CBA-luc (contains the CMV IE enhancer-chicken β-actin promoter, i.e., the CBA promoter) were included as controls for high-level promoter activity. Assessment of luciferase expression following plasmid transfection demonstrated that all of the enhancers tested increased tg83-driven luciferase expression, and that their efficiencies varied by cell line: in the human A459 cell and the primary ferret airway cell cultures, F1tg83 and F5tg83 exceeded the activity of the CBA and CMV promoters; and in the human IB3 cell cultures, F10tg83 was most effective but drove far less expression than the CMV promoter (FIGS. 1B-1D).

The F5 Element Most Efficiently Enhances tg83-Driven Transcription in Polarized Human and Ferret Airway Epithelia In Vitro as Well as in the Ferret Airway In Vivo Since the F1, F5 and F10 enhancers were the most effective in activating tg83-driven transcription in airway-cell monolayer cultures, the abilities of these elements to promote transcription in the context of rAAV vector genomes was evaluated. Four rAAV proviral vectors harboring a luciferase expression cassette were constructed, with expression driven by tg83 (enhancer-less), F1tg83, F5tg83 or F10tg83. The pAV2-tg83-fCFTR proviral plasmid was used as the template vector for cloning, its promoter and the 5' portion of the fCFTR coding region were replaced with the 2.1 or 2.2 kb luciferase expression cassette. The genome size was 4.75 kb in the case of rAV2.tg83luc, and 4.85 kb for the enhancer-containing vectors. This design was used for two reasons. First, retaining as much of the fCFTR sequence as possible ensured that the vector genome size would be similar to those of the rAAV-CFTR expression vectors that would ultimately be generated. Second, retaining regions of the fCFTR cDNA maximized the potential influences of the ferret CFTR sequence on enhancer function.

Figure 2:
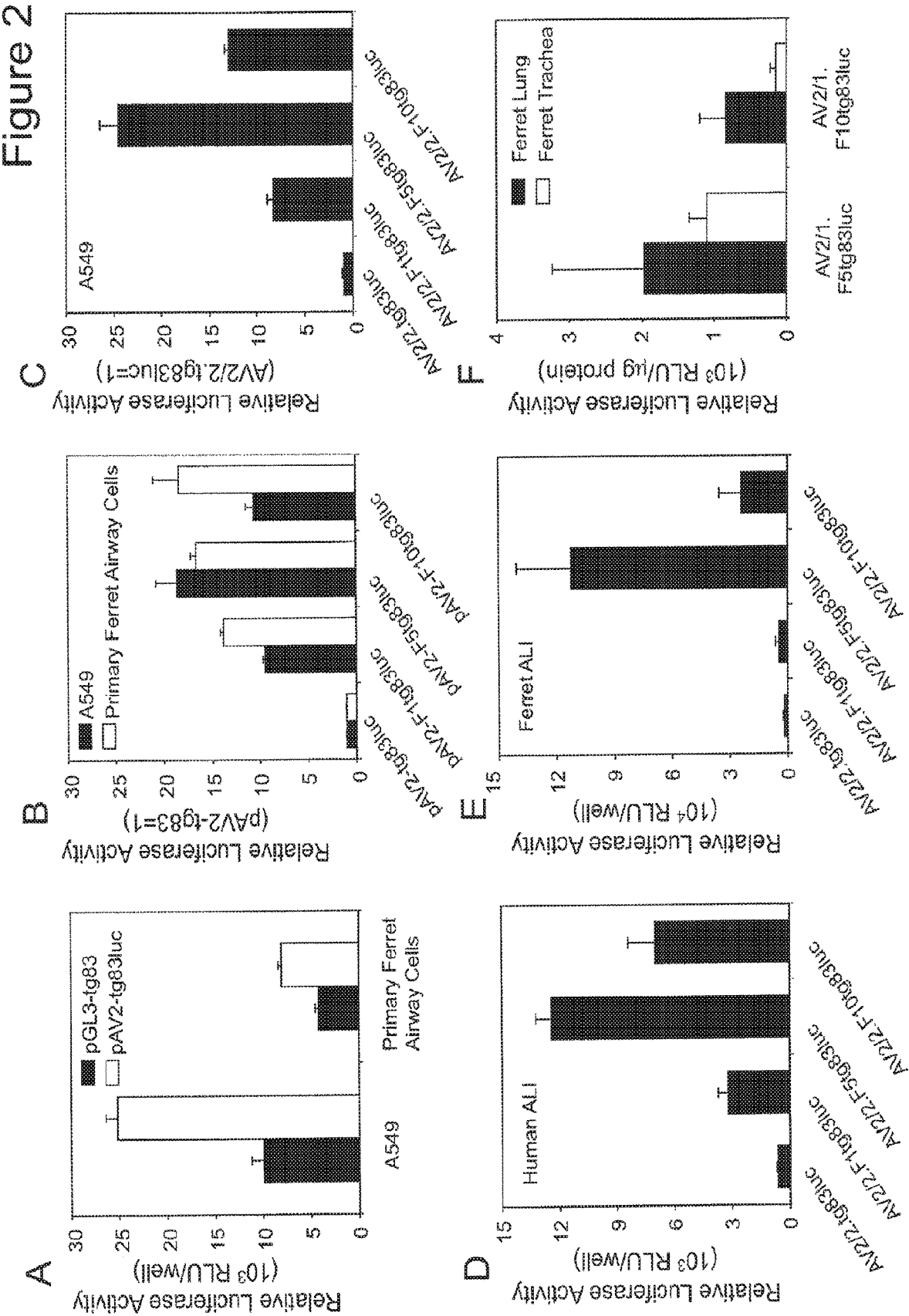

As a first step in investigating whether AAV ITRs and the portion of fCFTR transgene sequence to be tested (i.e., 3' half of the fCFTR cDNA) influence transcription from the tg83 promoter, reporter expression from pGL3-tg83 and pAV2-tg83luc plasmids was compared following transfection into monolayer cultures of A549 and primary ferret airway cells. pAV2-tg83luc plasmid was found to be 2.5-fold (in A549) and 2-fold (in primary ferret airway cells) more transcriptionally active than the pGL3-based plasmids (FIG. 2A), suggesting that inclusion of the AAV ITR and/or the fCFTR stuffer sequences had an overall positive effects on activity of the tg83 promoter. Then reporter-gene expression for pAV2-F1tg83luc, pAV2-F5tg83luc, pAV2-F10tg83luc, and pAV-tg83luc plasmids was compared. As expected, the F1, F5 and F10 enhancers significantly improved transcription from the tg83 promoter (about 10- to 19-fold) in both cell types (FIG. 2B). However, the effectiveness of nearly all enhancers was significantly reduced (about 3- to 18-fold) within the rAAV proviral plasmids when compared to pGL3-tg83 plasmids lacking ITRs and the CFTR sequence (FIG. 2B solid bars vs. FIG. 1B; FIG. 2B open bars vs FIG. 1D). This suggests that the sequences from the AAV ITR and/or portions of the ferret CFTR cDNA have an overall negative impact on enhancer function. However, this effect on the synthetic enhancers differed between the A549- and ferret primary airway-cell monolayers. In A549 cells, the F1 enhancer was most significantly influenced, with its activity in the rAAV proviral plasmid decreased by 18.1-fold, whereas those of the F5 and F10 enhancers decreased by only 8.2-fold and 3.8-fold, respectively. In primary ferret airway cells, the F1 and F5 enhancers had 4.4-fold and 2.8-fold decreased activity, respectively, in the context of the proviral plasmid, whereas the function of F10 was slightly enhanced (about 40%).

Next expression from the various enhancer elements was evaluated in the context of rAAV2/2 vectors. In A549 cells, similar increases in expressions from the enhancer/tg83 promoter combination were observed following the transfection with the proviral plasmid and infection with the corresponding rAAV vector (FIG. 2B solid bars vs. FIG. 2C). Primary human and ferret airway epithelial ALI culture were then infected with equal titers of each rAAV vector, and transgene expression was assessed at 2 days post-infection. These experiments demonstrated that F5tg83 is the most efficient promoter in both human and ferret ALI cultures (FIGS. 2D and 2E), leading to 19.6-fold and 57.5-fold increases, respectively, in tg83-driven transcription over that driven by the enhancer-less control (FIGS. 2D and 2E). Notably, the differentiated state of ferret airway epithelial cells appeared to dramatically influence expression from the various enhancer/tg83 promoter combinations in the context of rAAV transduction; the F5 enhancer more effectively enhanced tg83 expression in the polarized epithelium (FIG.

2E; 57.5-fold) than in undifferentiated monolayers (FIG. 2B; 16.6-fold); the F1 enhancer only marginally increased activity of the tg83 promoter in polarized cells, but increased transgene expression 13.8-fold in monolayer cells.

Lastly, the in vivo activities of the F5tg83 and F10tg83 promoters were compared in the airways of newborn ferrets, using intratracheal injection of two rAAV1 capsid pseudotyped vectors (AV2/1.F5tg83luc and AV2/1.F10tg83luc; equal particle titers injected). This capsid serotype had previously been shown to be effective at transducing the ferret airways in the presence of a proteasome inhibitor (Yan et al., 2013). Luciferase activity was measured in extracts prepared from tracheal and lung tissue at 8-day post-infection, and F5tg83 was found to be more effective than F10tg3 in transducing both ferret lung and trachea (FIG. 2F). These findings were consistent with those for polarized ferret airway epithelial ALI cultures (FIG. 2E).

Figure 3:
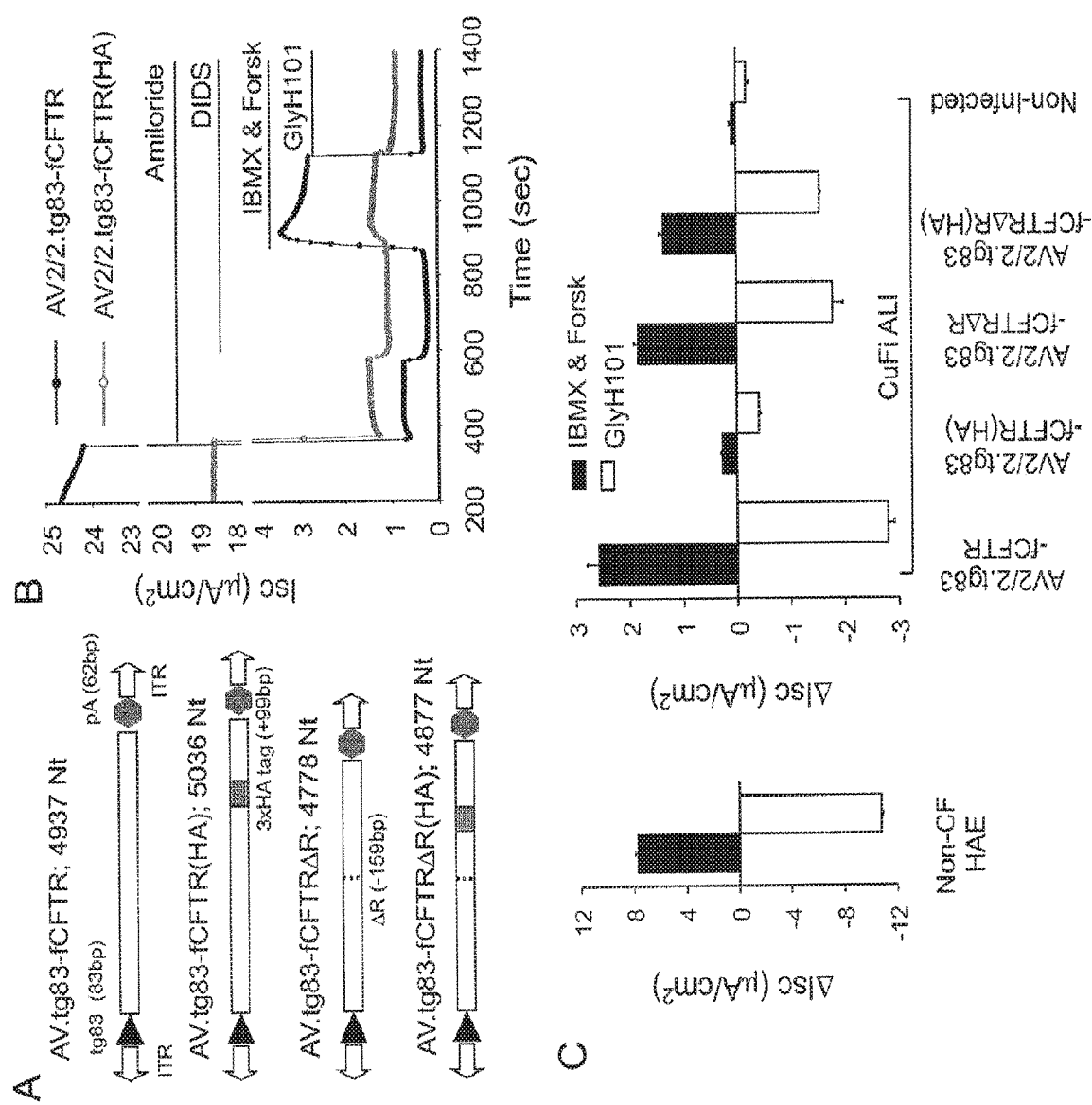

A Narrow Limit for rAAV Genome Size Significantly Influences Functionality of rAAV-CFTR Vectors While Not Altering Packaging Efficiency The size of the expected AV.tg83fCFTR genome if fully packaged is 4.937 kb (FIG. 3A). Incorporation of the F5 enhancer would increase this to 5.040 kb. Although it is well accepted that AAV can encapsidate a rAAV genome slightly longer than its natural size (4.679 kb), gradually increasing the size of a rAAV vector from 4.675 kb to 4.883 kb and 5.083 kb results in 25% and 75%, respectively, decreases in transduction (Dong et al., 1996). Furthermore, single-molecule sequencing (SMS) of the two rAAV termini following packaging of a 5.8 kb proviral genome revealed that the 5' ITR was unstable and had incurred deletions (Kapranov et al., 2012). Given that the limits for functional genome packaging in the context of rAAV-CFTR vectors have yet to be defined, it was uncertain whether a 5.04 kb AV.F5tg83fCFTR genome would be compromised with respect to genome stability and function.

This question was addressed by constructing a 5.036 kb AV2.tg83-fCFTR(HA) vector in which the CFTR expression cassette was expanded by the addition of a 3×HA epitope tag (99 nucleotides) in the region encoding the fourth extracellular loop (ECL4) of ferret CFTR (previous studies had revealed that this insertion has no impact on chloride-channel function (Glozman et al., 2009; Fisher et al., 2012)). This vector allowed us to interrogate how size of the genome influences CFTR functionality in the absence of changes to transcription of the transgene. Two rAAV2 vectors were produced (AV2/2.tg83-fCFTR and AV2/2.tg83-fCFTR-HA; FIG. 3A), and their ability to generate CFTR-mediated chloride currents was evaluated in polarized CF HAE. Vector yields for the two viruses were nearly equivalent (AV2/2.tg83-fCFTR about $5 \times 10^9$ DRP/µL and AV2/2.tg834CFTR(HA) about $3 \times 10^9$ DRP/µL). Polarized CF HAE were cultured at an ALI and infected at the relatively high multiplicity of infection (MOI) of about $10^5$ DRP/cell ($10^{11}$ DRP of each rAAV2 vector per insert). At 10 days following infection, the level of CFTR expression was determined by measuring short circuit current (Isc), as described in Zhang et al. (2004) and Fisher et al. (2011). FIG. 3B shows a typical Isc trace following infection of CF HAE with AV2/2.tg83-fCFTR or AV2/2.tg834CFTR-HA. Amiloride and DIDS were first applied to block non-CFTR chloride channels and ENaC-mediated sodium currents, and then cAMP agonists (IBMX and forskolin) were used to induce CFTR activity. The changes in Isc following the addition of IBMX and forskolin ($\Delta Isc_{IBMX\ \&\ Forsk}$) and the subsequent addition of the CFTR inhibitor GlyH101 ($\Delta Isc_{glyH}$) were used to evaluate the function of CFTR. These results clearly demonstrated that functional complementation of CFTR activity in CF HAE is greater following infection with AV2/2.tg83-fCFTR than with AV2/2.tg83-fCFTR-HA (FIG. 3B). The mean $\Delta Isc_{IBMX\ \&\ Forsk}$ and $\Delta Isc_{glyH}$ values from these experiments are summarized in FIG. 3C. CFTR-mediated cAMP-inducible Cl$^-$ currents produced by AV2/2.tg83-fCFTR(HA) were only 3.6% those in a non-CF HAE ALI cultures, but still above background levels (p<0.01). By contrast, infection with AV2/2.tg83-fCFTR produced 10-fold greater cAMP-inducible Cl$^-$ currents than AV2/2.tg83-fCFTR(HA) and achieved about 30% CFTR activity of non-CF HAE ALI cultures. These results demonstrate that the cutoff for retaining CFTR function is very narrow when producing oversized rAAV genomes, and that vector functionality does not depend only on the efficiency of packaging DRPs. Furthermore, these studies suggest that incorporation of the 100 nucleotide F5 enhancer into AV2/2.tg83-fCFTR, with a total genome size of 5.04 kb, may have a significant negative impact on function of the genome.

Effective Packaging of a Functional Ferret CFTR Mini Gene into rAAV

Next, the possibility of using a shortened ferret CFTR minigene was explored, to further reduce the genome size of a rAAV-CFTR vector, and to allow for incorporation of the F5 enhancer. A human CFTR minigene (CFTRΔR) with a 156 bp partial deletion of the R-domain (encoding amino acids 708-759) has been reported to retain most of the chloride-channel activity of the full-length protein (Ostedgaard et al., 2002; Ostedgaard et al., 2011). A fCFTRΔR minigene was created by deleting the 159 bp homologous sequence encoding amino acids 708-760 at the corresponding position of the human protein, and produced two additional vectors: AV2/2.tg83-fCFTRΔR (4.778 kb) and AV2/2.tg83-fCFTRΔR(HA) (4.877 kb). This pair of vectors allowed for the examination not only the function of the fCFTR minigene in CF HAE ALI cultures, but also the impact of the HA-tag insertion in the fCFTR gene. Analysis of $\Delta Isc_{IBMX\ \&\ Forsk}$ and $\Delta Isc_{glyH}$ responses for these two viruses demonstrated that both AV2/2.tg83-fCFTR and AV2/2.tg83-fCFTR(HA) produced substantial CFTR-mediated Cl$^-$ currents following infection of the CF HAE ALI cultures (FIG. 3C). However, the HA-tagged form produced about 20% less Cl$^-$ current than AV2/2.tg83-fCFTRΔR. This finding is consistent with rAAV vectors of 4.88 kb having only about 25% of the functional activity of vectors 4.68 kb (Dong et al., 1996). Alternatively, the HA-tag may itself influence CFTR function in the context of the R-domain deletion, although in the context of full-length CFTR this ECL4 HA-tag has no impact on Cl$^-$ channel function (Glozman et al., 2009; Fisher et al., 2011). Despite the larger genome size of AV2/2.tg83-fCFTR (4.9437 kb), this vector produced about 30% more CFTR-mediated current than its shorter counterpart AV2/2.tg83-fCFTRΔR (4.778 kb) (FIG. 3C). This reduction in Cl$^-$ channel activity of fCFTRΔR is similar to that reported for hCFTRΔR (Ostedgaard et al., 2002). However, given the potential for reduced functionality of larger vector genomes, the impact of the R-domain deletion on the function of the ferret CFTR protein is likely greater than that for human CFTR.

To establish the impact of genome length on packaging of the rAAV vectors tested, the integrity of the viral genome was examined, using alkaline-denatured agarose gel electrophoresis followed by Southern blotting (FIG. 4A). This analysis revealed that the smallest vector genome (i.e. that of AV2.tg83-fCFTRΔR, 4.778 kb) could be distinguished from the other three viruses based on its faster migration through the gel (AV2.tg83-fCFTRΔR is 99 nucleotides shorter than the AV2.tg83-fCFTRΔR(HA) vector). However, AV2.tg83-fCFTR(HA) (5.036 kb), AV2.tg83-fCFTR (4.937 kb) and AV2.tg83-fCFTRΔR(HA) (4.887 kb) could not be distinguished from one another on the basis of this analysis. Given that it should be possible to visualize differences of both 149 nucleotides (AV2.tg83-fCFTR(HA) vs. AV2.tg83-fCFTRΔR (HA)) and 99 nucleotides (AV2.tg83-fCFTR(HA) vs. AV2.tg83-fCFTRΔR(HA), and AV2.tg83-fCFTR(HA) vs. AV2.tg83-fCFTR), these findings were interpreted as support for the notion that viral genomes larger than that of AV2.tg83-fCFTRΔR(HA) (4.887 kb) tend to incur deletions that compromise CFTR transgene expression.

The notion that deletion occurs in the context of longer genomes was further supported by the hybridization of viral genomes with two sets of plus and minus strand oligonucleotide probes at the center of CFTR cDNA, the tg83 promoter, and synthetic poly-A sequences (FIG. 4B). Results from this analysis demonstrated viral DNA from the largest AV2.tg83-fCFTR(HA) vector incurred deletions at both the 5' ends of positive and minus strand genomes. By contrast, the 3' end of positive and minus strand AV2.tg83-fCFTR (HA) genomes remained intact, consistent with packaging of single stranded AAV genomes from the 3' to 5' direction. The fact that the strength of hybridization at the tg83 promoter (for positive strand), and the polyA sequence (for minus strand), was lower than that of hybridization to the fCFTR cDNA suggested that these deletions were not restricted to the ITR region (i.e., that the damage extended into the CFTR expression cassette). Such deletions were not observed in the second longest vector, AV2.tg83-fCFTR, therefore, the CFTR expression cassette in this vector most likely still remains intact, although partial deletions in the ITR region likely occur as suggested from the viral DNA migration on denatured agarose gel. While deletions in the ITR regions may not directly influence expression of the CFTR transgene, they may impact the stability of viral genomes and thus indirectly influence CFTR expression. These results, together with the functional analysis, led to the conclusion that the fCFTRΔR cDNA without the HA-tag would be best suited for testing the impact of the F5 enhancer on rAAV-mediated CFTR complementation.

The Synthetic F5tg83 Promoter Improves rAAV-Mediated CFTR Complementation

Figure 5:
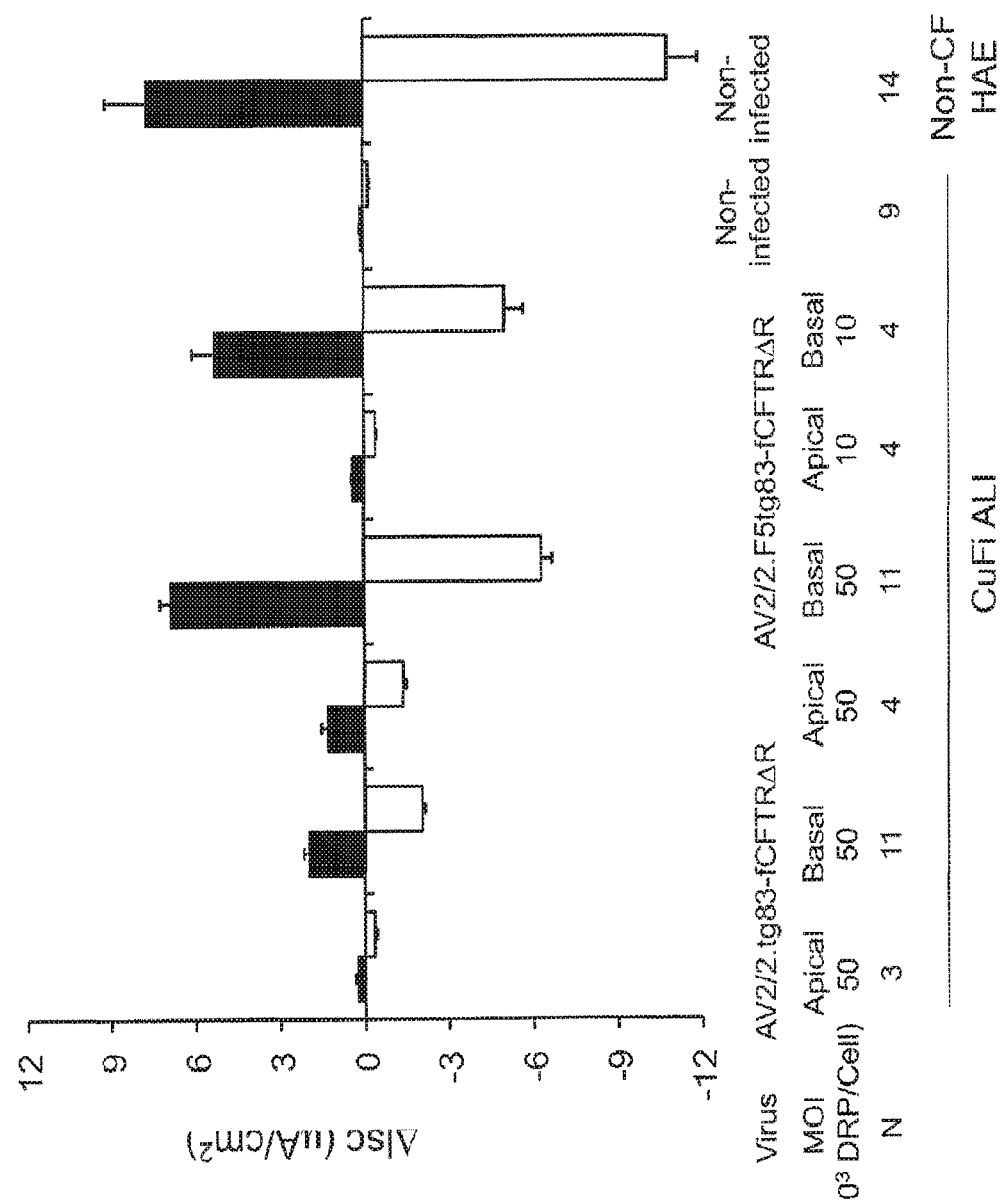

Next, the pAV2.F5tg83-fCFTRΔR proviral plasmid was generated and AV2/2.F5tg83-fCFTRΔR virus with a genome size of 4.87 kb was produced. The efficiency of this virus for complementing function of the CFTR channel following infection of polarized CF HAE was compared to that of the enhancer-less counterpart vector (AV2.tg83-fCFTRΔR). Results from this analysis demonstrated that incorporation of the F5 enhancer greatly improved the CFTR-mediated Cl⁻ currents (FIG. 5). At two weeks following basolateral infection at an MOI of $5\times10^4$ DRP/cell, cAMP-induced CFTR-mediated Cl⁻ currents were 3.5-fold greater for AV2/2.F5tg83-fCFTRΔR than for AV2/2.tg83-fCFTRΔR, and the former was 89% of those observed in non-CF primary HAE. A similar improvement in CFTR function (4.8-fold) was observed with AV2/2.F5tg83-fCFTRΔR following apical infection, but in this case the efficiency of transduction was significantly lower, as previously reported for this serotype. At the reduced MOI of $1\times10^4$ DRP/cell basolaterally, AV2/2.F5tg83-fCFTRΔR produced 69% of the CFTR current generated by this vector at a 5-fold higher MOI, suggesting that complementation of CFTR function approached saturation in the latter case. Thus, when one compares the effectiveness of AV2/2.F5tg83-fCFTRΔR ($1\times10^4$ DRP/cell) and AV2/2.tg83-fCFTRΔR ($5\times10^4$ DRP/cell) vectors in the context of optimal infection (i.e., basolateral) and non-saturating conditions, incorporation of the F5 enhancer improved the vector efficacy by 13.5-fold. This level of increase in current is consistent with the increase in expression observed with the analogous luciferase expression vectors (FIG. 2D, 19.6-fold).

Given the apparent saturation of CFTR currents at the highest MOI ($5\times10^4$ DRP/cell) following basolateral infection with AV2/2.F5tg83-fCFTRΔR, the kinetics of CFTR expression were evaluated at an intermediate MOI ($2\times10^4$ DRP/cell). Measurements were carried out 3 and 10 days following infection of CF HAE with AV2/2.F5tg83-fCFTRΔR and AV2/2.tg83-fCFTRΔR. Results from this analysis demonstrated that, in the context of the F5 enhancer, the onset of CFTR-mediated Cl⁻ currents was more rapid than in its absence (FIG. 6A). In fact, CFTR currents were maximal by 3 days after infection with AV2/2.F5tg83-fCFTRΔR, whereas currents increased 3.6-fold between 3 and 10 days after infection with AV2/2.tg83-fCFTRΔR. To more directly compare transcriptional activity between these vectors, the ferret CFTR mRNA was examined by real-time RNA-specific reverse transcriptase PCR (RS-PCR), a method that prevents amplification of vector-derived DNA products and was previously applied in detecting the CFTR mRNA from rAAV-infected cells and tissues (Zhang et al., 2004; Gerard et al., 2003). Analyses of the RS-PCR results, after normalization to ferret GAPDH transcripts, demonstrated 6.4-fold and 17.1-fold higher levels of fCFTR mRNA following infection with AV2.F5tg83-fCFTRΔR vs. AV2/2.tg83-fCFTRΔR, at the 3 and 10 day time points, respectively (FIG. 6B). The 10-fold increase in CFTR mRNA observed between 3 and 10 days after infection confirms that CFTR currents were saturated by 3 days post-infection. Thus, at the transcriptional level, incorporation of the F5 enhancer increased CFTR expression 17.1-fold, closely mirroring the results observed with luciferase expression vectors (FIG. 2D, 19.6-fold).

Discussion rAAV vectors have attracted considerable interest with respect to human gene therapy, but its inherently small genome (4.679 kb) is a significant challenge for the delivery of large genes such as CFTR. Although several laboratories have attempted to rationally design short enhancers and promoters for use in rAAV vectors, this approach has yet to yield robust expression of CFTR in the airway. In the present study, an entirely empirical approach was taken by screening synthetic enhancers for their effectiveness in the delivery of reporter gene expression in step-wise fashion—in plasmids, proviral vectors, and viral vectors. While the main goal was to develop rAAV vectors for delivering CFTR to the airway, a similar approach may prove useful for gene therapy efforts tackling the delivery of other large genes (e.g., Factor VIII and dystrophin) that necessitate the use of short promoters.

Production of an oversized rAAV genome is known to lead to random deletions at the 5' end of the encapsidated single stranded genomes (Kapranov et al., 2012), but the functional integrity of rAAV vector genomes that approach the accepted maximum capacity of rAAV (about 5.0 kb) has not been thoroughly investigated. The current study provides, in the context of CFTR-expressing rAAV vectors, evidence that functionality of the rAAV genome begins to decline well below this 5.0 kb cut off. Evidence in support of this includes a reduction in CFTR function for 4.877 kb vs. 4.778 kb genomes (FIG. 3C) and the lack of differences in the migration of 4.877-5.036 kb single-stranded genomes when visualized on alkaline gels (FIG. 4A). Additionally, the largest CFTR vector (5.036 kb) incurred deletion in about 30% of genomes that extend beyond the 5' ITR and into the promoter (in the case of the positive strand) or polyA region (in the case of the minus strand). This suggests that damage to the CFTR expression cassette may be responsible for the significant impairment of function of CFTR delivered by this vector. While the oligo probes used only detected deletions in 30% of genomes for this largest construct, the 90% reduction in CFTR chloride current between 4.937 vs 5.036 kb vectors suggests that a much larger percentage of genomes incur functional deletions and that ITR deletions may also impair vector performance.

The present findings seem inconsistent with previous observations of an only 4-fold change in transgene expression between rAAV vectors that are 4.7 kb and 5.2 kb in size (Wu et al., 2010). However, in this earlier study the stuffer sequence used to expand the vector was positioned between the expression cassette and the ITR, and deletions of the stuffer sequence would likely have less of an impact on the transcriptional activity of the transgene. The current study of the AAV-CFTR vector instead employed a short synthetic promoter and poly-A signal, and small deletions within these short transcriptional regulatory elements would be expected to greatly influence gene expression. Since DNase resistant particle titer is typically used to confirm effective packaging of rAAV genomes, small 5-end deletions could have a significant impact on functionality of oversized rAAV vectors.

The empirical approach that was used to screen synthetic 100 bp enhancers for the ability to improve rAAV-mediated transgene expression in the airway yielded several important observations: 1) Enhancer activity differed by cell lines and also the state of cell differentiation. 2) Enhancer activity was influenced by the AAV ITRs and might also be influenced by the sequence of gene of interest (in this study, the 3' half of the ferret CFTR cDNA coding region), 3) Enhancer activity in the case of rAAV infection was generally similar to that in the context of proviral vector, though with subtle differences, 4) Infection of human and ferret airways with viral vectors revealed some differences in enhancer function (most notably for AV2/2.F1tg83luc, FIGS. 2D and 2E). These results indicate that although transfection with proviral plasmid is suitable for initial screens of synthetic enhancers, performing such a screen in unpolarized primary airway cultures may not produce the same patterns of gene expression observed following AAV infection of polarized airway cultures.

Through this screen, a 100 bp synthetic enhancer (F5) was identified that significantly improves the transcriptional activity of an 83 bp synthetic promoter (tg83), in polarized cultures of both primary human and ferret airway epithelial cells, as well as in ferret lung and trachea in viva. The ferret CFTR minigene lacking a 53 amino acid portion of the R domain (fCFTRΔR) retained about 70% of wild type fCFTR function, similar to the 80% function retained by a previously reported, analogous hCFTRΔR construct (Ostedgaard et al., 2002). Nevertheless, this was greatly compensated by the increased transgene expression from AV2.F5tg83-fCFTRΔR, as the use of the shortened minigene spares 150 bp space to allow for the incorporation of the F5 enhancer.

Figure 6:
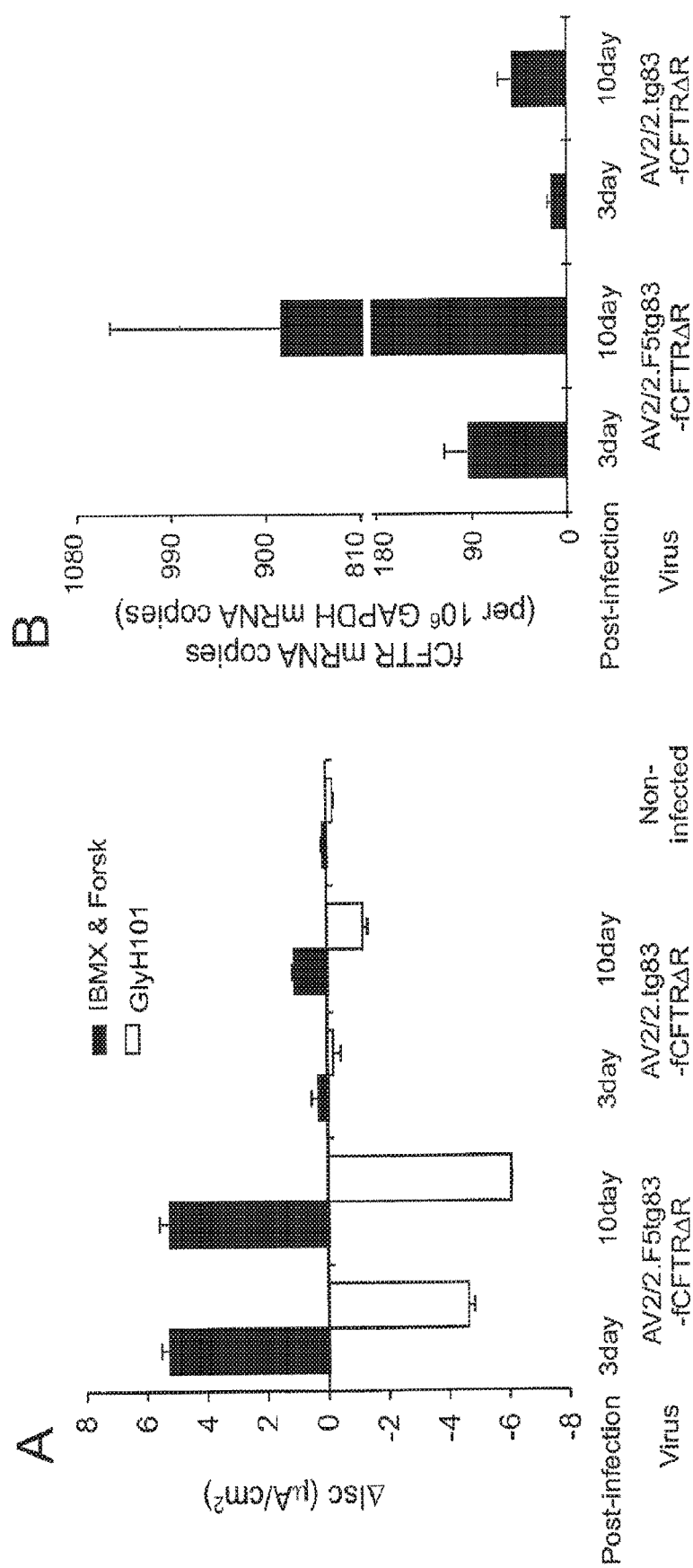

In the context of a rAAV vector, the F5 enhancer significantly improved tg83-driven CFTR mRNA expression (17.1-fold) at 10 days post-infection of CF HAE relative to the AV2/21tg83-fCFTRΔR vector, which lacks this enhancer. This increase in CFTR mRNA expression from AV2/2.F5tg83-fCFTRΔR correlated well with the 19.6-fold improvement in CFTR-mediated currents made possible by this vector, and resulted in production of about 89% of the cAMP-mediated Cl⁻ currents observed in non-CF HAE. Of note, a ceiling on the level of functional correction that can be achieved with respect to the changes in lsc was found. In the time-course studies, maximal correction of lsc in CF HAE was achieved by 3 days post-infection, with the about 10 fold increase in CFTR mRNA by 10 days post-infection yielding no improvement in Cl⁻ currents (FIG. 6). These findings provide important insight into evaluating the functionality of rAAV-CFTR vectors: dose responses of the vector are needed for accurate comparison of vector designs. The ceiling on CFTR currents could reflect self-limiting cell biology (e.g., control over the total amount of CFTR on the plasma membrane), or aberrant trafficking of CFTR to the basolateral membrane at higher levels of expression (Farmen et al., 2005).

In summary, a rAAV-CFTR vector was generated that provides high-level expression suitable for use in lung gene therapy studies in the CF ferret model. Moreover, the present findings suggest that small synthetic enhancers and promoters may be useful tools for optimizing the design of rAAV vectors for the delivery of large transgenes.

Summary

As discussed herein, small synthetic enhancer/promoter combination, sized about or less than 200 bp, can be used in rAAV vector to deliver effective transgene expression of a large transgene expression; in this study, the gene is CFTR, As also discussed herein, empirical approach to screen a set of 100-mer synthetic enhancer elements for their ability to augment reporter expression from a shod 83-bp synthetic promoter (tg83p) in lung airway tissue. Partial sequence of the gene of interest (in the study is CFTR) is included to the reporter vector to maximize the effect to screen the best enhancer sequence. The screening was conducted in stepwise fashion—in plasmids, proviral vectors, and rAAV vectors, and in different cell/tissue levels—in monolayer (non-polarized) cultures of human airway cell lines and primary ferret airway cell, in polarized cultures of human and ferret airway epithelia at an air-liquid interface (ALI) and ferret airway in vivo. The enhancer activity differs by cell lines and state of cell differentiation, as well as is influenced by the AAV ITRs and by the sequence of gene of interest. Thus, the effects of an enhancer in the context of plasmid transfection may be different from that in the context of rAAV transduction. The in vivo effects of a particular enhancer may not be predictable from its behaviors demonstrated in culture cell lines. This, the screening needs to be conducted in different cell/tissue levels and in a step-wise fashion—in plasmids, proviral vectors, and rAAV vectors to warrant the success.

Three of synthetic enhancers (F1, F5, and F10) were found significantly increase the transcription of tg83p for luciferase transgene in the context of plasmid transfection. The F5tg83 promoter, the 183 bp combination of F5 enhancer and tg83p, was the most efficient promoter in human and ferret ALI cultures, leading to 19.6-fold and 57.5-fold increases reporter expression, respectively, over the enhancer-less counterpart. The F5tg83 promoter also produced the highest level of transgene expression in the ferret airway in vivo. When the F5tg83 promoter was used to transcribe the 4.2 kb CFTR minigene (CFTRΔR) in a rAAV vector, it yielded an about 17-fold increase in vector derived CFTR mRNA transcription and significantly improved Cl⁻ currents in human CF ALI cultures, compared to the vector using tg83p only.

The enhancer/promoter combinations for lung epithelium (e.g., F5tg83) may not necessarily be as useful for other organs/tissue. For example, when AAV vectors harboring a luciferase reporter gene driven by F5tg83 or F10tg83 were used to infect different tissues/organs of the digestive system, F5tg83 demonstrated the strongest promoter activity in pancreas, gallbladder and liver, whereas F10tg83 outperformed F5tg83 in small intestine (FIGS. 7A-7B).

Although the studies were focused on identifying strong synthetic enhancer/promoter sequence using for efficiently expressing CFTR in lung/airway tissue, the screen approach can be used for any desired cell types, tissues and organs in vitro and in vivo.

Thus, the use of short enhancer elements (about 100-mer synthetic oligonucleotide sequences consisting of 10-mer repeats) was found to enhance gene expression from a minimal promoter in rAAV vectors. These 100 bp enhancer elements were previously identified for their ability to activate transcription directed by the CMV immediate-early (IE) minimal promoter in cell lines (Schlabach et al., 2010). It was hypothesized that enhancers that are most potent in activating transcription could be used to enhance activity of the synthetic tg83 promoter in airway cells in the context of rAAV vectors. Eight combinations of the tg83 promoter and 100 bp synthetic enhancers were tested, and one designated as F5 efficiently was found to enhance the transcription from the tg83 promoter in polarized airway cells (in vitro) derived from both humans and ferrets, as well as in the ferret airway (in vivo). Using the F5tg83 promoter and the ferret CFTR minigene of partial deletion at R domain (fCFTRΔR), a rAAV vector (AV2/2.F5tg83-fCFTRΔR) was found and its ability to correct CFTR-mediated Cl⁻ transport in CF ALI cultures tested.

Example 2

AV.F5Tg83-hCFTRΔR was tested for hCFTR expression in the newborn and mature ferret airway. An endpoint of these analyses was the ratio of transgene-derived human CFTR (hCFTR) to that of endogenous ferret CFTR (fCFTR) mRNA. In 3 day old newborn ferrets (FIG. 9), AV.F5Tg83-CFTRΔR led to 240% greater expression of human CFTR compared with endogenous (ferret) CFTR following gene delivery to the lung.

Given that the phenotype of ferret airway epithelia and the secretions in the airway change as the lungs mature, it was evaluated whether AV.F5Tg83-CFTRΔR transduces the mature ferret airway and the promoter remains active. To this end, the ability of AV.F5Tg83-CFTRΔR to transduce the lung of 1 month old ferrets was evaluated. In 1 month old mature ferrets (FIG. 10), AV.F5Tg83-CFTRΔR led to 300% greater expression of human CFTR compared with endogenous (ferret) CFTR following gene delivery to the lung. Furthermore, the ratio of human to ferret CFTR was approximately one in the nasal passage. These findings from newborn and mature ferrets suggest that the F5Tg83 promoter robustly expresses the CFTR transgene in the lung in vivo.

REFERENCES

Aitken et al., Chest, 123:792 (2003).
Aitken et al., Hum Gene Ther., 12:1907 (2001).
Carter, Hum Gene Ther., 16:541 (2005).
Conrad et al., Gene Ther., 3:658 (1996).
Daya & Berns, Clin. Microb. Rev., 21:583 (2008).
Ding et al., Gene Ther., 12:873 (2005).
Ding et al., Mol. Ther., 13:671 (2006).
Dong et al., Hum. Gene Ther., 7:2101 (1996).
Duan et al., Hum. Gene Ther., 9:2761 (1998).
Duan et al., J. Clin. Invest., 105:1573 (2000).
Farmen et al., Am. J. Physiol. Lung Cell Mol. Physiol., 289:1123 (2005).
Fisher et al., J. Biol. Chem., 287:21673 (2012).
Flotte et al., J. Biol. Chem., 268:3781 (1993).
Flotte, Curr. Opin. Mol. Ther., 3: 497 (2001).
Flotte, et al., J. Biol. Chem., 268:3781 (1993).
Gerard et al., Gene Ther., 10:1744 (2003).
Glozman et al., J. Cell Biol., 184:847 (2009).
Griesenbach et al., Virus Adapt. Treat., 2:159, (2010).
Griesenback & Mon, Adv. Drug Deliv. Rev., 61:128 (2009).
Kapranov et al., Hum. Gene Ther., 23:46 (2012).
Karp et al., Methods Mol. Biol., 188:115 (2002).
Li et al., Mol. Ther., 17:2067 (2009).
Liu et al., Am. J. Respir. Cell Mol. Biol., 36:313 (2007).
Liu et al., Gene Ther., 14:1543 (2007).
Liu et al., Mol. Ther., 15:2114 (2007).
Moss et al., Hum. Gene Ther., 18:726 (2007).
Mueller & Flotte, Clin. Rev. Allergy Immunol., 35:164 (2008).
Olivier et al., J. Clin. Invest., 122:3755 (2012).
Ostedgaard et al., Proc. Natl. Acad. Sci. USA, 102:2952 (2005).
Ostedgaard et al., Proc. Natl. Acad. Sci. USA, 108:2921 (2011).
Ostedgaard et al., Proc. Natl. Acad, Sci. USA, 99:3093 (2002).
O'Sullivan & Freedman, Lancet, 373:1891 (2009).
Riordan et al., Science 245:1066 (1989).
Rommens et al., Science, 245:1059 (1989).
Rowe et al., N. Engl. J. Med., 352:1992 (2005).
Schlabach et al., Proc. Natl. Acad, Sci. USA, 107:2538 (2010).
Summer-Jones et al., Gene Therapy for Cystic Fibrosis Lung Disease, Birkhauser Basel, Basel (2010).
Sun et al., Am. J. Pathol., 184:1309 (2014).
Sun et al., Am. J. Respir. Cell Mol. Biol., 50:502 (2014).
Sun et al., J. Clin. Invest., 118:1578 (2008).
Sun et al., J. Clin. Invest., 120:3149 (2010).
Wagner et al., Hum. Gene Ther., 13:1349 (2002).
Welsch, FASEB. J., 4:2718 (1990).
Welsh et al., In The Metabolic and Molecular Bases of Inherited Disease, eds. McGraw-Hill, New York, p. 3799 (1995).
Wu et al., Mol. Ther., 14:316 (2006).
Wu et al., Mol. Ther., 18:80 (2010).
Yan et al., Hum. Gene Ther., 24:786 (2013).
Yan et al., Hum. Gene Ther., 26:334 (2015).
Yan et al., J. Virol., 76:2043 (2002).
Yan et al., J. Virol., 78:2863 (2004).
Yan et al., Mol. Ther., 21:2181 (2013).
Zabner et al., Am J. Physiol. Lung Cell Mol. Physiol., 284:844 (2003).
Zhang et al., Mol. Ther., 10:990 (2004).
Zhang et al., Proc. Natl. Acad, Sci. USA, 95:10158 (1998).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An isolated recombinant parvovirus vector comprising a synthetic enhancer operably linked to a promoter, wherein the enhancer and promoter have a sequence having at least 90% nucleotide sequence identity to SEQ ID NO:27.

2. The recombinant parvovirus vector of claim 1 which is a bocavirus or an adeno-associated virus vector.

3. The recombinant parvovirus vector of claim 1, wherein the promoter is operably linked to an open reading frame that encodes a prophylactic or therapeutic gene product.

4. The recombinant parvovirus vector of claim 1, wherein the synthetic enhancer and promoter have at least 95%, 98%, 99% or more nucleic acid sequence identity to SEQ ID NO:27.

5. An isolated vector comprising a synthetic enhancer operably linked to a promoter, wherein the enhancer and promoter have a sequence having at least 90% nucleotide sequence identity to SEQ ID NO:27.

6. The vector of claim 5, wherein the promoter is operably linked to an open reading frame.

7. The vector of claim 6, wherein the open reading frame encodes a prophylactic or therapeutic gene product.

8. The vector of claim 5, wherein the synthetic enhancer and promoter have at least 95%, 98%, 99% or more nucleic acid sequence identity to SEQ ID NO:27.

9. The vector of claim 5 which is a plasmid.

10. The recombinant parvovirus vector of claim 1, wherein the enhancer and promoter have at least 95% nucleotide sequence identity to SEQ ID NO:27.

11. The recombinant parvovirus vector of claim 10, wherein the enhancer and promoter have at least 98%, 99%, or more nucleic acid sequence identity to SEQ ID NO:27.

12. The recombinant parvovirus vector of claim 11, wherein the enhancer and promoter comprise the sequence of SEQ ID NO:27.

13. The recombinant parvovirus vector of claim 3, wherein the therapeutic gene product is cystic fibrosis transmembrane conductance regulator (CFTR) or CFTRΔR.

14. The recombinant parvovirus vector of claim 13, wherein the CFTR or CFTRΔR is human CFTR or human CFTRΔR.

15. A recombinant adeno-associated vector comprising: (i) an enhancer operably linked to a promoter, wherein the enhancer and promoter comprise the sequence of SEQ ID NO:27; and (ii) a human CFTRΔR transgene operably linked to the promoter.

* * * * *